US011697679B2

(12) United States Patent
Miwa et al.

(10) Patent No.: US 11,697,679 B2
(45) Date of Patent: Jul. 11, 2023

(54) MODIFIED COLLAGEN PROTEIN AND APPLICATION OF SAME

(71) Applicant: UNIVERSITY OF TSUKUBA, Tsukuba (JP)

(72) Inventors: Yoshihiro Miwa, Tsukuba (JP); Junko Kijima, Tsukuba (JP)

(73) Assignee: UNIVERSITY OF TSUKUBA, Tsukuba (JP)

( * ) Notice: Subject to any disclaimer, the term of this patent is extended or adjusted under 35 U.S.C. 154(b) by 405 days.

(21) Appl. No.: 16/761,768

(22) PCT Filed: Nov. 14, 2018

(86) PCT No.: PCT/JP2018/042181
§ 371 (c)(1),
(2) Date: May 5, 2020

(87) PCT Pub. No.: WO2019/098246
PCT Pub. Date: May 23, 2019

(65) Prior Publication Data

US 2021/0002349 A1 Jan. 7, 2021

(30) Foreign Application Priority Data

Nov. 14, 2017 (JP) ................................ 2017-219515

(51) Int. Cl.

| | |
|---|---|
| ***C07K 14/78*** | (2006.01) |
| ***C07K 19/00*** | (2006.01) |
| ***C12N 15/63*** | (2006.01) |
| ***C12N 5/10*** | (2006.01) |
| ***A61K 38/39*** | (2006.01) |
| ***C12N 15/85*** | (2006.01) |

(52) U.S. Cl.
CPC ............. *C07K 14/78* (2013.01); *A61K 38/39* (2013.01); *C07K 19/00* (2013.01); *C12N 5/10* (2013.01); *C12N 15/63* (2013.01); *C12N 15/8509* (2013.01); *C07K 2319/00* (2013.01); *C07K 2319/40* (2013.01); *C07K 2319/60* (2013.01)

(58) Field of Classification Search
CPC .... C07K 14/78; C07K 2319/00; C07K 19/00; C07K 2319/60; C07K 2319/40; A61K 38/39
See application file for complete search history.

(56) References Cited

U.S. PATENT DOCUMENTS

| | | | | |
|---|---|---|---|---|
| 6,277,600 | B1 * | 8/2001 | Tomita | A61K 47/6435 435/69.7 |
| 2016/0331814 | A1 * | 11/2016 | Oxford | C07K 14/78 |
| 2018/0188266 | A1 * | 7/2018 | Stefanovic | G01N 33/5038 |
| 2019/0153068 | A1 * | 5/2019 | Ouzounov | C07K 14/78 |

FOREIGN PATENT DOCUMENTS

| | | | |
|---|---|---|---|
| JP | H08-023979 | A | 1/1996 |
| JP | 2008-067655 | A | 3/2008 |
| JP | 2010-085108 | A | 4/2010 |
| JP | 2014-076026 | A | 5/2014 |
| JP | 2000-125872 | A | 5/2020 |
| JP | 2000-506362 | A | 5/2020 |
| WO | WO 2008-032874 | A1 | 3/2008 |
| WO | WO 2012/124338 | A1 | 9/2012 |
| WO | WO 2016/152882 | A1 | 9/2016 |

OTHER PUBLICATIONS

Definition of "gene" from Merriam-Webster Dictionary, www.merriam-webster.com/dictionary/gene; accessed Sep. 4, 2019.*
English languge translation of WO 2016/152882-A1, Sep. 29, 2016.*
Gordon et al. Collagens. Cell Tissue Res 339: 247-257, 2010.*
Lodish et al., Molecular Cell Biology. 4th edition. New YorK: W.H. Freeman; 2000. Section 9.1, Molecular Definition of a Gene.*
Maye et al., "Generation and Characterization of Col10a1-mCherry Reporter Mice", Genesis, 2011, 49: 410-418.
Nomura et al., "Cell response to mechanical stretch", Molecular Cytological Review, Bulletin of the Faculty of Education, Chiba University, Japan, 2006, 54: 271-274.
Ohana et al., "HaloTag7: A genetically engineered tag that enhances bacterial expression of soluble proteins and improves protein purification", Protein Expression and Purification, 2009, 68: 110-120.
Prockop et al., "The Biosynthesis of Collagen and its Disorders", New England Journal of Medicine, 1979, 301: 13-23.
Smith et al., "Focus on Molecules: Collagens V and XI", Experimental Eye Research, 2012, 98(1): 105-106.
Thein et al., "Caenorhabditis elegans Exoskeleton Collagen COL-19: An Adult-Specific Marker for Collagen Modification and Assembly, and the Analysis of Organismal Morphology", Developmental Dynamics, 2003, 226: 523-539.
Yoshioka et al., "The α1(XI) Collagen Gene: Primary Structure of the α1 Chain, and the Gene Expression and Regulation", Connective Tissue, 1997, 29: 39-47.
International Preliminary Report on Patentability issued for PCT/JP2018/042181 dated Apr. 7, 2020.
International Search Report of PCT/JP2018/042181 dated Feb. 5, 2019.

* cited by examiner

*Primary Examiner* — Bridget E Bunner
(74) *Attorney, Agent, or Firm* — James S. Keddie; Bozicevic, Field & Francis LLP

(57) ABSTRACT

In order to develop tools and methods useful in a variety of applications, including the research and development of medical treatments which involve the modification of collagen protein and use of the same, the present invention provides a modified collagen protein expressed in a transformed cell and capable of forming collagen fibers outside of the cell, wherein the transformation is performed by introducing, into the cell, polynucleotides coding the modified collagen protein.

11 Claims, 18 Drawing Sheets

Specification includes a Sequence Listing.

(PRIOR ART)

MC3T3-E1

SUPER-RESOLUTION LASER MICROSCOPY IMAGE

MODIFIED COLLAGEN PROTEIN AND APPLICATION OF SAME

CROSS-REFERENCE TO RELATED APPLICATIONS

This application is a § 371 national phase of International Application No. PCT/JP2018/042181, filed on Nov. 14, 2018, which claims the benefit of Japanese Application No. 2017-219515, filed on Nov. 14, 2017, which applications are incorporated by reference herein.

INCORPORATION BY REFERENCE OF SEQUENCE LISTING

The sequence listing entitled "AIKA-001 SEQLIST2" created on Feb. 3, 2023, and having a size of 202 kilobytes is incorporated by reference herein.

TECHNICAL FIELD

The present invention relates to a technique for modifying a collagen protein and a novel use of the collagen protein using the same.

BACKGROUND OF THE INVENTION

Tissue fibrosis is caused by excessive wound healing associated with inflammation or injury and replacement of connective tissue with normal tissue, resulting in functional deterioration of organs and tissues (e.g., interstitial pneumonia, infection, pneumonia, etc., in the lung (which can be caused by smoking); fatty liver, etc., in the liver (which can be caused by a viral infection, alcohol, etc.); diabetes end-stage, etc., in the kidney; heart failure, etc., in the heart; or postoperative adhesions, etc.). They are particularly prone to occur in the terminal stages of various diseases and are a major cause of organ failure. Analysis of these occurrences requires a series of analyses by dissection of laboratory animals (i.e., invasive methods).

The N- or C-terminus of a collagen protein was cleaved and removed when it was secreted out of the cell. Therefore, conventionally, imaging in which a fluorescent protein or the like was added to the N- or C-terminus could only detect intracellular transport process, and it was impossible to visualize collagen fiber after the cleavage at the time of exiting outside the cell since only the central portion (triple helix portion) of a long collagen polypeptide is involved in fiber formation.

Also, the triple helix portion involved in fiber formation is a conserved portion between species and is structurally stable, so it has been difficult to insert other proteins into this portion (FIG. 1; Non-Patent Document 1: Prockop D J et al., New Engl J Med, Vol. 301, 13-23, 1979). Therefore, labeling by common fusion protein techniques was difficult.

Among the fibrosing constituents Type I, III, V, and XI collagens, Type V and XI collagens have exceptionally uncut N-terminal domains, and in particular, when they assemble with other collagens such as Type I to form thick fibers, the N-terminal domains of Type V collagen are most likely to be aligned outward of the fibers (FIG. 2; Non-Patent Document 2: Simone M. Smith and David E. Birk, Exp Eye Res Vol. 98, 105-106, 2012).

Methods for producing a human collagen expression vector and for a human collagen have been reported in a patent document (Patent Document 1: JP-A-08-023979). In this literature, it has been reported that a full length of human type 3 collagen gene was incorporated into a vector and expressed, and although a correct protein appears to be synthesized as long as on an electrophoresis, it has not been described as to whether it forms a native collagen fiber extracellularly. Sf9 cells do not produce other types of collagen in the first place, and it seems unlikely that these cells can be used to form the correct collagen fibers. There is also a document to report a probe for biological tissue analysis and its utilization method (Patent Document 2: WO2012/124338). This document discloses a probe in which a fluorescent protein or the like is added to a collagen-binding domain of a collagen degrading enzyme.

PRIOR ART DOCUMENTS

Patent Document 1: Japanese Patent Application Publication No. 08-023979

Patent Document 2: WO2012/124338

Non-Patent Document 1: Prockop D J et al., New Engl J Med, Vol. 301, 13-23, 1979

Non-Patent Document 2: Simone M. Smith and David E. Birk, Exp Eye Res Vol. 98, 105-106, 2012

SUMMARY OF THE INVENTION

The present invention aims at the development of tools, methods and the like useful for modification of collagen proteins (e.g., insertion and addition of foreign proteins) and various applications using the same, including research or therapeutic development (e.g., non-invasive imaging methods of experimental animals, drug delivery and the like).

The present invention provides the following.

[1] A modified collagen protein expressed in a transformed cell and capable of forming a collagen fiber extracellularly, wherein said transformation is by introduction into said cell of a polynucleotide encoding said modified collagen protein.

[2] The modified collagen protein according to Item [1], wherein said modification is by insertion or addition of a polynucleotide encoding a protein different from said collagen to a nucleotide sequence encoding said collagen.

[3] The modified collagen protein according to Item [1] or [2], wherein said insertion or addition is made at a site within a region corresponding to the N-terminal or C-terminal region of the collagen protein.

[4] The modified collagen protein according to any one of Items [1] to [3], wherein the protein different from collagen is selected from the group consisting of a labeling protein and a therapeutic protein.

[5] The modified collagen protein according to Item [4], wherein the labeling protein is a fluorescent protein (e.g., GFP, iRFP, HaloTag7) or a luminescent protein (e.g., luciferases (e.g., genes: Luc(+), Luc2, CBGluc, CBRluc, ELuc, SLR, SLO, SLG)), and the therapeutic protein is an antibody or a special peptide.

[6] The modified collagen protein according to any one of Items [1] to [5], wherein the collagen is Type V collagen or Type XI collagen.

[7] The modified collagen protein according to Item [6], wherein the collagen is a Type V α1, Type V α3, Type XI α1, or Type XI α2 collagen.

[8] The modified collagen protein according to any one of Items [1] to [7], comprising the amino acid sequence selected from the group consisting of SEQ ID NOs: 2 and 4 or an amino acid sequence having at least 90% identity therewith.

[9] A polynucleotide encoding the modified collagen protein according to any one of Items [1] to [8].

[10] The polynucleotide of Item [9] comprising the nucleotide sequence selected from the group consisting of SEQ ID NO: 1 and SEQ ID NO: 3 or a nucleotide sequence having at least 90% identity therewith.

[11] An expression vector comprising the polynucleotide according to Item [9] or [10].

[12] An expression cell line into which the polynucleotide according to Item [9] or [10], or the expression vector according to Item [11] has been introduced.

[13] A collagen-coated dish coated with the expression cell line according to Item [12].

[14] A drug delivery vehicle comprising the modified collagen protein according to any one of Items [1] to [8] or the polynucleotide according to Item [9] or [10].

[15] A composition comprising the modified collagen protein according to any one of Items [1] to [8] or the polynucleotide according to Item [9] or [10].

[16] A model animal into which the polynucleotide according to Item [9] or [10], the expression vector according to Item [11], the expression cell line according to Item [12], the vehicle according to Item [14], or the composition according to Item [15] has been introduced.

[17] The model animal according to Item [16], wherein the model animal is a mouse.

[18] A method of forming a collagen fiber comprising a modified collagen protein outside a cell transduced with a gene encoding said modified collagen, wherein said method comprising introducing the polynucleotide of Item [9] or [10] into said cell.

[19] The method according to Item [18], comprising culturing the transduced cells in vitro under stress.

[20] The method according to Item [18] or [19], further comprising the step of forming the collagen fiber comprising said modified collagen protein in a model animal.

[21] The method according to any one of Items [18] to [20], wherein the modified collagen protein has been modified by insertion or addition of a labeling protein, and wherein said method further comprises visualizing or imaging to detect the labeling.

[22] The method according to any one of Items [18] to [21], wherein the modified collagen is Type V collagen α1 in which a labeling protein is inserted at a site between the N-terminal domain and the hinge region.

[23] A method for screening for an inhibitor of collagen secretion and/or collagen fiber formation, comprising the steps of:

culturing the expression cell line according to Item [12] under stress conditions in vitro, wherein the modified collagen protein has been modified by insertion or addition of a labeling protein;

adding to said culture a candidate agent of said inhibitor before the culturing under said stress conditions;

observing said cell for collagen secretion and/or collagen fiber formation outside of said cell after said addition of said candidate substance in said culture; and selecting as said inhibitor said candidate agent having an effect of reducing said collagen secretion and/or collagen fiber formation as compared to the absence of said addition of said candidate substance.

[24] The method according to Item [23], wherein said selecting comprises visualizing or imaging to detect the labeling.

Effect of the Invention

The present invention provides an advantage of being able to modify collagen proteins in a manner that does not impair or is unlikely to impair the properties of the collagen fibers.

In accordance with the present invention, there is provided a modified collagen protein which is capable of being secreted out of a transformed cell. According to the present invention, it is possible to produce a modified collagen protein capable of forming a collagen fiber extracellularly.

The technique for modifying collagen proteins according to the present invention may allow the labeling of collagen fibers with labeled proteins and thereby visualization of the collagen fibers.

The method of labeling collagen fibers according to the present invention allows non-invasive imaging in vivo without dissecting experimental animals. Thus, there is provided an advantage that the present invention can be a probe that monitors fiber formation in real-time.

EMBODIMENTS FOR CARRYING OUT THE INVENTION

Figure 1:
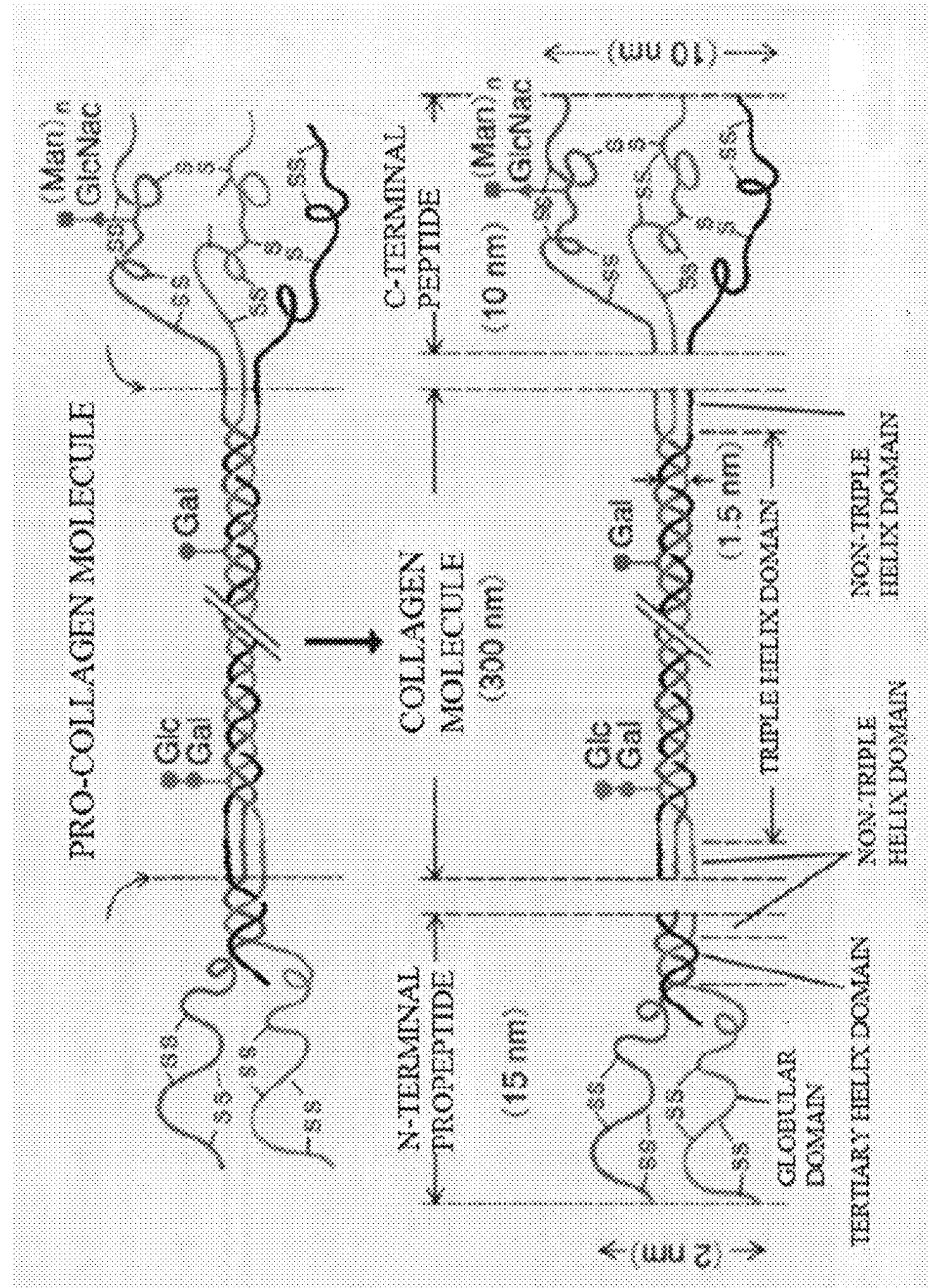
FIG. 1 shows the structure of a collagen molecule according to the prior art.
Figure 2:
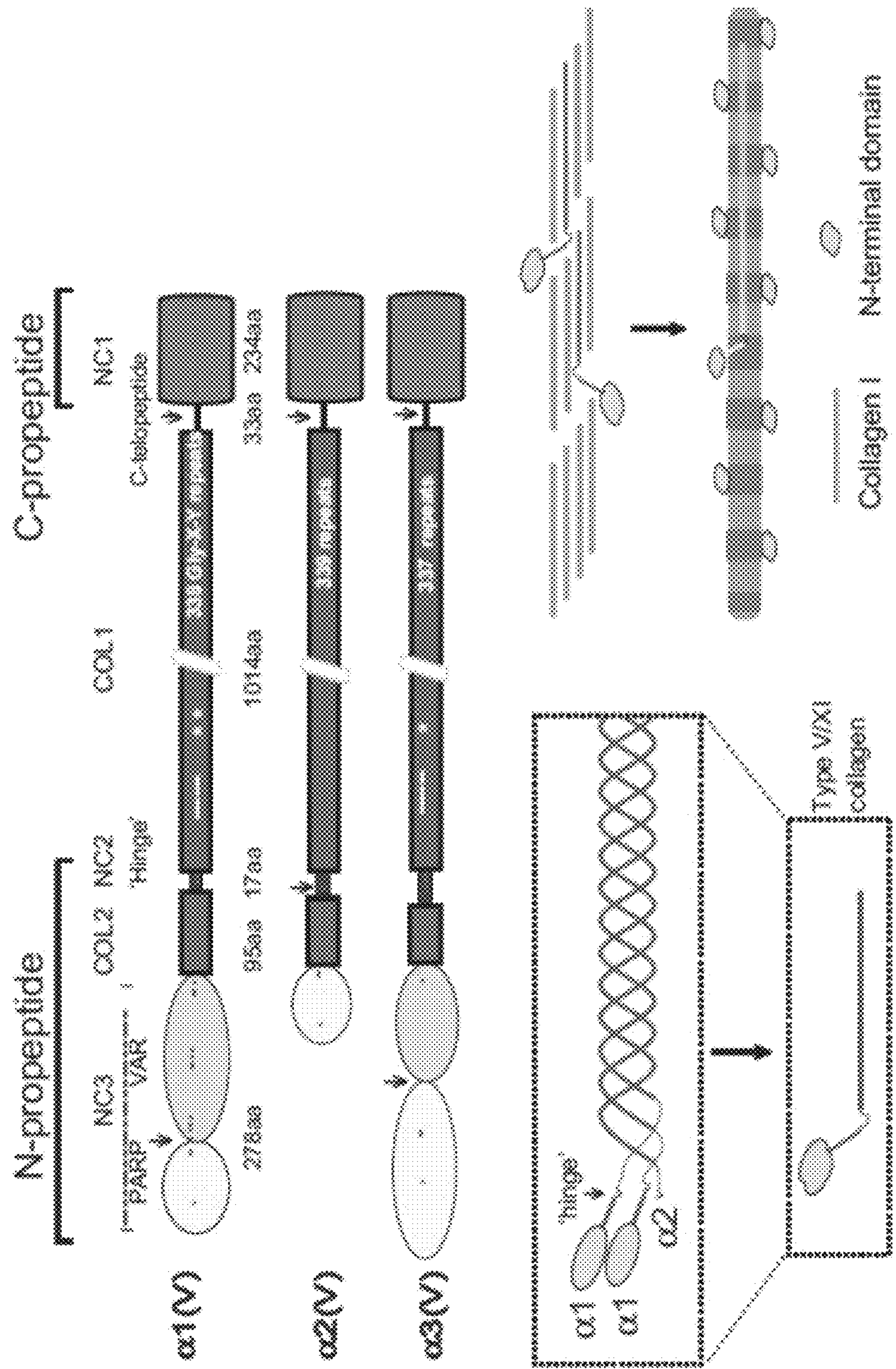
FIG. 2 shows the structure of a Type V collagen molecule according to the prior art.
Figure 3:
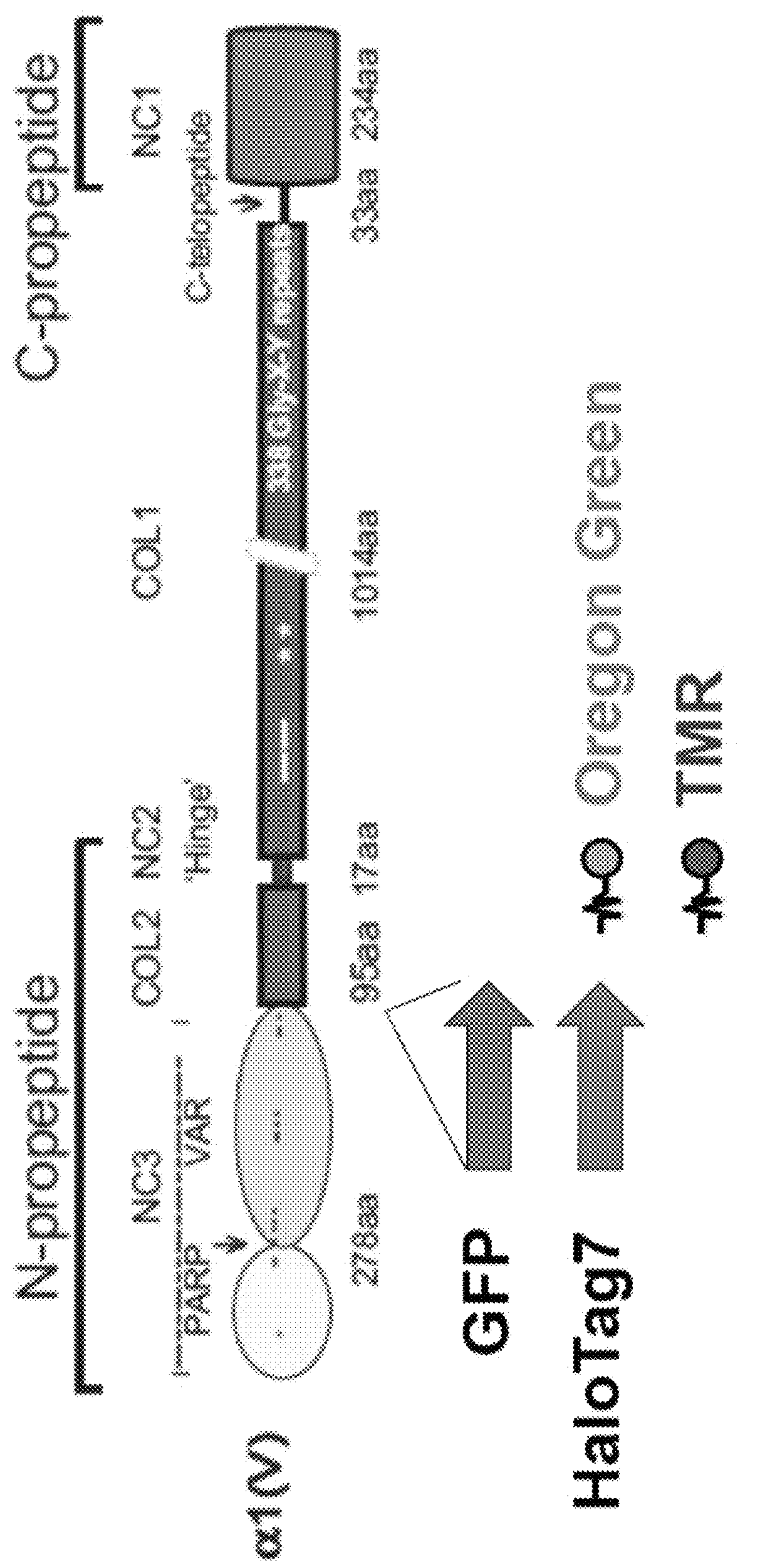
FIG. 3 is a conceptual diagram illustrating the introduction of an imaging protein (e.g., a fluorescent protein (GFP, iRFP), HaloTag protein) between the N-terminal domain and the hinge portion of Type V collagen α1.

"Collagen" and "collagen protein" are used herein as being synonymous.

The collagen used according to the purpose of the present invention is preferably collagen in which at least one of the N-terminus and the C-terminus (i.e., a portion which is arranged toward outside the fiber at the time of formation of the collagen fiber and to which the foreign protein or the like is easily added) is not cut or removed when secreted to the outside of the cell. Examples of such collagens include Type V collagen and Type XI collagen. As Type V collagen, Type V al and Type V a3 collagen are preferable, and as Type XI collagen, Type XI al and Type XI a2 collagen are preferable. The amino acid sequences of these collagens and the nucleotide sequences encoding them are available from well-known, commonly accessible databases.

As used herein, "modification" of a collagen protein means primarily an insertion or addition of a foreign protein to native collagen, of which, in particular, the insertion or addition of such foreign protein does not substantially impair the function of the original collagen protein (e.g., the ability to form collagen fibers). Insertion or addition of such foreign proteins into native collagen can be accomplished by conventional gene transfer techniques well known to those skilled in the art. The terms "insertion" and "addition" are used interchangeably herein to refer to the insertion or addition of a foreign amino acid sequence to a collagen protein, or the insertion or addition of a foreign nucleotide sequence to a nucleotide sequence encoding the collagen protein. As used herein, "transformation" of a cell is used synonymously with "transfection" to mean the introduction of genes or DNAs from outside the cell, altering the genetic properties of the cell, or manipulation thereof.

Preferred sites of "modification" of collagen proteins according to the purposes of the present invention are those sites where collagen proteins are less likely to have a substantial effect on fiber formation when forming fibers, and preferably, for example, the N-terminal and C-terminal regions of collagen proteins that are arranged toward outside the fibers when forming collagen fibers as described above and to which foreign proteins or the like are likely to be easily added.

In the exemplary embodiment described below, an example has been presented in which the foreign protein has been inserted into a site within the region between the N-terminal domain (N-terminal propeptide) and the hinge portion of Type V α1 collagen (a site between positions 1750 and 1751 in the nucleotide sequence (XM_006497644) encoding Type Vα1 collagen (corresponding to a site between the 443 and 444 amino acid residues within the amino acid sequence (XP_006497707) that is coded by the nucleotide sequence). Besides, examples of collagen proteins having a preferable site for such modification include Type V α3 collagen, Type XI α1 and Type XI α2 collagens described above. Suitable sites for the insertion of foreign proteins in these collagens may be derived by those skilled in the art without undue experimentation from the guidance herein and the common general knowledge in the art.

The "foreign proteins" described above suitable for the present purposes include labeling proteins such as fluorescent proteins (e.g., GFP, iRFP, HaloTag7), luminescent proteins such as luciferases (e.g., Luc(+), Luc2, CBGluc, CBRluc, ELuc, SLR, SLO, SLG (Akimoto et al, Biophysics 49(2), 070-074 (2009); incorporated herein by reference in its entirety)), proteins used for the treatment of diseases (e.g., antibodies) or peptides (e.g., special peptides synthesized so as not to be easily degraded in vivo). The above-mentioned fluorescent proteins or luminescent proteins are commercially available, for example, and are thus available to a person skilled in the art. References on methods of introducing luminescent proteins include Takai et al., PNAS, 112(14), 4352-4356 (2015); and Suzuki et al., Nature Communications 7:13718 DOI:10.1038. (2016), which are incorporated herein by reference in its entirety. For visualization or imaging techniques for the detection of labels such as fluorescent proteins, luminescent proteins, etc., sufficient guidance can be obtained from the examples described hereinbelow, the references cited above, or manufacturers' instructions, etc., in the case of those commercially available.

According to the purposes of the present invention, cells that can be used to produce a modified collagen protein include any animal cells. Examples of such cells include, but are not limited to, mouse MC3T3-E1 cells (originally collagen-producing cells), or mouse Balb3T3 cells used in the examples described below. Examples of an "animal" of the animal cells include, but are not limited to, mouse, rat, guinea pig, gerbil, hamster, ferret, rabbit, dog, minipig and the like.

The term "identity" is used herein to distinguish it from "homology". For example, when referring to homology between amino acid sequences, amino acids with the same properties (e.g., glutamic acid and aspartic acid) are categorized as a single group, but they are distinguished when considering identity. That is, identity refers to consistency. The identity of amino acid and nucleotide sequences can be determined using an algorithmic BLAST (Proc. Natl. Acad by Karlin and Altull. Sci. USA, 87, 2264-2268, 1990; Proc. Natl. Acad. Sci. USA, 90, 5873, 1993). Programs called BLASTN and BLASTX based on BLAST algorithms have been developed (Altschul S F, et al: J Mol Biol 215: 403, 1990). When the base sequence is analyzed using BLASTN, the parameters are, for example, score=100 and wordlength=12. When the amino acid sequence is analyzed using BLASTX, the parameters are, for example, score=50 and wordlength=3. When using BLAST and Gapped BLAST programs, the default parameters of the respective programs can be used.

In an advanced embodiment of the invention, cells transformed to express the modified collagen protein are stressed to promote the secretion of the modified collagen protein out of the cells. "Stress" conditions imparted to cells transgenic to express modified collagen proteins according to the purposes of the present invention include, but are not limited to, filling up a container with culture medium, changing gravity, vibration, centrifugal force, etc., provided that they have the effect of changing the morphology of the cells.

BRIEF DESCRIPTION OF THE SEQUENCES

Figure 10:
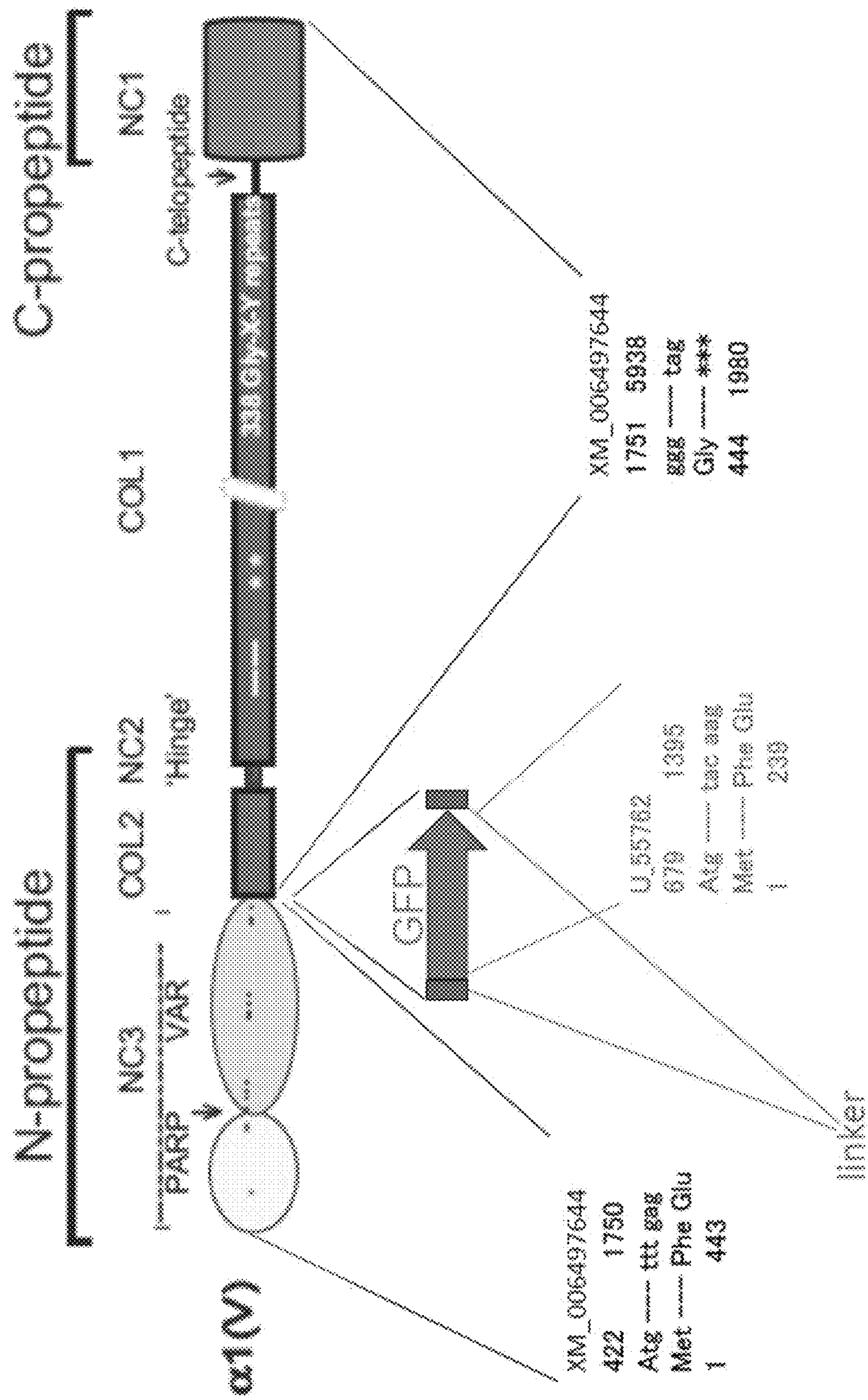
FIG. 10 is a schematic diagram showing the configuration and sequence of GFP inserted Type V collagen al according to the present embodiment. SEQ ID NOS. 21 and 22.

SEQ ID NO: 1 shows the nucleotide sequence encoding GFP-inserted Type V collagen α1 shown schematically in FIG. 10.

SEQ ID NO: 2 shows the amino acid sequence of GFP-inserted Type V collagen α1 shown schematically in FIG. 10.

Figure 11:
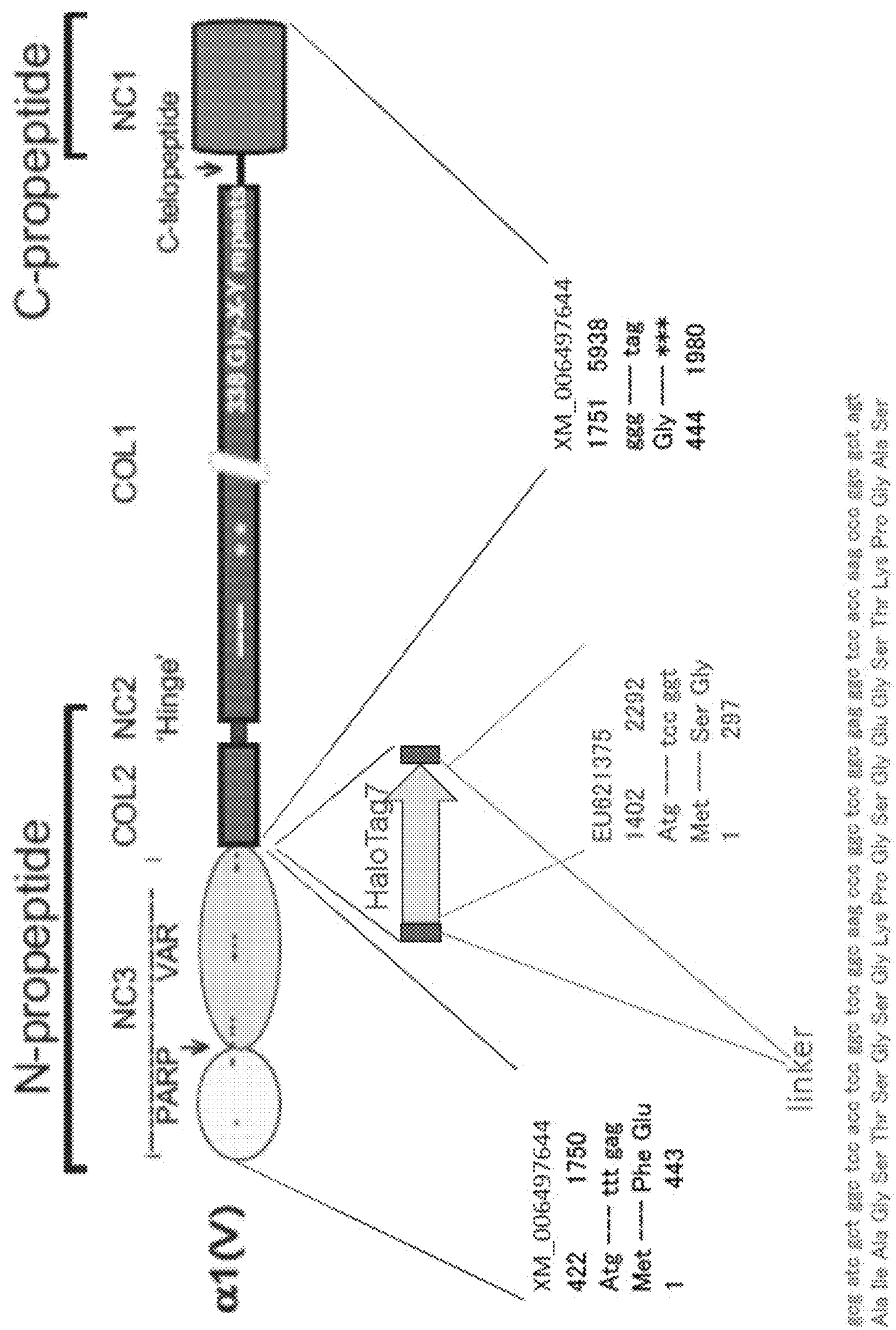
FIG. 11 is a schematic diagram showing the configuration and sequence of HaloTag7 inserted Type V collagen al according to the present embodiment. SEQ ID NOS. 21 and 22.

SEQ ID NO: 3 shows the nucleotide sequence encoding HaloTag7-inserted Type V collagen α1 shown schematically in FIG. 11.

SEQ ID NO: 4 shows the amino acid sequence of HaloTag7-inserted Type V collagen α1 shown schematically in FIG. 11.

SEQ ID NO: 5 shows the nucleotide sequence of the plasmid vector pEB6CAGcol5α1-EGFP according to the working example of the present invention.

SEQ ID NO: 6 shows the nucleotide sequence of the plasmid vector pEB6CAGcol5α1-Halo7 according to the working example of the present invention.

SEQ ID NO: 7 shows the nucleotide sequence of the linker used in making the modified collagen protein according to the examples of the present invention (see FIGS. 10 and 11).

SEQ ID NO: 8 shows the amino acid sequence encoded by the nucleotide sequence of SEQ ID NO: 7.

SEQ ID NO: 9 shows the nucleotide sequence (XM_006497644) that encodes mouse-derived Type V collagen α1.

SEQ ID NO: 10 shows the amino acid sequence (XP_006497707) of mouse-derived Type V collagen α1.

SEQ ID NO: 11 shows the nucleotide sequence (XM_017313471) that encodes mouse-derived Type V collagen α3.

SEQ ID NO: 12 shows the amino acid sequence (XP_017168960) of mouse-derived Type V collagen α3.

SEQ ID NO: 13 shows the nucleotide sequence (NM_007729) encoding mouse-derived Type XI collagen α1.

SEQ ID NO: 14 shows the amino acid sequence (NP_031755) of mouse-derived Type XI collagen α1.

SEQ ID NO: 15 shows the nucleotide sequence (NM_001317722) that encodes mouse-derived Type XI collagen α2.

SEQ ID NO: 16 shows the amino acid sequence (NP_001304651) of mouse-derived Type XI collagen α2.

SEQ ID NO: 17 shows the nucleotide sequence (U55762) of the cloning vector pEGFP-N1 used in making the modified collagen protein according to the working example of the present invention (see FIG. 10).

SEQ ID NO: 18 shows the amino acid sequence (AAB02574) of the enhanced green fluorescent protein encoded by the cloning vector pEGFP-N1 of SEQ ID NO: 17.

SEQ ID NO: 19 shows the nucleotide sequence (EU621375) of CMV Flexi Vector pFN21K (HaloTag 7) used in making the modified collagen protein according to the working example of the present invention (see FIG. 11).

SEQ ID NO: 20 shows the amino acid sequence (ACF22985) of the kanamycin-resistant protein encoded by CMV Flexi Vector pFN21K (HaloTag 7) of SEQ ID NO: 19.

The following examples illustrate the present invention, but the scope of the present invention is not intended to be limit to these examples.

EXAMPLES

Materials and Methods

The materials and methods used in the examples below are as follows.

1. Cultivation of Cells

The cells used are a mouse-derived osteoblast cell line, MC3T3-E1, and a mouse fibroblast cell Balb3T3.

Normal cultivation was performed using the following materials. Cultivations using MC3T3-E1 and Balb3T3, respectively, were performed in αMEM medium containing 10% serum, and in MEM medium containing 10% serum, at 37° C. and 5% $CO_2$.

Serum: Fetal bovine serum (Gibco)

Medium: Minimum Essential Medium Alpha (Gibco)

Medium: Minimum Essential Medium (Gibco)

Dish for culturing cells: Cell culture dish 60×15 mm (Falcon)

The following flasks were filled with medium for shaking culture.

Cell-culture flasks: 25 mL (Falcon) of Cell culture flask (12.5 $cm^2$ slant neck/plug seal)

The shaking culture was performed using a mini-shaker SHM-2002 (LMS) at a shaking angle of 7° and a rotational speed of 20 rpm using a sunflower shaking method.

2. Gene Transfer

For vector construction, the pEB6CAG vector developed in this laboratory was used as a basic skeleton. Each of GFP and HaloTag®7 (Promega) was inserted between the N-terminal globular domain and the hinge region of cloned Type V collagen, and the following vectors were generated (see FIGS. 3, 9, 10, and 11).

pEB 6CAGCol5α1-GFP pEB 6CAGCol5α1-Halo7

MC3T3-E1 cell, a cell line derived from a mouse skull, and mouse fibroblast cell line Balb3T3 were used in this study. Gene transfer was carried out by the lipofection method, and ScreenFect™ A (Wako Junyaku, Inc.) was used as a reagent. Thirty-six hours after the gene transfer, cells were treated with 0.05% Trypsin, 0.02% EDTA-2Na in PBS(−) solution (Trypsin solution), then passaged in a 60-mm dish, and selected for 5 days with αMEM medium or MEM medium containing a final concentration of 1.5 μg/ml Geneticin (G418). Formed colonies were collected, and after continuing the culturing, clones with high luminescence intensity were selected.

3. Stain with HaloTag Ligands

The following three dyes were added to 0.1 μM to MC3T3-E1 cells to which the pEB6CAGCol5α1-Halo7 had been introduced, stained for 1 hour, washed with medium to remove the dyes, and after 1 hour of decolorization, the cells were observed for fluorescent light.

HaloTag-OregonGreen (membrane permeable, green)
HaloTag-TMR (membrane permeable, red)
HaloTag-Alexa488 (membrane impermeable, green)

4. Imaging of Cells

OLYMPUS LX73 was used for fluorescent microscopy. The following filter sets were used for fluorescence imaging.

Green Fluorescence: U-EGFP (OLYMPUS), Ex: 470/20, Em: 518/45

Red fluorescence: BrightLine®SpGold-B-000-ZERO (Semrock), Ex: 534/20, Em: 572/28

Near Infrared Fluorescence: BrightLine®Cy5.5-B-000 (Semrock), Ex: 655/40, Em: 716/40

Super-resolution microscopy was performed using a Zeiss LSM880 Airscan with cells in which nuclei were counter-stained with Hoechst33342.

5. Cell Transplantation

As for collagen-probe-stable expression strains of MC3T3-E1 and Balb3T3, $1\times10^6$ cells of were suspended in 50 μl of PBS(−). MC3T3-E1 cells were implanted subcutaneously in the back of C57BL/6 albino mouse, and Balb3T3 cells were implanted subcutaneously in the back of Balb/c mouse. Two weeks later, the skin was dissected and photographed using a multi-spectral CCD-camera Nuance (PerkinElmer placed on a stereomicroscope MVX (OLYMPUS) at 2.5× magnification. In the case of GFP insertion, the cells were observed as they were, and in the case of HaloTag insertion, 50 μl of a solution obtained by diluting Stella700HaloTag ligands with PBS(−) to 0.5 μM was administered to the cell transplantation site, and the cells were stained for 1 hour and then photographed. The following filters were used for fluorescence imaging.

Green Fluorescence: U-FGFP (OLYMPUS), Ex: 470/20, Em: 518/45

Near-Infrared Fluorescence: BrightLine®Cy5.5-B-000 (Semrock), Ex: 655/40, Em: 716/40

Three weeks after the transplantation, a skin section containing fluorescence was excised and fixed, and sections were made in the direction of cutting the fluorescence fibers, and the accumulation of collagen fibers was detected by H&E staining, Masson trichrome staining, and Elastica-One Gieson staining

Example 1

Expression of GFP-Inserted Type V Collagen-α1 in Murine MC3T3-E1 Cells

Figure 4:
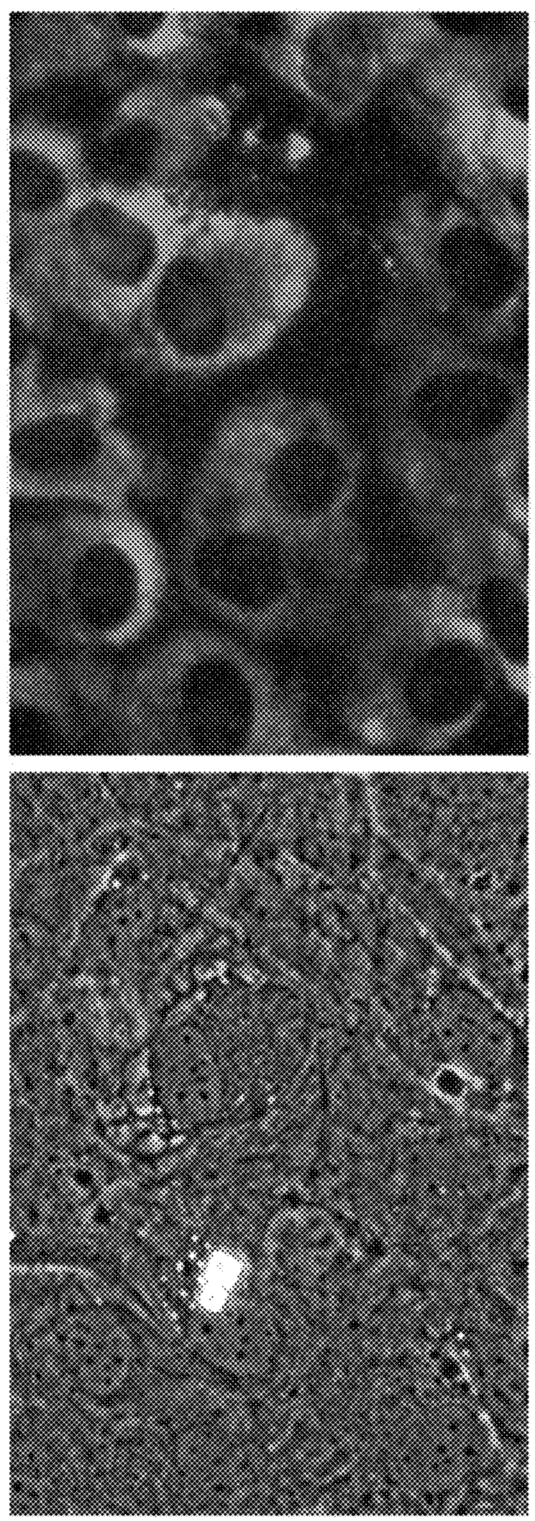
FIG. 4 is a diagram of analysis in which GFP-inserted Type V collagen α1 had been introduced into and expressed in a mouse osteoblast MC3T3-E1, which is a collagen-producing cell, and analyzed by a flow cytometer and a fluorescent microscope.

Considering that a special intracellular transport system is considered to be required for collagen, GFP-inserted Type V collagen α1 was introduced and expressed using murine MC3T3-E1 cells which had been reported to produce collagen. Fluorescence microscopy revealed granular green fluorescence in the cytoplasm, probably transported by membrane vesicles, but the Golgi bodies were dark missing (FIG. 4). Thus, it was presumed that with the normal culture method, collagen protein was not correctly transported and secreted.

Example 2

Expression of GFP-Inserted Type V Collagen α1 in Murine MC3T3-E1 Cells Under Stress (1)

Figure 5:
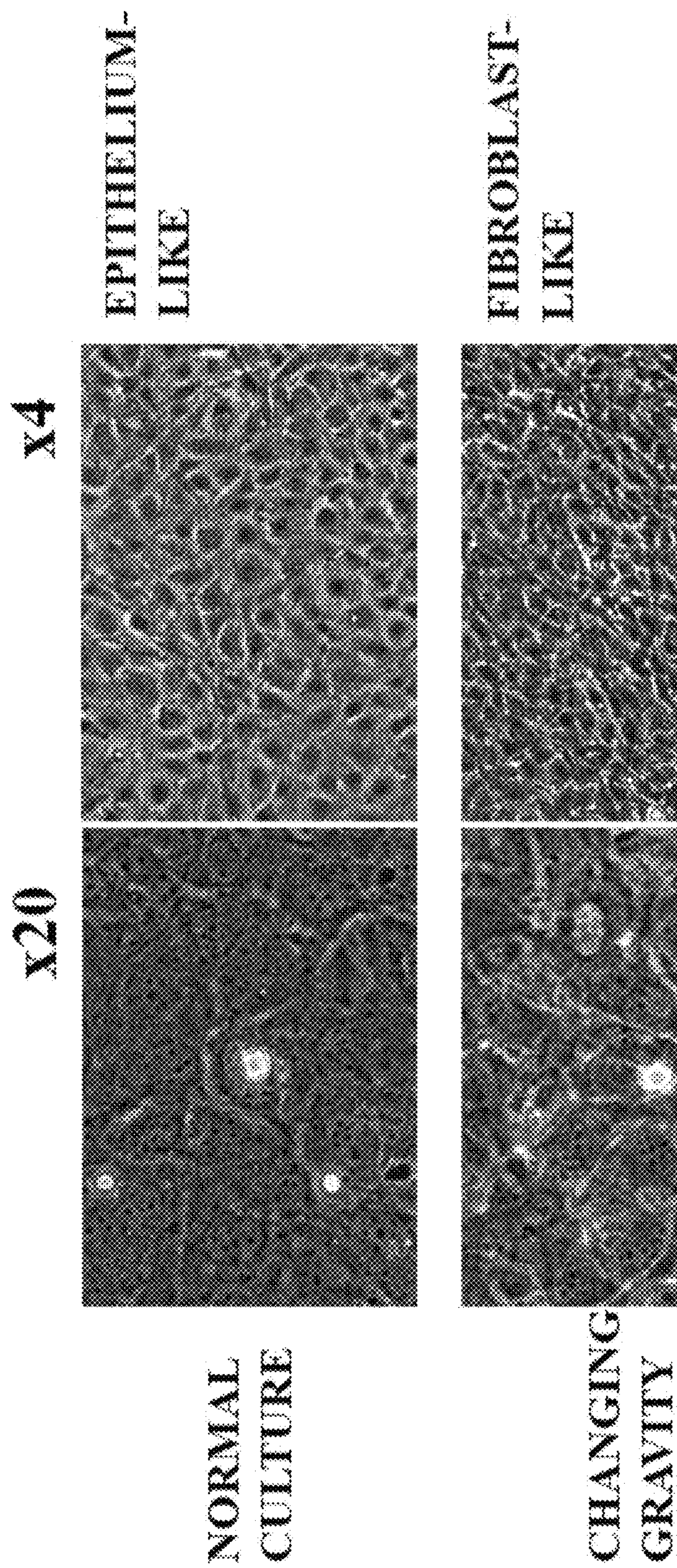
FIG. 5 shows a comparison of the microscopic images of cultures of mouse osteoblasts MC3T3-E1 between a normal culture and that under gravitational stress applied using Zeromo®.

To examine an improvement of the cultivation method, the morphology of MC3T3-E1 cells was observed while the flasks were rotated and subjected to the stress of gravitational change using Zeromo® manufactured by Kitagawa Corporation. As shown in FIG. 5, the normal culture showed a thin and spread epithelium-like morphology, whereas, after 3 days of gravitational stress, the cells were finely folded and transformed into a dense fibroblast-like morphology (FIG. 5).

Example 3

Expression of GFP-Inserted Type V Collagen α1 in Murine MC3T3-E1 Cells Under Stress (2)

Figure 6:
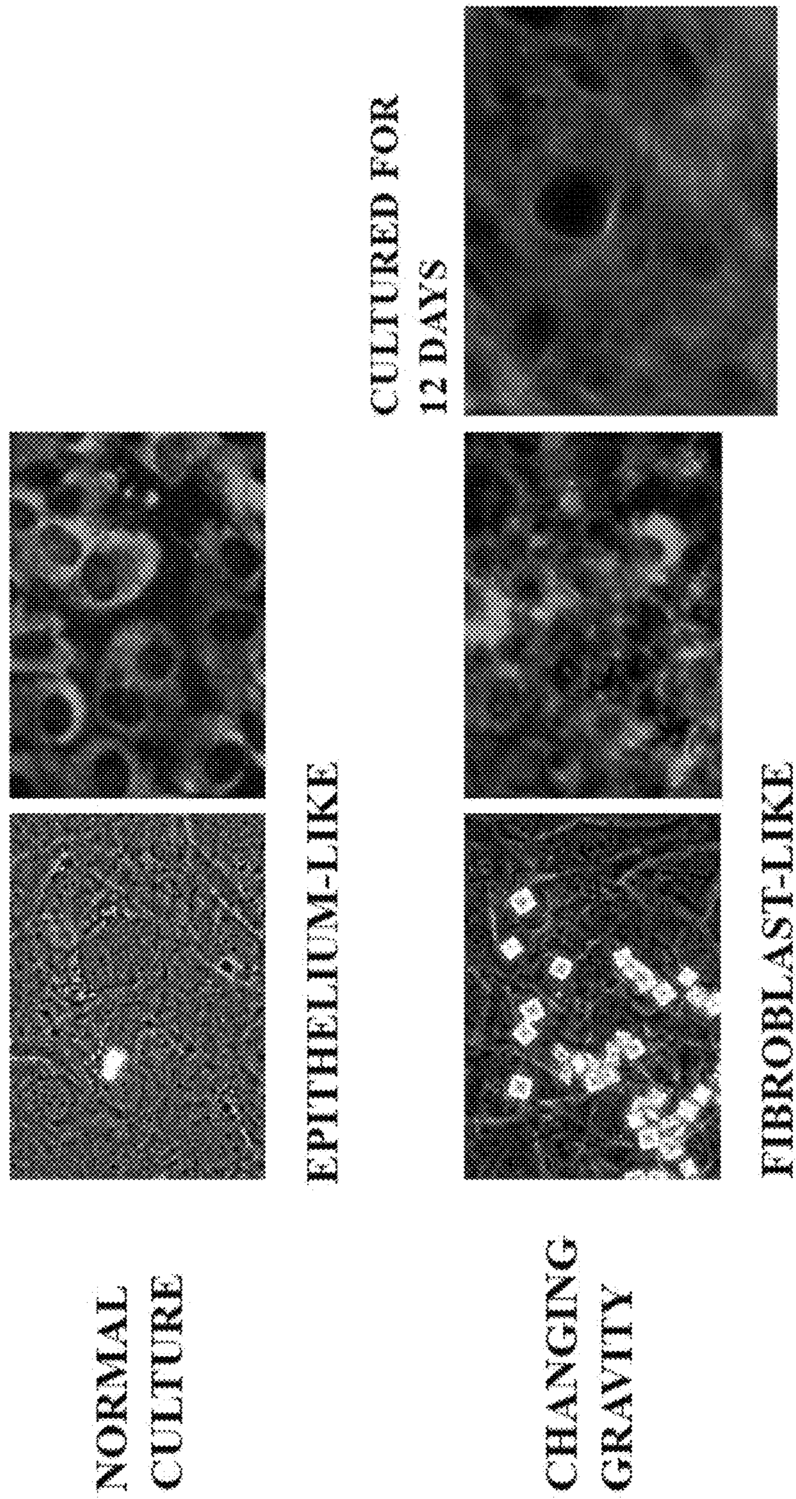
FIG. 6 shows a comparison of the microscopic images of cultures of mouse osteoblasts MC3T3-E1, into which GFP-inserted Type V collagen α1 had been introduced and expressed, between a normal culture and that under the gravitational stress.

When MC3T3-E1 cells into which the GFP-inserted Type V collagen α1 was introduced and expressed were subjected to gravitational stress by Zeromo® as in FIG. 5, not only the morphology of the cells changed from epithelial to fibroblast-like but also the appearance of many crystals was observed, and a partial change to fibroid was also observed in the fluorescent image on the third day. Continued Zeromo® culture resulted in a complete change to normal collagen-like fibrosis at 12 days (FIG. 6).

Example 4

Comparison and Study of Stress Conditions

Figure 7:
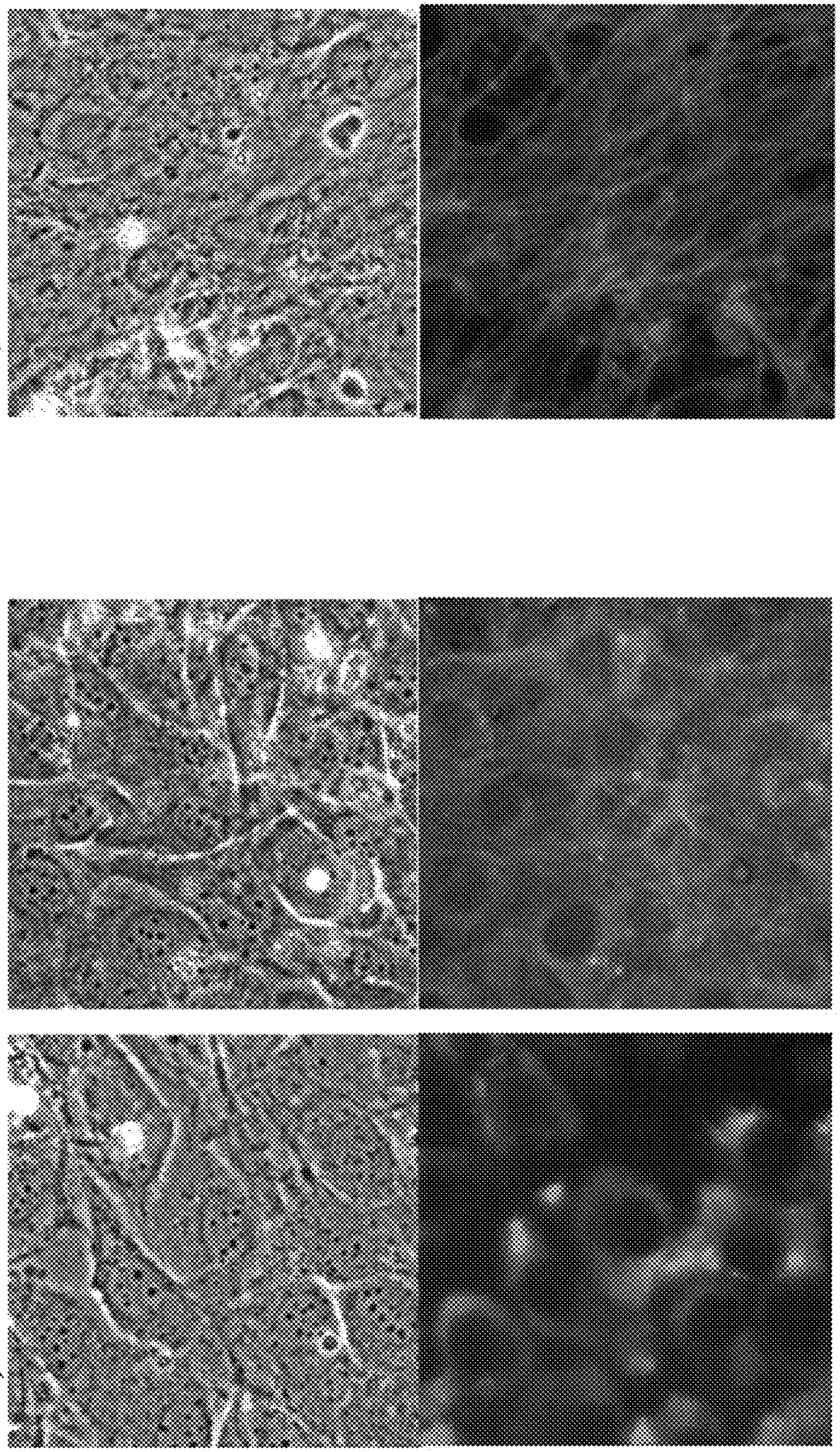
FIG. 7 shows FIG. 7, panels A-C, show a comparison of microscopic images of cultures of mouse osteoblasts MC3T3-E1, into which GFP-inserted Type V collagen α1 or HaloTag7-inserted Type V collagen α1 had been introduced and expressed, between a normal culture and that under gravitational stress applied using a common shaker.

Whether the rotation using the Zeromo® is necessary or a simpler shaking is sufficient for the gravitational stress was investigated. A) When MC3T3-E1 cells into which GFP-inserted Type V collagen al had been introduced and expressed were subjected to static culture in a normal manner, the cells were epithelial and not secreted (FIG. 7, panel A). When the cells were subjected to shaking culture, the morphology changed like fibroblasts, and the secreted collagen fibers were visualized as fluorescence (FIG. 7, panel B). When the cells into which HaloTag7-inserted Type V collagen al was introduced and expressed were subjected to shaking culture, and stained with TMR-HaloTag ligands, collagen fiber images were visualized in the same manner as in the case of GFP (FIG. 7, panel C).

Example 5

Extracellular Secretion of Collagen Fibers

Figure 8:
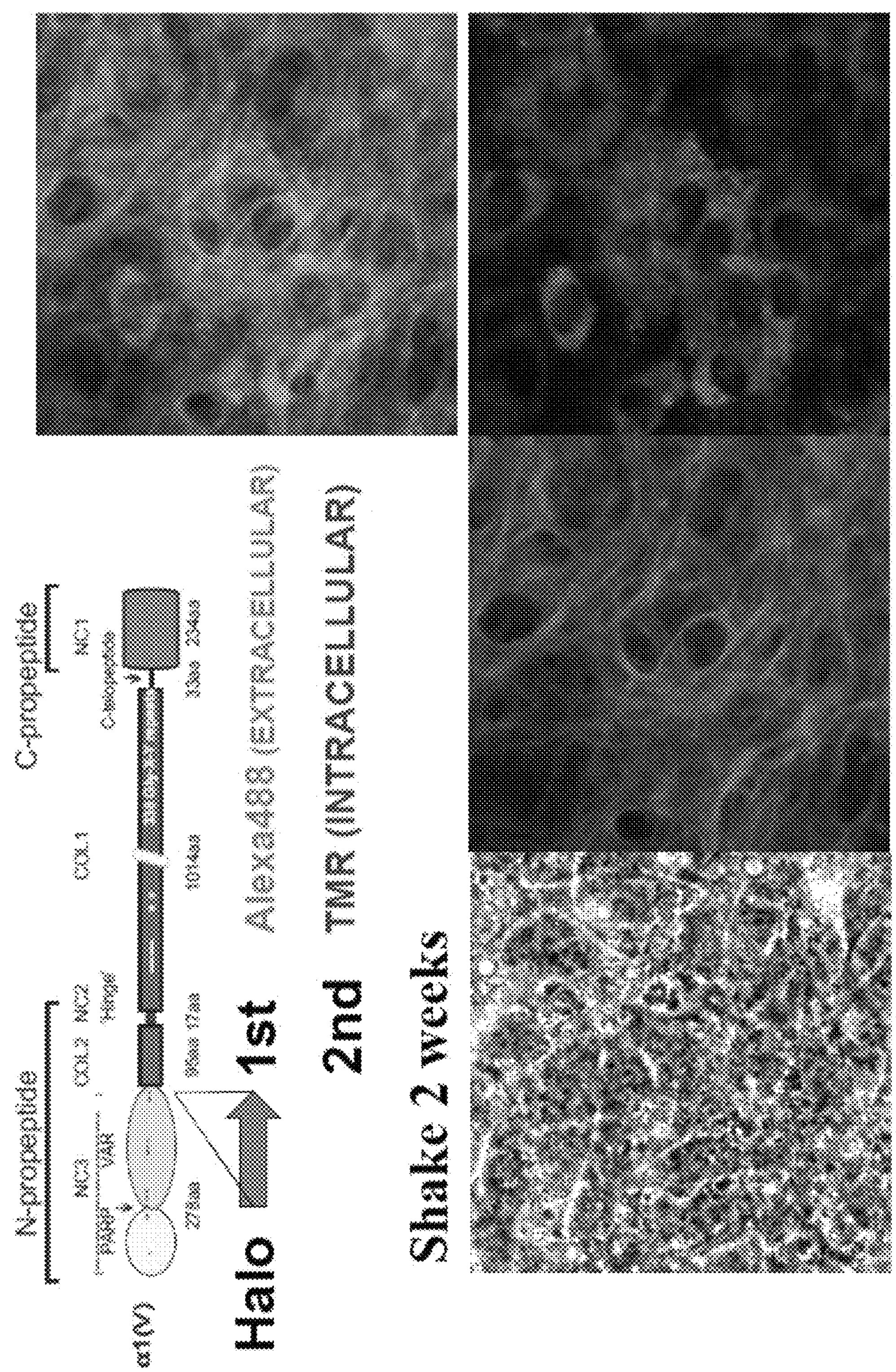
FIG. 8 shows microscopic images of a mouse osteoblast MC3T3-E1 into which a HaloTag7-inserted Type V collagen α1 had been introduced and expressed, and which had been cultivated under the gravitational stress applied using a common shaker, and then stained in two stages with a cell membrane-impermeable Alexa488 ligand and a cell membrane permeable TMR ligand.
Figure 9:
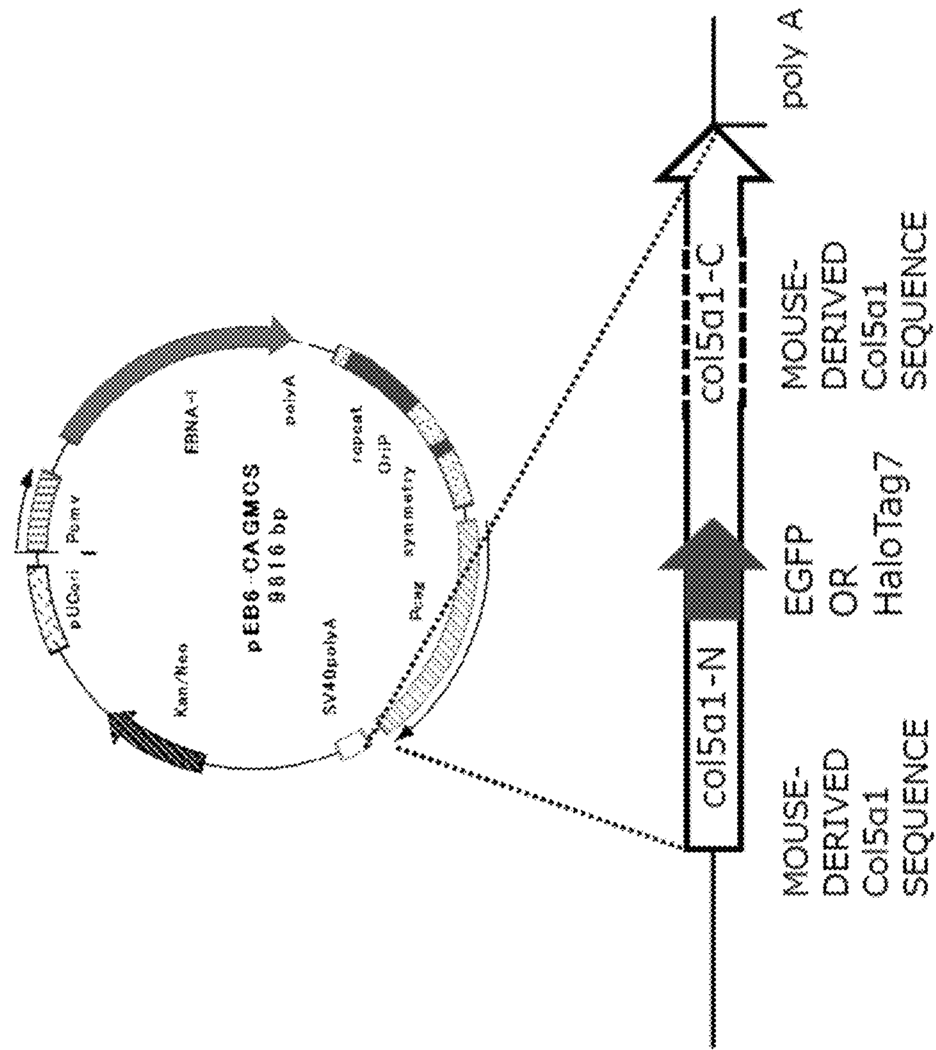
FIG. 9 is a schematic diagram showing the vector used to express GFP-inserted Type V collagen α1 or HaloTag7-inserted Type V collagen α1.

To confirm that the fibers seen in FIG. 7 were secreted extracellularly, the cells were subjected to a two-step staining, i.e., first stained for 1 hour with Alexa488-HaloTag ligand, which is not membrane permeable and can only stain extracellular proteins, followed by staining with TMR-HaloTag ligand, which is membrane permeable and can stain intracellularly for an additional hour. It was shown that the green fluorescence image (FIG. 8; the center of the bottom column) visualized the fibers secreted outside the cell, and the red fluorescence image (FIG. 8; right of the bottom column) visualized proteins which were still in transport within the cell, the image of which is similar to the fluorescence image of FIG. 4 where proteins were not secreted (FIG. 8).

Example 6

Figure 12:
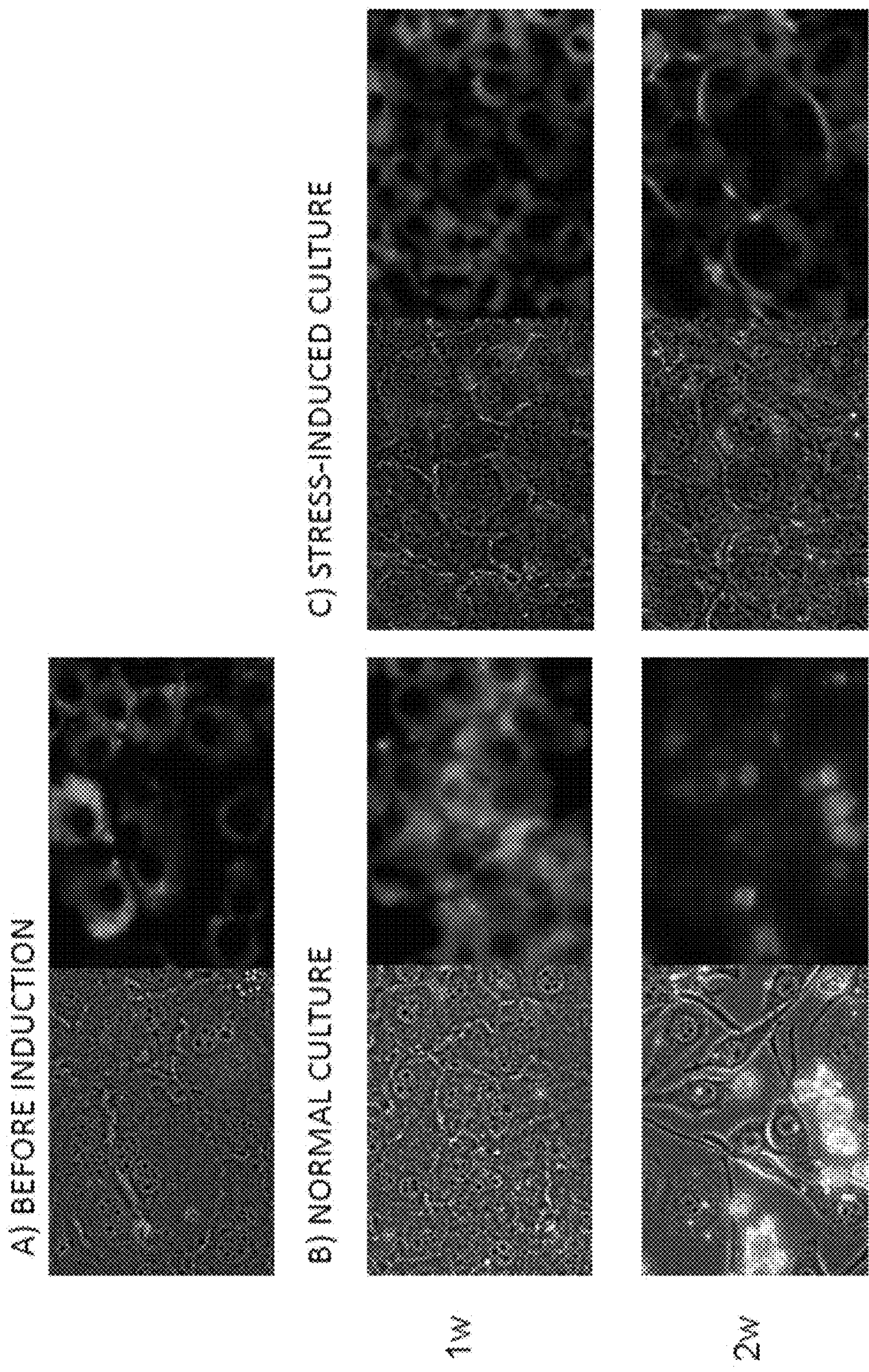
FIG. 12 shows FIG. 12, panels A-C, show a comparison of microscopic images of cultures of mouse fibroblasts Balb3T3, into which GFP-inserted Type V collagen α1 had been introduced and expressed, between a normal culture and that under the gravitational stress applied.

Expression of GFP-Inserted Type V Collagen-α1 in Murine Balb3T3 Cells Under Stress To assess whether the GFP-inserted V collagen al probes also function in other cells, a Balb3T3 cell line in which GFP-inserted Type V collagen al was introduced and expressed was established and analyzed. During normal growth culture, granular fluorescence was only detected in the cytoplasm and secretion did not occur (FIG. 12, panel A). Secretion did not occur even if the culture was kept stationary and normal culture was continued, and a considerable amount of cells died in the second week (FIG. 12, panel B). At 2 weeks during stress-induced culture, collagen fibers secreted were visualized as fluorescence (FIG. 12, panel C).

Example 7

Figure 13:
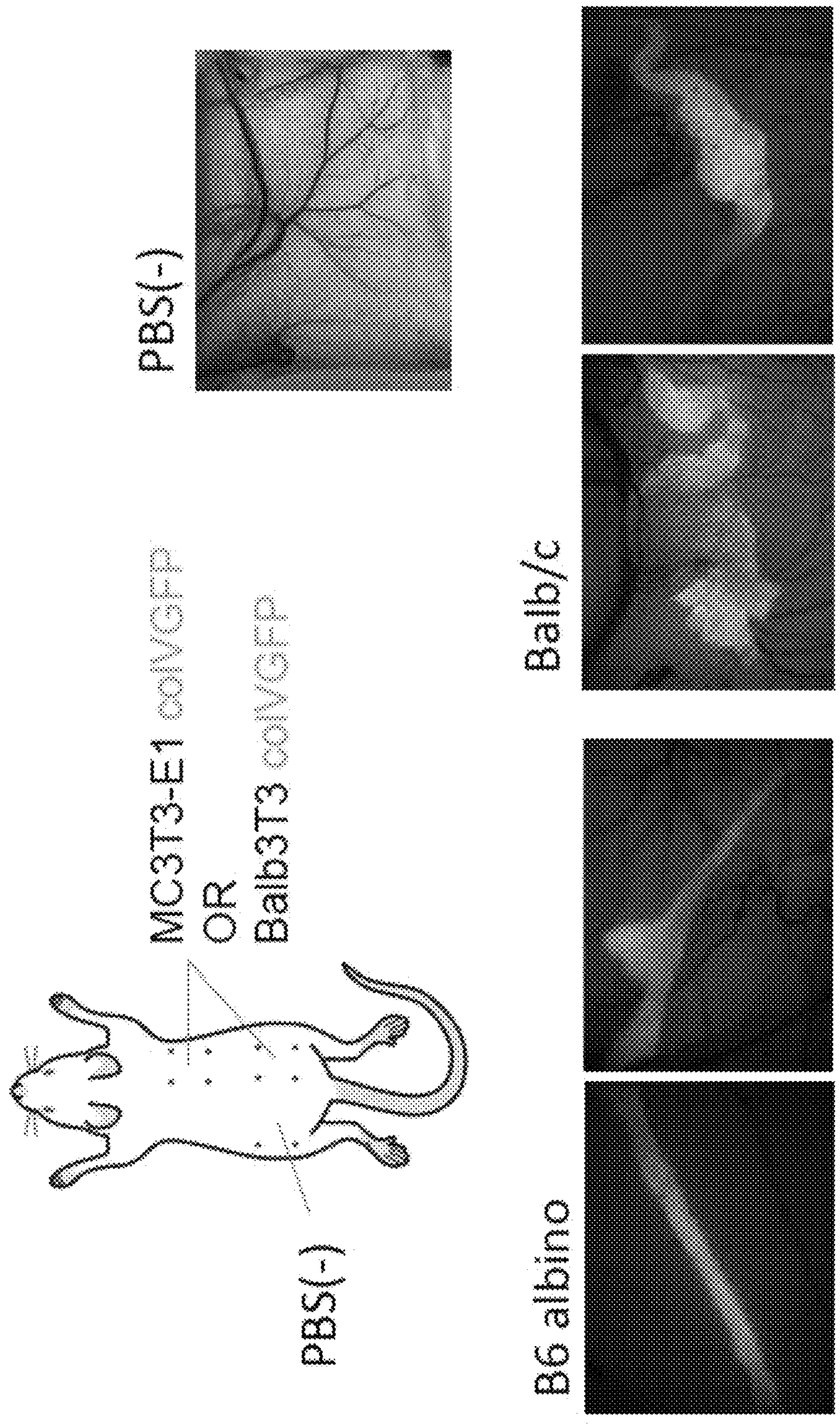
FIG. 13 shows a comparison of microscopic images of a mouse osteoblast MC3T3-E1 and a mouse fibroblast Balb3T3, into which GFP-inserted Type V collagen α1 had been introduced and expressed, and implanted subcutaneously in the back of C57BL/6 and Balb/c mice, respectively, for 2 weeks.

Murine Subcutaneous Implantation of GFP-Inserted Type V Collagen-α1-Expressing Cells $1\times10^6$ cells of collagen-probe-stable expression strains of MC3T3-E1 and Balb3T3 were suspended in 50 μl of PBS (−), and MC3T3-E1 cells were implanted subcutaneously in the back of C57BL/6 albino mouse and Balb3T3 cells were implanted subcutaneously in the back of Balb/c mouse. Two weeks later, the skin was turned inside-out and fluorography revealed the formation of collagen fiber-like clumps in all mice that were illuminated by GFP fluorescence. These were not seen at the site where only PBS(−) was injected (FIG. 13).

Example 8

Figure 14:
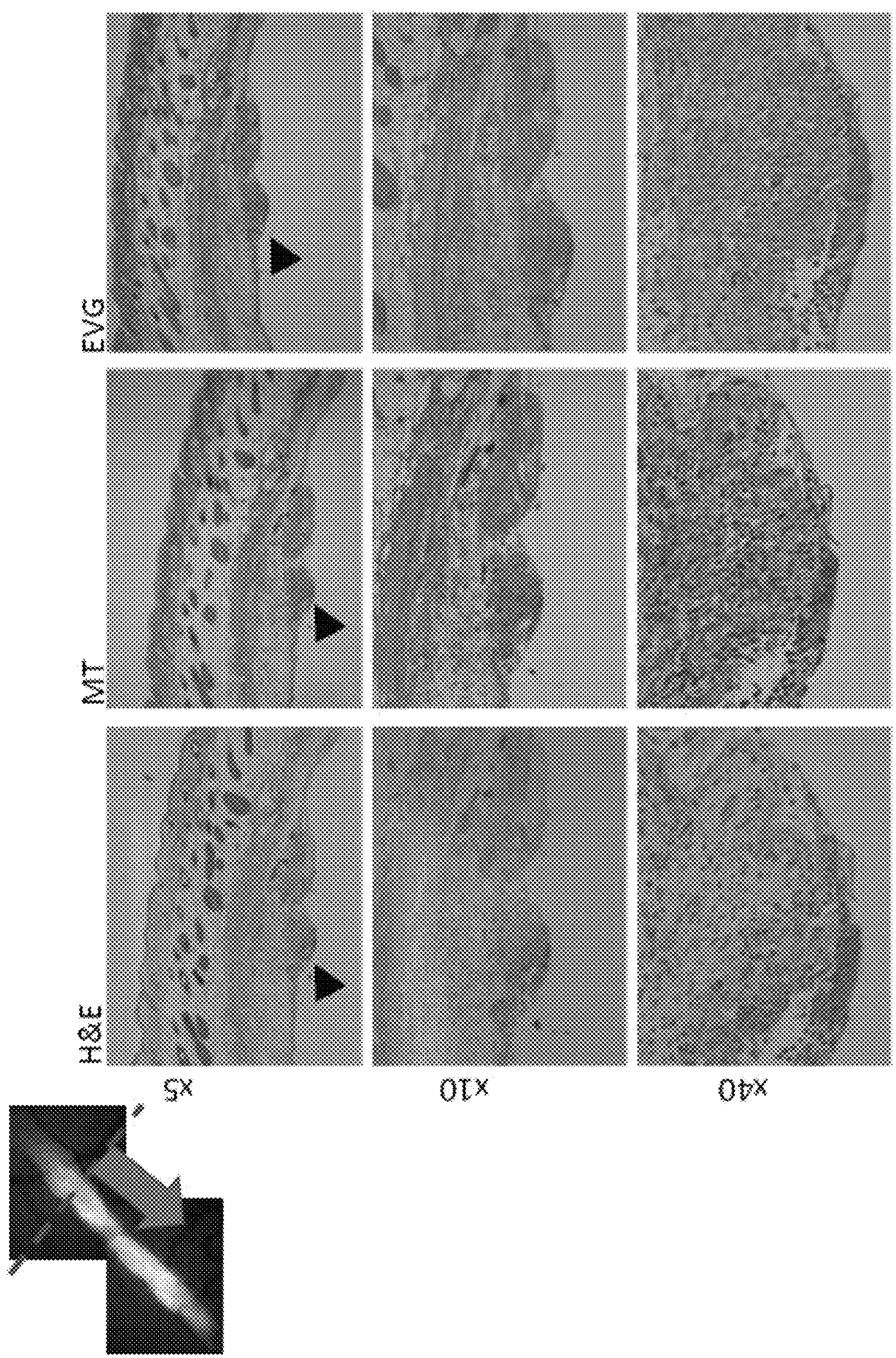
FIG. 14 is a histological analysis of a mouse osteoblast MC3T3-E1 into which GFP-inserted Type V collagen α1 had been introduced and expressed, implanted subcutaneously into the back of a C57BL/6 mouse, and extracted at 3 weeks.

Histological Analysis of Murine Skin Transplanted with GFP-Inserted Type V Collagen-α1-Expressing MC3T3-E1 Cells When GFP-inserted Type V collagen α1 expressing MC3T3-E1 cells were observed at the same position as in Example 7 at 3 weeks after subcutaneous transplantation, fibrous luminescence clumps continued to exist. The skin was harvested to contain the clumps, and after fixation, sections were made across the luminescence fibers. Hematoxylin-Eosin (HE) staining, Masson's Trichrome (MT) staining, and Elastica van Guison (EVG) staining were performed. Unusual aneurysm-like structures were observed on the backside of the fluoresced skin (arrowheads in FIG. 14), which were stained blue with Masson's Trichrome staining and pink with Elastica van Guison staining, confirming that the Type V collagen α1 probes of the present invention were able to form collagen fibers extracellularly even in living mice, which could be observed.

Example 9

Figure 15:
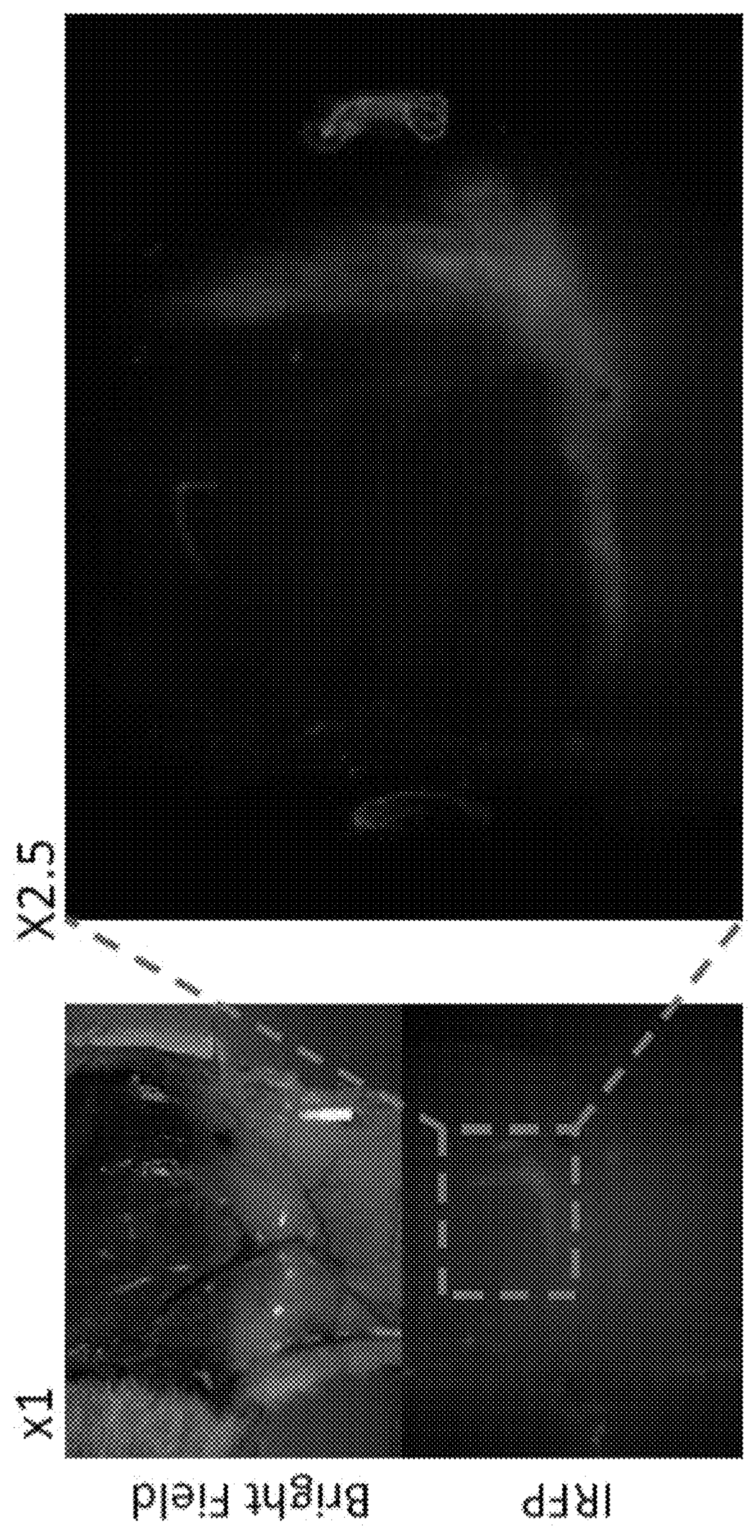
FIG. 15 shows microscopic images of skin of a C57BL/6 mouse in which a mouse osteoblast MC3T3-E1, into which Type V collagen α1 had been introduced and expressed, was implanted subcutaneously in the back of the C57BL/6 mouse and stained with fluorescent ligands for 2 weeks.

Murine Subcutaneous Implantation of Halotag-Inserted Type V Collagen-α1 Expressing MC3T3-E1 Cells $1\times10^6$ cells of a stable expression strain of Halotag-inserted Type V collagen-α1 expressing MC3T3-E1 were suspended in 50 μl of PBS(−) and implanted subcutaneously in the back of C57BL/6 albino mouse. Two weeks later, 50 μl of Stella700HaloTag ligands diluted in PBS(−) at 0.5 μM was administered to the cell-transplantation site, and after 1 hour of staining, the skin was turned inside-out and luminescence photographed, and a clump of collagen fibers was formed, which was illuminated by Stella700 near-infrared fluorescence (FIG. 15).

Example 10

Figure 16:
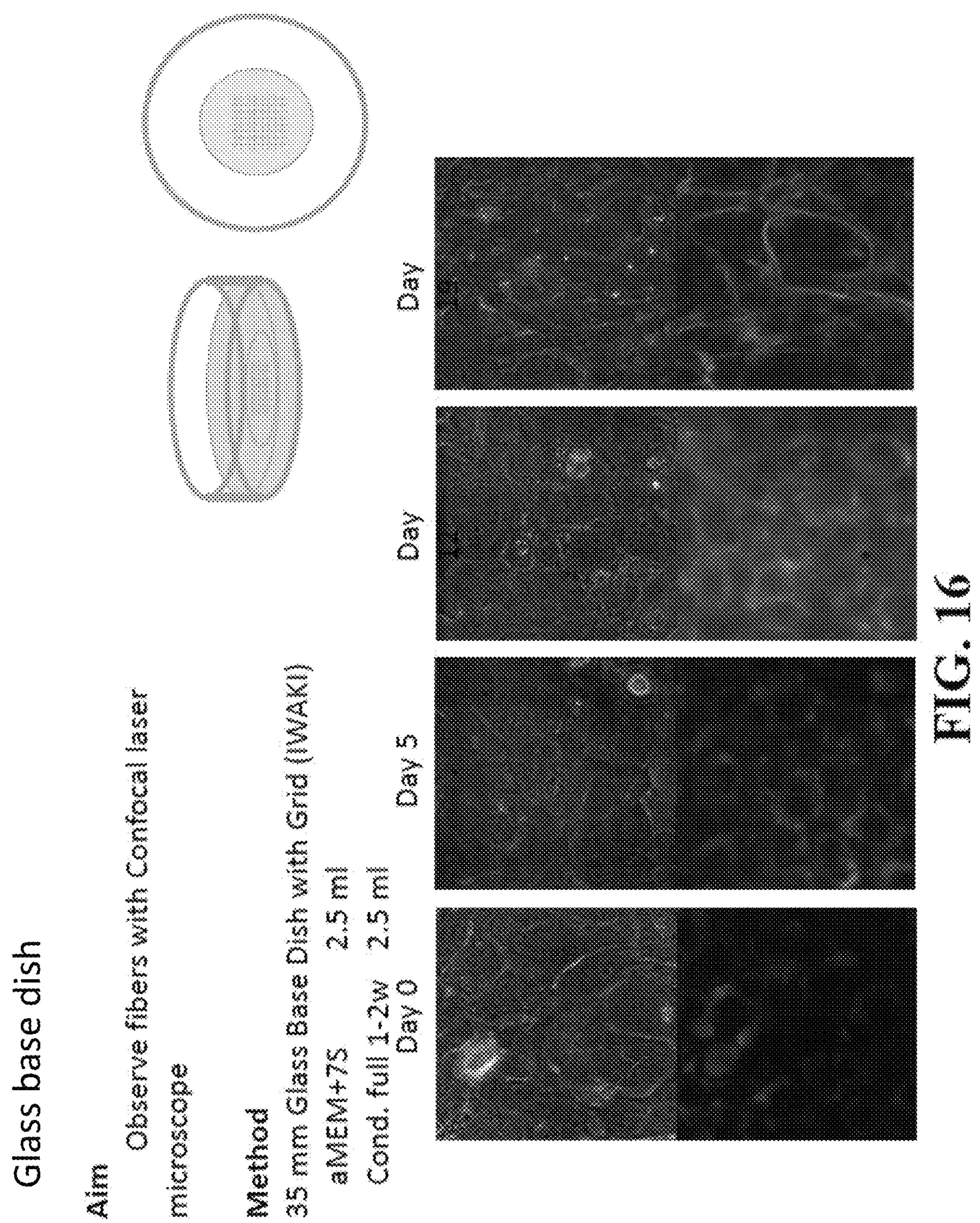
FIG. 16 shows microscopic images showing an improvement of the culture method of murine osteoblasts MC3T3-E1, into which GFP-inserted Type V collagen α1 had been introduced and expressed, so that the mouse osteoblasts form fibers even on a glass-bottom dish.
Figure 17:
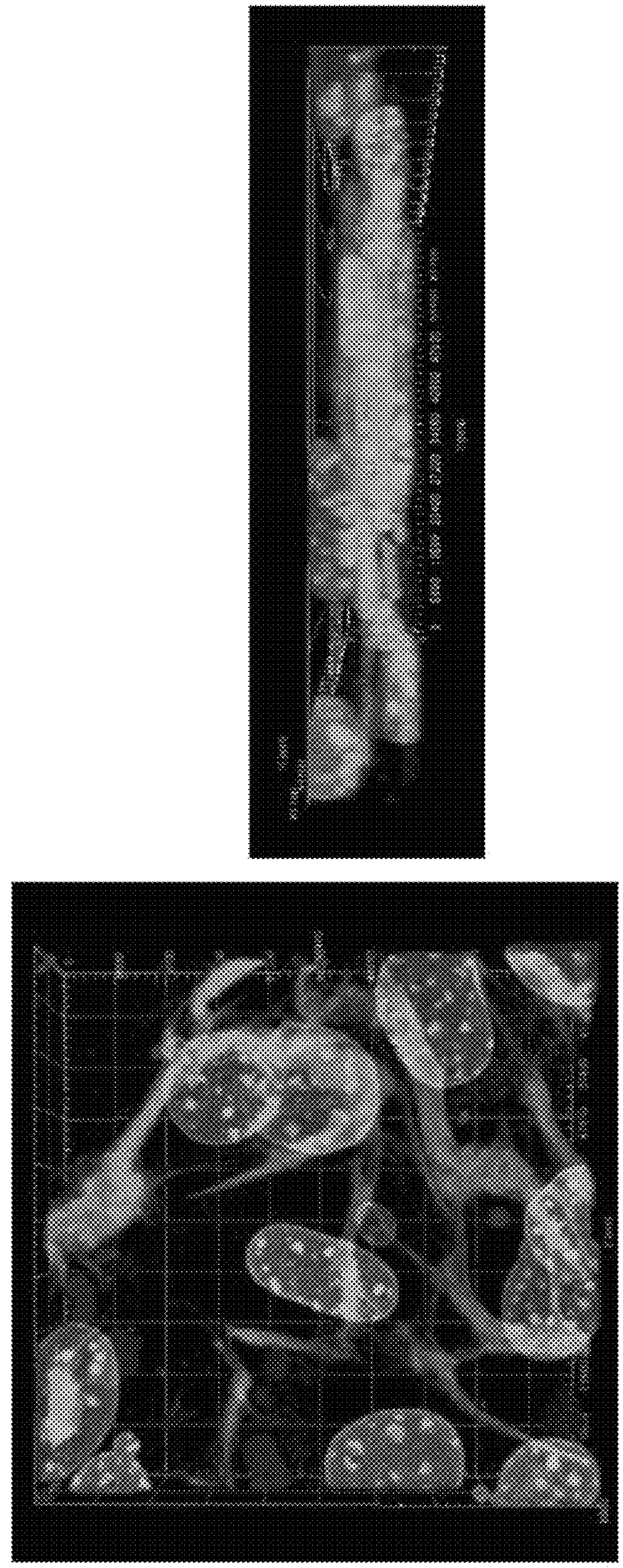
FIG. 17 shows super-resolution microscopic images of a mouse osteoblast MC3T3-E1, into which GFP-inserted Type V collagen α1 had been introduced and expressed, and which had been cultured, fibrillated on a glass-bottom dish.

Superresolution Microscopic Analysis of GFP-Inserted Type V Collagen-α1-Expressing MC3T3-E1 Cells A GFP-inserted Type V collagen α1-expressing MC3T3-E1 was cultured on a glass-bottom dish, and 19 days after switching to a stress culture capable of inducing collagen secretion, green fluorescent fibrous structures were observed outside the cells (FIG. 16; bottom panel of the photograph). This was fixed with 4% paraformaldehyde, then the cell nuclei were counterstained with Hoechst33342, and the cell nuclei were observed by super-resolution using Zeiss LSM880 Airyscan. Collagen fibers and cells formed a complex three-dimensional structure (FIG. 17).

Example 11

Figure 18:
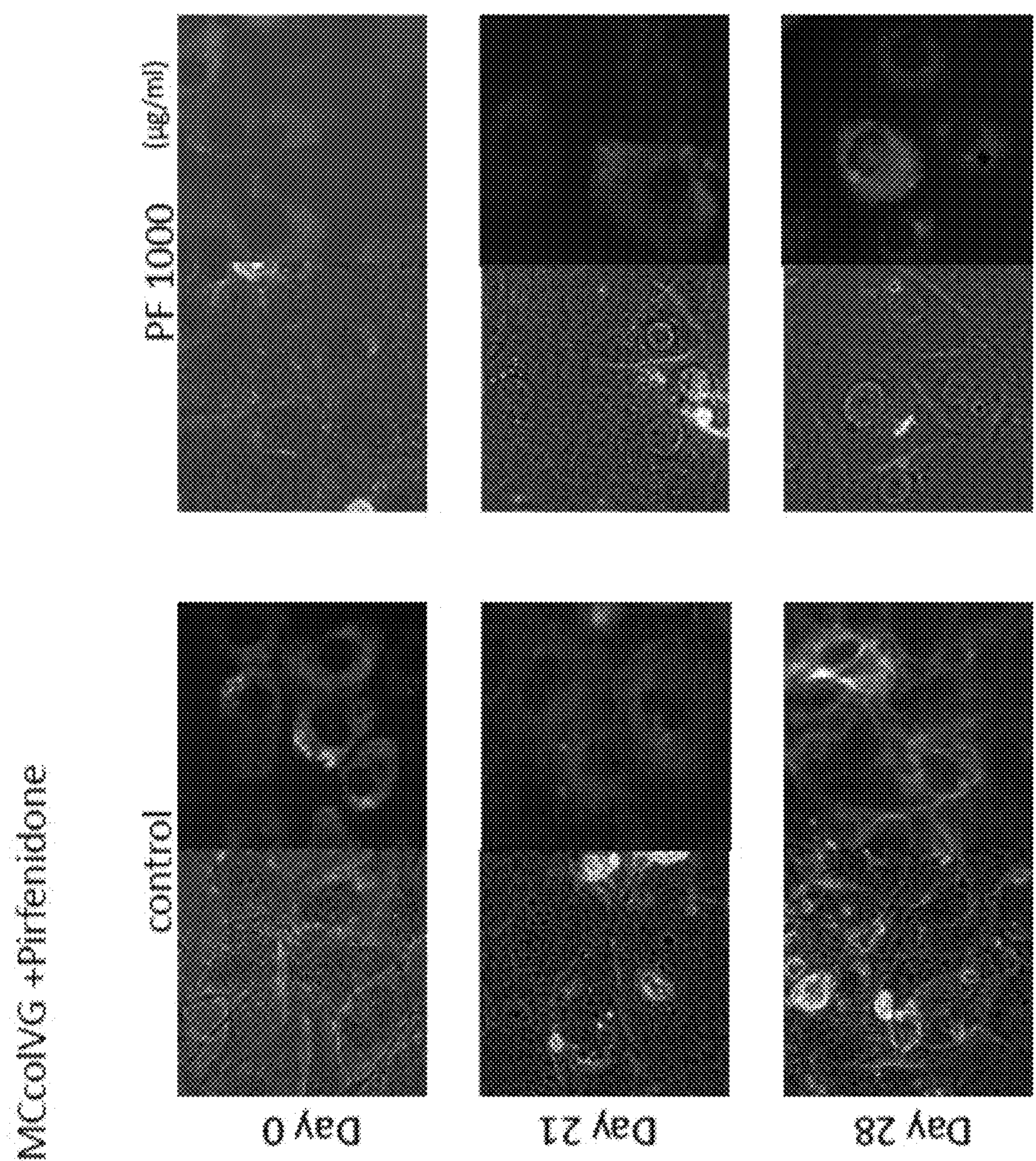
FIG. 18 shows a comparative view of the fibrogenic inhibitory effects of a drug in cultured mouse osteoblast MC3T3-E1, into which GFP-inserted Type V collagen α1 had been introduced and expressed, in a multi-well plate.

Fibrogenesis Inhibitory Experiments of GFP-Inserted Type V Collagen-α1 Expressing MC3T3-E1 Cells The GFP-inserted Type V collagen α1 expression MC3T3-E1 was cultured in multi-well plates and when switched to stress cultures capable of inducing collagen secretion, 1.0 mg/ml of Pirfenidone was added and compared to wells without such addition of Pirfenidone. After 28 days, green fluorescent fiber structures were observed extracellularly in the wells without Pirfenidone, whereas fiber formation was inhibited in the wells with Pirfenidone (FIG. 18). Thus, it has been revealed that a drug having an inhibitory effect on collagen secretion and fiber formation can be searched by using the present invention.

INDUSTRIAL APPLICABILITY

Since the present invention directly visualizes collagen fibers, the present invention is useful as a probe for monitoring fiber formation in real-time, and is also useful as a screening technique for a fiber-formation suppressing drug using the probe.

The present invention is also useful as a research tool for studying fibrosis.

The modified collagen protein of the present invention, or collagen fibers containing thereof, may also be useful as a delivery vehicle to the target site of the useful protein, since it may also enable the carrying of the therapeutic protein to the collagen fibers and delivery to the treatment site.

The present invention is useful for providing model animals of various diseases and the like capable of monitoring fibrosis symptoms in a non-invasive and real-time manner (e.g., experimental animals with a certain degree of genetic tradition and uniform genetic requirements, such as mice, rats, guinea pigs, gerbils, hamsters, ferrets, rabbits, dogs, minipigs, etc.).

The present invention is also useful in providing a cell culture dish, either before or after culturing under stress, which is precoated with a cell culture medium containing an expression cell line into which a polynucleotide encoding a modified collagen protein expressed in a transformed cell and capable of forming collagen fibers outside said cell has been introduced.

The invention claimed is:

1. A modified collagen protein that comprises an amino acid sequence selected from the group consisting of SEQ ID NOs: 2 and 4 or an amino acid sequence having at least 90% identity therewith.

2. A polynucleotide encoding the modified collagen protein according to claim 1.

3. The polynucleotide of claim 2 comprising the nucleotide sequence selected from the group consisting of SEQ ID NO: 1 and SEQ ID NO: 3 or a nucleotide sequence having at least 90% identity therewith.

4. An expression vector comprising the polynucleotide according to claim 2.

5. An expression cell line comprising the polynucleotide according to claim 2 or the expression vector according to claim 4.

6. A collagen-coated dish coated with the expression cell line according to claim 5.

7. A method for screening for an inhibitor of collagen secretion and/or collagen fiber formation, comprising the steps of:

culturing the expression cell line according to claim 5 under stress conditions in vitro;

adding to said culture a candidate agent of said inhibitor before the culturing under said stress conditions;

observing said expression cell line for collagen secretion and/or collagen fiber formation outside of said cell after said addition of said candidate agent in said culture; and selecting as said inhibitor said candidate agent having an effect of reducing said collagen secretion and/or collagen fiber formation as compared to the absence of said addition of said candidate agent.

8. The method according to claim 7, wherein said selecting comprises visualizing or imaging to detect labeling of the collagen and/or collagen fiber.

9. A method of forming a collagen fiber comprising a modified collagen protein, wherein said method comprises introducing the polynucleotide of claim 2 into a cell in vitro and culturing said cell under stress to form an extracellular collagen fiber.

10. The method according to claim 9, wherein said method further comprises visualizing or imaging to detect labeling of the collagen fiber.

11. A composition comprising the modified collagen protein according to claim 1.

* * * * *

SEQUENCE LISTING

<160> NUMBER OF SEQ ID NOS: 22

<210> SEQ ID NO 1
<211> LENGTH: 6375
<212> TYPE: DNA
<213> ORGANISM: Artificial Sequence

```
<220> FEATURE:
<223> OTHER INFORMATION: synthetic polynucleotide

<400> SEQUENCE: 1

atggacgtac acacccgctg gaaagctgcg cgcccaggcg ccctgctgct gtcttcgccg     60

ctactcctgt tcctgctgct gctgtgggcg ccgccttcga gccgcgcagc tcagccagca    120

gatcttctgg agatgctaga ttttcacaat ttgccctcag ggtaacgaa aaccacaggt    180

ttctgtgcta ctcgaagatc ttccagcgag ccggatgttg cctaccgagt ctctaaagat    240

gcacagctca gcatgcccac caagcagctg taccctgagt ctggttttcc cgaggacttc    300

tccatcctga caaccgtgaa agccaagaaa ggcagccagg ccttcctagt ctccatttac    360

aatgagcagg gcatccagca gttggggctg gagctgggcc gctcccctgt cttcctctat    420

gaggaccaca cagggaagcc cgggcctgaa gagtatccgc ttttccctgg catcaacttg    480

tccgatggca agtggcaccg aattgctctc agtgtctaca agaaaaatgt caccttgatc    540

ctcgactgta agaagaagat tacgaagttc ctcagccgca gtgaccaccc cataatagac    600

accaatggga ttgtcatgtt tggctcccgg attctggatg atgaaatatt tgagggtgac    660

atccaacagt tgcttttcgt ctctgacaac cgagctgcct atgactactg tgagcactac    720

agccccgact gtgacactgc ggtccctgac acacctcagt cacaggaccc taacccggat    780

gaatattacc cagaaggaga gggtgagacc tattactatg agtatccata ttatgaagac    840

cctgaagacc cgggaaagga gcctgcccct actcagaagc cagtggaagc tgccagagaa    900

accacagagg ttcctgagga gcagacccag cccctacccg aagcccctac agtgcctgag    960

accagtgaca cggctgacaa ggaggacagt ctagggatcg ggactatga ctacgtgccc   1020

ccagatgact attacactcc acccccatat gaagactttg gatatggcga gggtgtggag   1080

aaccctgacc agcccaccaa ccccgactca ggggctgagg tccccaccag caccactgtt   1140

acctccaaca cctccaatcc agctccagga gaagggaagg atgacctggg cggcgaattc   1200

accgaggaaa ccatcaagaa tctagaggaa aactactatg acccgtactt tgaccccgac   1260

tccgactcca gtgtctctcc atcagagata gggccaggca tgcccgctaa ccaggacacc   1320

atctttgagg cgatcgctgg ctccacctcc ggctccggca agcccggctc cggcgagggc   1380

tccaccaagc ccggcgctag tatggtgagc aagggcgagg agctgttcac cggggtggtg   1440

cccatcctgg tcgagctgga cggcgacgta aacggccaca agttcagcgt gtccggcgag   1500

ggcgagggcg atgccaccta cggcaagctg accctgaagt tcatctgcac caccggcaag   1560

ctgcccgtgc cctggcccac cctcgtgacc accctgacct acggcgtgca gtgcttcagc   1620

cgctaccccg accacatgaa gcagcacgac ttcttcaagt ccgccatgcc cgaaggctac   1680

gtccaggagc gcaccatctt cttcaaggac gacggcaact acaagacccg cgccgaggtg   1740

aagttcgagg gcgacaccct ggtgaaccgc atcgagctga agggcatcga cttcaaggag   1800

gacggcaaca tcctggggca caagctggag tacaactaca acagccacaa cgtctatatc   1860

atggccgaca agcagaagaa cggcatcaag gtgaacttca agatccgcca caacatcgag   1920

gacggcagcg tgcagctcgc cgaccactac cagcagaaca cccccatcgg cgacggcccc   1980

gtgctgctgc ccgacaacca ctacctgagc acccagtccg ccctgagcaa agaccccaac   2040

gagaagcgcg atcacatggt cctgctggag ttcgtgaccg ccgccgggat cactctcggc   2100

atggacgagc tgtacaagct cgacggctcc acctccggct ccggcaagcc cggctccggc   2160

gagggctcca ccaagcccgg cactagcggg attggaggac cccgaggtga gaaagggcaa   2220
```

-continued aagggagaac cagccatcat tgagccgggg atgctgatcg aggggccccc tggccctgaa 2280
ggccctgctg gtcttccagg acctccagga actacaggtc ctactggcca aatgggtgac 2340
cctggagaaa ggggtccccc tgggcgccca ggtcttcctg gagctgatgg cttgcctggc 2400
cccccaggta ccatgctcat gctgccgttc cggtttggag gcggtggcga tgccggttct 2460
aagggcccca tggtctctgc gcaggagtcc caggcccagg ctatcctcca gcaagccagg 2520
ttggcactga ggggaccagc tggcccaatg ggtctcaccg ggagacctgg ccccatgggt 2580
cctcctggga gtggcggttt gaaaggtgag ccaggagaca tgggacctca gggtcctcga 2640
ggtgtgcaag gcccacctgg cccaacaggg aagcctggaa gacggggccg tgctggaagt 2700
gatggagcca gaggcatgcc tggacaaaca ggccccaagg gtgaccgtgg ctttgatggt 2760
ctggctgggt tgccgggaga gaaaggccat agaggtgacc ctggtccttc tggcccgccc 2820
ggaatcccag gagatgatgg agaaaggggt gacgatggag aagttgggcc caggggactg 2880
cccggggagc ctggaccacg tggtctgctt gggccaaaag gcccccccagg gcctcctgga 2940 cctcctggtg taacgggtat ggatggccag cctggcccaa aaggaaatgt gggtccccag 3000
ggagagcctg ggccgccagg acagcagggt aatcctggtg cccagggtct tccaggtccc 3060
cagggtgcca ttggtcctcc aggagaaaag ggtcctttgg ggaaaccagg tctcccagga 3120
atgccaggcg ctgatggacc cccggggcac cctggaaaag aaggtcctcc aggagagaaa 3180
ggaggccagg gtcctcctgg cccccagggt cccattggct accccggtcc acgaggagtc 3240
aagggggcag atggcatccg aggtctgaag ggcaccaagg gggagaaggg tgaagacggc 3300
ttccctgggt ttaaaggcga catgggaata aagggtgacc gggggggaaat cggcccacct 3360 ggtccccgag gagaagatgg tcctgaaggt ccaaagggtc gaggtggtcc caatggtgat 3420
cctggtcccc tggggcccac tggggaaaag ggaaagcttg gcgtgcccgg attaccgggg 3480
tacccaggaa gacaaggcc aaagggttcc attggattcc ctggcttccc gggcgccaac 3540
ggagagaagg gtggcagggg gacacctgga aagccaggac cacggggaca gagaggccca 3600
acgggcccgc ggggtgaacg aggcccacga ggcatcacgg ggaagcctgg ccctaagggc 3660
aactccggag gtgatggccc agctggccct cctggtgaac ggggacccaa cggaccccaa 3720
ggtcccaccg gctttcctgg acccaagggt cccccgggcc caccaggcaa ggacggactc 3780
cctggacacc ctgggcagag aggggagacc ggtttccaag gcaagactgg ccctccaggg 3840
cccccaggag tggttggccc tcagggtccc acaggagaga cgggccccat gggtgagcgt 3900
ggccatcctg gtcctccagg ccctcctggt gaacagggcc tcccaggtgc tgctgggaaa 3960
gaaggaacga agggtgaccc aggtcctgct ggcctccctg ggaaggatgg ccctccagga 4020
ttgcgtggat tccctgggga ccgagggcta cctggccccg tgggagccct tggactcaaa 4080
ggcagtgaag gcccccctgg cccaccaggt cctgcgggtt ctccagggga gagaggacca 4140
gctggtgccg ctgggcccat cggaattcca gggagacctg ggcctcaggg acctccgggg 4200
cctgctggag agaaaggact tcctggcgag aaaggtccac aaggcccagc tggccgagat 4260
ggcctccaag gtcccgtggg gctccctgga ccagccggcc cagtgggtcc tcctggagaa 4320
gatggagata agggagagat cggagagcca gggcagaagg gaagcaaggg cgacaaaggc 4380
gagcagggtc ctcctgggcc taccggtcct caaggcccga ttggacagcc aggcccttcg 4440
ggagcagatg gtgaacctgg ccctcgtgga cagcagggcc tgtttgggca gaaaggagat 4500
gaaggttcaa gaggtttccc aggacccccc gggccagtgg gattgcaggg tttgccagga 4560
cctccaggag aaaagggcga gacaggagac gtgggccaga tgggccctcc tggtccacca 4620

```
ggcccccgag gaccctctgg agctccaggt gccgatggac cacagggtcc tcctggaggg   4680

attggcaacc ctggtgcagt cggagaaaag ggagaacctg gtgaagctgg agatcctggc   4740

cttccaggag aaggaggtcc cctgggacct aaaggagaaa gaggggagaa gggagaggct   4800

ggcccctctg gtgctgctgg accccctgga cccaaaggcc ctcctggaga tgatggcccc   4860

aaaggcagcc ctggccctgt gggctttcct ggagatcctg gtccccctgg agagccaggc   4920

cccgcaggtc aagacggccc acctggtgac aaaggggacg atggtgaacc tgggcagacg   4980

gggtccccgg gccctactgg tgaacctggt ccatctgggc ctccaggaaa gaggggtccc   5040

ccaggccctg caggccctga aggcaggcag ggggagaaag gagccaaggg agaagctggc   5100

ttagaaggcc ctcctgggaa gactggcccc attggccccc aaggggcccc tgggaagcct   5160

ggccccgatg gtctccgtgg aatccctggt cctgtgggtg agcaaggcct cccaggatcc   5220

ccaggccccg atggtccacc cggccccatg ggtcctccag gactccctgg cctcaaagga   5280

gactccggtc ccaaaggtga aaagggccat ccaggcctga ttggactcat cggccctccg   5340

ggagagcaag gtgaaaaggg tgaccgtgga ctcccaggcc cccagggttc atctggtcct   5400

aaaggagatc agggcatcac aggtccttct ggcccacttg ggcctcctgg tcctcctggc   5460

ttgccgggcc ctccaggtcc caaaggtgct aagggctctt cgggtcccac cggccccgaag   5520

ggtgaggcag gccacccagg actccccggc ccacctggcc ctccgggtga ggtcatccag   5580

cccctgccaa tccaggcctc caggactcgg cggaacattg atgccagcca gctcctggac   5640

gatggggctg ggagagcta cgtggattat gcagatggca tggaagagat ctttggttcc   5700

ctcaactccc tgaagctgga gattgaacag atgaagcgac cactgggcac ccagcagaac   5760

ccagcccgta cctgcaagga tctacagctc tgtcatcctg acttcccaga tggcgaatac   5820

tgggtcgatc ccaaccaagg gtgctccagg gactccttca aagtctactg caatttcaca   5880

gctggagggt ccacgtgcgt cttccctgac aagaagtctg agggaagtaa aatggcccgg   5940

tggcccaaag aacagccttc cacctggtat agtcagtaca agcggggttc cctgctctcc   6000

tatgtggatg ctgaaggcaa ccccgtgggc gtggtacaaa tgaccttcct gcggctgctg   6060

agcgcctctg cccaccagaa cgtcacctac aactgctacc agtccgtggc ctggcaggat   6120

gccgccacag gcagctatga taaggctatc cgcttcttgg gctccaacga tgaggaaatg   6180

tcttatgata acaaccccta catccgtgcc ctggtggatg gctgtgctac caagaaaggc   6240

taccagaaga cggtgctgga gatcgacacg cccaaagtag agcaagtccc cattgtggac   6300

atcatgttca acgactttgg cgaagcctca cagaaatttg gatttgaagt ggggccagct   6360

tgcttcctag gctag                                                    6375
```

```
<210> SEQ ID NO 2
<211> LENGTH: 2124
<212> TYPE: PRT
<213> ORGANISM: Artificial Sequence
<220> FEATURE:
<223> OTHER INFORMATION: synthetic peptide

<400> SEQUENCE: 2

Met Asp Val His Thr Arg Trp Lys Ala Ala Arg Pro Gly Ala Leu Leu
1               5                   10                  15

Leu Ser Ser Pro Leu Leu Leu Phe Leu Leu Leu Leu Trp Ala Pro Pro
            20                  25                  30

Ser Ser Arg Ala Ala Gln Pro Ala Asp Leu Leu Glu Met Leu Asp Phe
        35                  40                  45
```

```
His Asn Leu Pro Ser Gly Val Thr Lys Thr Thr Gly Phe Cys Ala Thr
    50                  55                  60

Arg Arg Ser Ser Ser Glu Pro Asp Val Ala Tyr Arg Val Ser Lys Asp
65                  70                  75                  80

Ala Gln Leu Ser Met Pro Thr Lys Gln Leu Tyr Pro Glu Ser Gly Phe
                85                  90                  95

Pro Glu Asp Phe Ser Ile Leu Thr Thr Val Lys Ala Lys Lys Gly Ser
            100                 105                 110

Gln Ala Phe Leu Val Ser Ile Tyr Asn Glu Gln Gly Ile Gln Gln Leu
        115                 120                 125

Gly Leu Glu Leu Gly Arg Ser Pro Val Phe Leu Tyr Glu Asp His Thr
    130                 135                 140

Gly Lys Pro Gly Pro Glu Glu Tyr Pro Leu Phe Pro Gly Ile Asn Leu
145                 150                 155                 160

Ser Asp Gly Lys Trp His Arg Ile Ala Leu Ser Val Tyr Lys Lys Asn
                165                 170                 175

Val Thr Leu Ile Leu Asp Cys Lys Lys Lys Ile Thr Lys Phe Leu Ser
            180                 185                 190

Arg Ser Asp His Pro Ile Ile Asp Thr Asn Gly Ile Val Met Phe Gly
        195                 200                 205

Ser Arg Ile Leu Asp Asp Glu Ile Phe Glu Gly Asp Ile Gln Gln Leu
    210                 215                 220

Leu Phe Val Ser Asp Asn Arg Ala Ala Tyr Asp Tyr Cys Glu His Tyr
225                 230                 235                 240

Ser Pro Asp Cys Asp Thr Ala Val Pro Asp Thr Pro Gln Ser Gln Asp
                245                 250                 255

Pro Asn Pro Asp Glu Tyr Tyr Pro Glu Gly Glu Gly Glu Thr Tyr Tyr
            260                 265                 270

Tyr Glu Tyr Pro Tyr Tyr Glu Asp Pro Glu Asp Pro Gly Lys Glu Pro
        275                 280                 285

Ala Pro Thr Gln Lys Pro Val Glu Ala Ala Arg Glu Thr Thr Glu Val
    290                 295                 300

Pro Glu Glu Gln Thr Gln Pro Leu Pro Glu Ala Pro Thr Val Pro Glu
305                 310                 315                 320

Thr Ser Asp Thr Ala Asp Lys Glu Asp Ser Leu Gly Ile Gly Asp Tyr
                325                 330                 335

Asp Tyr Val Pro Pro Asp Asp Tyr Tyr Thr Pro Pro Pro Tyr Glu Asp
            340                 345                 350

Phe Gly Tyr Gly Glu Gly Val Glu Asn Pro Asp Gln Pro Thr Asn Pro
        355                 360                 365

Asp Ser Gly Ala Glu Val Pro Thr Ser Thr Thr Val Thr Ser Asn Thr
    370                 375                 380

Ser Asn Pro Ala Pro Gly Glu Gly Lys Asp Asp Leu Gly Gly Glu Phe
385                 390                 395                 400

Thr Glu Glu Thr Ile Lys Asn Leu Glu Glu Asn Tyr Tyr Asp Pro Tyr
                405                 410                 415

Phe Asp Pro Asp Ser Asp Ser Ser Val Ser Pro Ser Glu Ile Gly Pro
            420                 425                 430

Gly Met Pro Ala Asn Gln Asp Thr Ile Phe Glu Ala Ile Ala Gly Ser
        435                 440                 445

Thr Ser Gly Ser Gly Lys Pro Gly Ser Gly Glu Gly Ser Thr Lys Pro
    450                 455                 460
```

-continued

```
Gly Ala Ser Met Val Ser Lys Gly Glu Glu Leu Phe Thr Gly Val Val
465                 470                 475                 480

Pro Ile Leu Val Glu Leu Asp Gly Asp Val Asn Gly His Lys Phe Ser
                485                 490                 495

Val Ser Gly Glu Gly Glu Gly Asp Ala Thr Tyr Gly Lys Leu Thr Leu
            500                 505                 510

Lys Phe Ile Cys Thr Thr Gly Lys Leu Pro Val Pro Trp Pro Thr Leu
        515                 520                 525

Val Thr Thr Leu Thr Tyr Gly Val Gln Cys Phe Ser Arg Tyr Pro Asp
    530                 535                 540

His Met Lys Gln His Asp Phe Phe Lys Ser Ala Met Pro Glu Gly Tyr
545                 550                 555                 560

Val Gln Glu Arg Thr Ile Phe Phe Lys Asp Asp Gly Asn Tyr Lys Thr
                565                 570                 575

Arg Ala Glu Val Lys Phe Glu Gly Asp Thr Leu Val Asn Arg Ile Glu
            580                 585                 590

Leu Lys Gly Ile Asp Phe Lys Glu Asp Gly Asn Ile Leu Gly His Lys
        595                 600                 605

Leu Glu Tyr Asn Tyr Asn Ser His Asn Val Tyr Ile Met Ala Asp Lys
    610                 615                 620

Gln Lys Asn Gly Ile Lys Val Asn Phe Lys Ile Arg His Asn Ile Glu
625                 630                 635                 640

Asp Gly Ser Val Gln Leu Ala Asp His Tyr Gln Gln Asn Thr Pro Ile
                645                 650                 655

Gly Asp Gly Pro Val Leu Leu Pro Asp Asn His Tyr Leu Ser Thr Gln
            660                 665                 670

Ser Ala Leu Ser Lys Asp Pro Asn Glu Lys Arg Asp His Met Val Leu
        675                 680                 685

Leu Glu Phe Val Thr Ala Ala Gly Ile Thr Leu Gly Met Asp Glu Leu
    690                 695                 700

Tyr Lys Leu Asp Gly Ser Thr Ser Gly Ser Gly Lys Pro Gly Ser Gly
705                 710                 715                 720

Glu Gly Ser Thr Lys Pro Gly Thr Ser Gly Ile Gly Gly Pro Arg Gly
                725                 730                 735

Glu Lys Gly Gln Lys Gly Glu Pro Ala Ile Ile Glu Pro Gly Met Leu
            740                 745                 750

Ile Glu Gly Pro Pro Gly Pro Glu Gly Pro Ala Gly Leu Pro Gly Pro
        755                 760                 765

Pro Gly Thr Thr Gly Pro Thr Gly Gln Met Gly Asp Pro Gly Glu Arg
    770                 775                 780

Gly Pro Pro Gly Arg Pro Gly Leu Pro Gly Ala Asp Gly Leu Pro Gly
785                 790                 795                 800

Pro Pro Gly Thr Met Leu Met Leu Pro Phe Arg Phe Gly Gly Gly Gly
                805                 810                 815

Asp Ala Gly Ser Lys Gly Pro Met Val Ser Ala Gln Glu Ser Gln Ala
            820                 825                 830

Gln Ala Ile Leu Gln Gln Ala Arg Leu Ala Leu Arg Gly Pro Ala Gly
        835                 840                 845

Pro Met Gly Leu Thr Gly Arg Pro Gly Pro Met Gly Pro Pro Gly Ser
    850                 855                 860

Gly Gly Leu Lys Gly Glu Pro Gly Asp Met Gly Pro Gln Gly Pro Arg
865                 870                 875                 880

Gly Val Gln Gly Pro Pro Gly Pro Thr Gly Lys Pro Gly Arg Arg Gly
```

```
                885                 890                 895

Arg Ala Gly Ser Asp Gly Ala Arg Gly Met Pro Gly Gln Thr Gly Pro
            900                 905                 910

Lys Gly Asp Arg Gly Phe Asp Gly Leu Ala Gly Leu Pro Gly Glu Lys
        915                 920                 925

Gly His Arg Gly Asp Pro Gly Pro Ser Gly Pro Pro Gly Ile Pro Gly
    930                 935                 940

Asp Asp Gly Glu Arg Gly Asp Asp Gly Glu Val Gly Pro Arg Gly Leu
945                 950                 955                 960

Pro Gly Glu Pro Gly Pro Arg Gly Leu Leu Gly Pro Lys Gly Pro Pro
                965                 970                 975

Gly Pro Pro Gly Pro Pro Gly Val Thr Gly Met Asp Gly Gln Pro Gly
            980                 985                 990

Pro Lys Gly Asn Val Gly Pro Gln  Gly Glu Pro Gly Pro  Pro Gly Gln
        995                 1000                 1005

Gln Gly  Asn Pro Gly Ala Gln  Gly Leu Pro Gly Pro  Gln Gly Ala
    1010                 1015                 1020

Ile Gly  Pro Pro Gly Glu Lys  Gly Pro Leu Gly Lys  Pro Gly Leu
    1025                 1030                 1035

Pro Gly  Met Pro Gly Ala Asp  Gly Pro Pro Gly His  Pro Gly Lys
    1040                 1045                 1050

Glu Gly  Pro Pro Gly Glu Lys  Gly Gly Gln Gly Pro  Pro Gly Pro
    1055                 1060                 1065

Gln Gly  Pro Ile Gly Tyr Pro  Gly Pro Arg Gly Val  Lys Gly Ala
    1070                 1075                 1080

Asp Gly  Ile Arg Gly Leu Lys  Gly Thr Lys Gly Glu  Lys Gly Glu
    1085                 1090                 1095

Asp Gly  Phe Pro Gly Phe Lys  Gly Asp Met Gly Ile  Lys Gly Asp
    1100                 1105                 1110

Arg Gly  Glu Ile Gly Pro Pro  Gly Pro Arg Gly Glu  Asp Gly Pro
    1115                 1120                 1125

Glu Gly  Pro Lys Gly Arg Gly  Gly Pro Asn Gly Asp  Pro Gly Pro
    1130                 1135                 1140

Leu Gly  Pro Thr Gly Glu Lys  Gly Lys Leu Gly Val  Pro Gly Leu
    1145                 1150                 1155

Pro Gly  Tyr Pro Gly Arg Gln  Gly Pro Lys Gly Ser  Ile Gly Phe
    1160                 1165                 1170

Pro Gly  Phe Pro Gly Ala Asn  Gly Glu Lys Gly Gly  Arg Gly Thr
    1175                 1180                 1185

Pro Gly  Lys Pro Gly Pro Arg  Gly Gln Arg Gly Pro  Thr Gly Pro
    1190                 1195                 1200

Arg Gly  Glu Arg Gly Pro Arg  Gly Ile Thr Gly Lys  Pro Gly Pro
    1205                 1210                 1215

Lys Gly  Asn Ser Gly Gly Asp  Gly Pro Ala Gly Pro  Pro Gly Glu
    1220                 1225                 1230

Arg Gly  Pro Asn Gly Pro Gln  Gly Pro Thr Gly Phe  Pro Gly Pro
    1235                 1240                 1245

Lys Gly  Pro Pro Gly Pro Pro  Gly Lys Asp Gly Leu  Pro Gly His
    1250                 1255                 1260

Pro Gly  Gln Arg Gly Glu Thr  Gly Phe Gln Gly Lys  Thr Gly Pro
    1265                 1270                 1275

Pro Gly  Pro Pro Gly Val Val  Gly Pro Gln Gly Pro  Thr Gly Glu
    1280                 1285                 1290
```

```
Thr Gly  Pro Met Gly Glu Arg  Gly His Pro Gly Pro  Pro Gly Pro
    1295                 1300                 1305

Pro Gly  Glu Gln Gly Leu Pro  Gly Ala Ala Gly Lys  Glu Gly Thr
    1310                 1315                 1320

Lys Gly  Asp Pro Gly Pro Ala  Gly Leu Pro Gly Lys  Asp Gly Pro
    1325                 1330                 1335

Pro Gly  Leu Arg Gly Phe Pro  Gly Asp Arg Gly Leu  Pro Gly Pro
    1340                 1345                 1350

Val Gly  Ala Leu Gly Leu Lys  Gly Ser Glu Gly Pro  Pro Gly Pro
    1355                 1360                 1365

Pro Gly  Pro Ala Gly Ser Pro  Gly Glu Arg Gly Pro  Ala Gly Ala
    1370                 1375                 1380

Ala Gly  Pro Ile Gly Ile Pro  Gly Arg Pro Gly Pro  Gln Gly Pro
    1385                 1390                 1395

Pro Gly  Pro Ala Gly Glu Lys  Gly Leu Pro Gly Glu  Lys Gly Pro
    1400                 1405                 1410

Gln Gly  Pro Ala Gly Arg Asp  Gly Leu Gln Gly Pro  Val Gly Leu
    1415                 1420                 1425

Pro Gly  Pro Ala Gly Pro Val  Gly Pro Pro Gly Glu  Asp Gly Asp
    1430                 1435                 1440

Lys Gly  Glu Ile Gly Glu Pro  Gly Gln Lys Gly Ser  Lys Gly Asp
    1445                 1450                 1455

Lys Gly  Glu Gln Gly Pro Pro  Gly Pro Thr Gly Pro  Gln Gly Pro
    1460                 1465                 1470

Ile Gly  Gln Pro Gly Pro Ser  Gly Ala Asp Gly Glu  Pro Gly Pro
    1475                 1480                 1485

Arg Gly  Gln Gln Gly Leu Phe  Gly Gln Lys Gly Asp  Glu Gly Ser
    1490                 1495                 1500

Arg Gly  Phe Pro Gly Pro Pro  Gly Pro Val Gly Leu  Gln Gly Leu
    1505                 1510                 1515

Pro Gly  Pro Pro Gly Glu Lys  Gly Glu Thr Gly Asp  Val Gly Gln
    1520                 1525                 1530

Met Gly  Pro Pro Gly Pro Pro  Gly Pro Arg Gly Pro  Ser Gly Ala
    1535                 1540                 1545

Pro Gly  Ala Asp Gly Pro Gln  Gly Pro Pro Gly Gly  Ile Gly Asn
    1550                 1555                 1560

Pro Gly  Ala Val Gly Glu Lys  Gly Glu Pro Gly Glu  Ala Gly Asp
    1565                 1570                 1575

Pro Gly  Leu Pro Gly Glu Gly  Gly Pro Leu Gly Pro  Lys Gly Glu
    1580                 1585                 1590

Arg Gly  Glu Lys Gly Glu Ala  Gly Pro Ser Gly Ala  Ala Gly Pro
    1595                 1600                 1605

Pro Gly  Pro Lys Gly Pro Pro  Gly Asp Asp Gly Pro  Lys Gly Ser
    1610                 1615                 1620

Pro Gly  Pro Val Gly Phe Pro  Gly Asp Pro Gly Pro  Pro Gly Glu
    1625                 1630                 1635

Pro Gly  Pro Ala Gly Gln Asp  Gly Pro Pro Gly Asp  Lys Gly Asp
    1640                 1645                 1650

Asp Gly  Glu Pro Gly Gln Thr  Gly Ser Pro Gly Pro  Thr Gly Glu
    1655                 1660                 1665

Pro Gly  Pro Ser Gly Pro Pro  Gly Lys Arg Gly Pro  Pro Gly Pro
    1670                 1675                 1680
```

```
Ala Gly Pro Glu Gly Arg Gln Gly Glu Lys Gly Ala Lys Gly Glu
    1685                1690                1695

Ala Gly Leu Glu Gly Pro Pro Gly Lys Thr Gly Pro Ile Gly Pro
    1700                1705                1710

Gln Gly Ala Pro Gly Lys Pro Gly Pro Asp Gly Leu Arg Gly Ile
    1715                1720                1725

Pro Gly Pro Val Gly Glu Gln Gly Leu Pro Gly Ser Pro Gly Pro
    1730                1735                1740

Asp Gly Pro Pro Gly Pro Met Gly Pro Pro Gly Leu Pro Gly Leu
    1745                1750                1755

Lys Gly Asp Ser Gly Pro Lys Gly Glu Lys Gly His Pro Gly Leu
    1760                1765                1770

Ile Gly Leu Ile Gly Pro Pro Gly Glu Gln Gly Glu Lys Gly Asp
    1775                1780                1785

Arg Gly Leu Pro Gly Pro Gln Gly Ser Ser Gly Pro Lys Gly Asp
    1790                1795                1800

Gln Gly Ile Thr Gly Pro Ser Gly Pro Leu Gly Pro Pro Gly Pro
    1805                1810                1815

Pro Gly Leu Pro Gly Pro Pro Gly Pro Lys Gly Ala Lys Gly Ser
    1820                1825                1830

Ser Gly Pro Thr Gly Pro Lys Gly Glu Ala Gly His Pro Gly Leu
    1835                1840                1845

Pro Gly Pro Pro Gly Pro Pro Gly Glu Val Ile Gln Pro Leu Pro
    1850                1855                1860

Ile Gln Ala Ser Arg Thr Arg Arg Asn Ile Asp Ala Ser Gln Leu
    1865                1870                1875

Leu Asp Asp Gly Ala Gly Glu Ser Tyr Val Asp Tyr Ala Asp Gly
    1880                1885                1890

Met Glu Glu Ile Phe Gly Ser Leu Asn Ser Leu Lys Leu Glu Ile
    1895                1900                1905

Glu Gln Met Lys Arg Pro Leu Gly Thr Gln Gln Asn Pro Ala Arg
    1910                1915                1920

Thr Cys Lys Asp Leu Gln Leu Cys His Pro Asp Phe Pro Asp Gly
    1925                1930                1935

Glu Tyr Trp Val Asp Pro Asn Gln Gly Cys Ser Arg Asp Ser Phe
    1940                1945                1950

Lys Val Tyr Cys Asn Phe Thr Ala Gly Gly Ser Thr Cys Val Phe
    1955                1960                1965

Pro Asp Lys Lys Ser Glu Gly Ser Lys Met Ala Arg Trp Pro Lys
    1970                1975                1980

Glu Gln Pro Ser Thr Trp Tyr Ser Gln Tyr Lys Arg Gly Ser Leu
    1985                1990                1995

Leu Ser Tyr Val Asp Ala Glu Gly Asn Pro Val Gly Val Val Gln
    2000                2005                2010

Met Thr Phe Leu Arg Leu Leu Ser Ala Ser Ala His Gln Asn Val
    2015                2020                2025

Thr Tyr Asn Cys Tyr Gln Ser Val Ala Trp Gln Asp Ala Ala Thr
    2030                2035                2040

Gly Ser Tyr Asp Lys Ala Ile Arg Phe Leu Gly Ser Asn Asp Glu
    2045                2050                2055

Glu Met Ser Tyr Asp Asn Asn Pro Tyr Ile Arg Ala Leu Val Asp
    2060                2065                2070

Gly Cys Ala Thr Lys Lys Gly Tyr Gln Lys Thr Val Leu Glu Ile
```

```
    2075                2080                2085

Asp Thr  Pro Lys Val Glu Gln  Val Pro Ile Val Asp  Ile Met Phe
    2090                2095                2100

Asn Asp  Phe Gly Glu Ala Ser  Gln Lys Phe Gly Phe  Glu Val Gly
    2105                2110                2115

Pro Ala  Cys Phe Leu Gly
    2120


<210> SEQ ID NO 3
<211> LENGTH: 6549
<212> TYPE: DNA
<213> ORGANISM: Artificial Sequence
<220> FEATURE:
<223> OTHER INFORMATION: synthetic polynucleotide

<400> SEQUENCE: 3

atggacgtac acacccgctg gaaagctgcg cgcccaggcg ccctgctgct gtcttcgccg     60

ctactcctgt tcctgctgct gctgtgggcg ccgccttcga gccgcgcagc tcagccagca    120

gatcttctgg agatgctaga ttttcacaat ttgccctcag ggtaacgaa aaccacaggt    180

ttctgtgcta ctcgaagatc ttccagcgag ccggatgttg cctaccgagt ctctaaagat    240

gcacagctca gcatgcccac caagcagctg taccctgagt ctggttttcc cgaggacttc    300

tccatcctga caaccgtgaa agccaagaaa ggcagccagg ccttcctagt ctccatttac    360

aatgagcagg gcatccagca gttggggctg gagctgggcc gctcccctgt cttcctctat    420

gaggaccaca cagggaagcc cgggcctgaa gagtatccgc ttttccctgg catcaacttg    480

tccgatggca agtggcaccg aattgctctc agtgtctaca agaaaaatgt caccttgatc    540

ctcgactgta agaagaagat tacgaagttc ctcagccgca gtgaccaccc cataatagac    600

accaatggga ttgtcatgtt tggctcccgg attctggatg atgaaatatt tgagggtgac    660

atccaacagt tgcttttcgt ctctgacaac cgagctgcct atgactactg tgagcactac    720

agccccgact gtgacactgc ggtccctgac acacctcagt cacaggaccc taacccggat    780

gaatattacc cagaaggaga gggtgagacc tattactatg agtatccata ttatgaagac    840

cctgaagacc cgggaaagga gcctgcccct actcagaagc cagtggaagc tgccagagaa    900

accacagagg ttcctgagga gcagacccag cccctacccg aagcccctac agtgcctgag    960

accagtgaca cggctgacaa ggaggacagt ctagggatcg gggactatga ctacgtgccc   1020

ccagatgact attacactcc acccccatat gaagactttg gatatggcga gggtgtggag   1080

aaccctgacc agcccaccaa ccccgactca ggggctgagg tccccaccag caccactgtt   1140

acctccaaca cctccaatcc agctccagga gaagggaagg atgacctggg cggcgaattc   1200

accgaggaaa ccatcaagaa tctagaggaa aactactatg acccgtactt tgaccccgac   1260

tccgactcca gtgtctctcc atcagagata gggccaggca tgcccgctaa ccaggacacc   1320

atctttgagg cgatcgctgg ctccacctcc ggctccggca agcccggctc cggcgagggc   1380

tccaccaagc ccggcgctag tatggcagaa atcggtactg gctttccatt cgacccccat   1440

tatgtggaag tcctgggcga gcgcatgcac tacgtcgatg ttggtccgcg cgatggcacc   1500

cctgtgctgt tcctgcacgg taacccgacc tcctcctacg tgtggcgcaa catcatcccg   1560

catgttgcac cgacccatcg ctgcattgct ccagacctga tcggtatggg caaatccgac   1620

aaaccagacc tgggttattt cttcgacgac cacgtccgct tcatggatgc cttcatcgaa   1680

gccctgggtc tggaagaggt cgtcctggtc attcacgact ggggctccgc tctgggtttc   1740
```

-continued cactgggcca agcgcaatcc agagcgcgtc aaaggtattg catttatgga gttcatccgc 1800
cctatcccga cctgggacga atggccagaa tttgcccgcg agaccttcca ggccttccgc 1860
accaccgacg tcggccgcaa gctgatcatc gatcagaacg tttttatcga gggtacgctg 1920
ccgatgggtg tcgtccgccc gctgactgaa gtcgagatgg accattaccg cgagccgttc 1980
ctgaatcctg ttgaccgcga gccactgtgg cgcttcccaa acgagctgcc aatcgccggt 2040
gagccagcga acatcgtcgc gctggtcgaa gaatacatgg actggctgca ccagtcccct 2100
gtcccgaagc tgctgttctg ggcaccccca ggcgttctga tcccaccggc cgaagccgct 2160
cgcctggcca aaagcctgcc taactgcaag gctgtggaca tcggcccggg tctgaatctg 2220
ctgcaagaag acaacccgga cctgatcggc agcgagatcg cgcgctggct gtctactctg 2280
gagatttccg gtctcgacgg ctccacctcc ggctccggca agcccggctc cggcgagggc 2340
tccaccaagc ccggcactag cgggattgga ggaccccgag gtgagaaagg gcaaaaggga 2400
gaaccagcca tcattgagcc ggggatgctg atcgaggggc cccctggccc tgaaggccct 2460
gctggtcttc caggacctcc aggaactaca ggtcctactg gccaaatggg tgaccctgga 2520
gaaaggggtc cccctgggcg cccaggtctt cctggagctg atggcttgcc tggcccccca 2580
ggtaccatgc tcatgctgcc gttccggttt ggaggcggtg gcgatgccgg ttctaagggc 2640
cccatggtct ctgcgcagga gtcccaggcc caggctatcc tccagcaagc caggttggca 2700
ctgaggggac cagctggccc aatgggtctc accgggagac ctggccccat gggtcctcct 2760
gggagtggcg gtttgaaagg tgagccagga gacatgggac ctcagggtcc tcgaggtgtg 2820
caaggcccac ctggcccaac agggaagcct ggaagacggg gccgtgctgg aagtgatgga 2880
gccagaggca tgcctggaca aacaggcccc aagggtgacc gtggctttga tggtctggct 2940
gggttgccgg gagagaaagg ccatagaggt gaccctggtc cttctggccc gcccggaatc 3000
ccaggagatg atggagaaag gggtgacgat ggagaagttg ggcccagggg actgcccggg 3060
gagcctggac cacgtggtct gcttgggcca aaaggccccc cagggcctcc tggacctcct 3120
ggtgtaacgg gtatggatgg ccagcctggc ccaaaaggaa atgtgggtcc ccagggagag 3180
cctgggccgc caggacagca gggtaatcct ggtgcccagg gtcttccagg tccccagggt 3240
gccattggtc ctccaggaga aaagggtcct ttggggaaac caggtctccc aggaatgcca 3300
ggcgctgatg gacccccggg gcaccctgga aaagaaggtc ctccaggaga gaaaggaggc 3360
cagggtcctc ctggccccca gggtcccatt ggctaccccg gtccacgagg agtcaagggg 3420
gcagatggca tccgaggtct gaagggcacc aagggggaga agggtgaaga cggcttccct 3480
gggtttaaag gcgacatggg aataaagggt gaccgggggg aaatcggccc acctggtccc 3540
cgaggagaag atggtcctga aggtccaaag ggtcgaggtg gtcccaatgg tgatcctggt 3600
cccctggggc ccactgggga aaagggaaag cttggcgtgc ccggattacc ggggtaccca 3660
ggaagacaag ggccaaaggg ttccattgga ttccctggct tcccgggcgc caacggagag 3720
aagggtggca gggggacacc tggaaagcca ggaccacggg gacagagagg cccaacgggc 3780
ccgcggggtg aacgaggccc acgaggcatc acggggaagc ctggccctaa gggcaactcc 3840
ggaggtgatg gcccagctgg ccctcctggt gaacggggac ccaacggacc ccaaggtccc 3900
accggctttc ctggacccaa gggtcccccg ggcccaccag gcaaggacgg actccctgga 3960
caccctgggc agagagggga gaccggtttc caaggcaaga ctggccctcc agggccccca 4020
ggagtggttg gccctcaggg tcccacagga gagacgggcc ccatgggtga gcgtggccat 4080
cctggtcctc caggccctcc tggtgaacag ggcctcccag gtgctgctgg gaaagaagga 4140

```
acgaagggtg acccaggtcc tgctggcctc cctgggaagg atggccctcc aggattgcgt   4200
ggattccctg gggaccgagg gctacctggc cccgtgggag cccttggact caaaggcagt   4260
gaaggccccc ctggcccacc aggtcctgcg ggttctccag gggagagagg accagctggt   4320
gccgctgggc ccatcggaat tccagggaga cctgggcctc agggacctcc ggggcctgct   4380
ggagagaaag gacttcctgg cgagaaaggt ccacaaggcc cagctggccg agatggcctc   4440
caaggtcccg tggggctccc tggaccagcc ggcccagtgg gtcctcctgg agaagatgga   4500
gataagggag agatcggaga gccagggcag aagggaagca agggcgacaa aggcgagcag   4560
ggtcctcctg ggcctaccgg tcctcaaggc ccgattggac agccaggccc ttcgggagca   4620
gatggtgaac ctggccctcg tggacagcag ggcctgtttg ggcagaaagg agatgaaggt   4680
tcaagaggtt tcccaggacc ccccgggcca gtgggattgc agggtttgcc aggacctcca   4740
ggagaaaagg gcgagacagg agacgtgggc cagatgggcc ctcctggtcc accaggcccc   4800
cgaggaccct ctggagctcc aggtgccgat ggaccacagg gtcctcctgg agggattggc   4860
aaccctggtg cagtcggaga aaagggagaa cctggtgaag ctggagatcc tggccttcca   4920
ggagaaggag gtcccctggg acctaaagga gaaagagggg agaagggaga ggctggcccc   4980
tctggtgctg ctggaccccc tggacccaaa ggccctcctg gagatgatgg ccccaaaggc   5040
agccctggcc ctgtgggctt tcctggagat cctggtcccc ctggagagcc aggccccgca   5100
ggtcaagacg gcccacctgg tgacaaaggg gacgatggtg aacctgggca gacggggtcc   5160
ccgggcccta ctggtgaacc tggtccatct gggcctccag gaaagagggg tcccccaggc   5220
cctgcaggcc ctgaaggcag gcagggggag aaaggagcca agggagaagc tggcttagaa   5280
ggccctcctg ggaagactgg ccccattggc ccccaagggg cccctgggaa gcctggcccc   5340
gatggtctcc gtggaatccc tggtcctgtg ggtgagcaag gcctcccagg atccccaggc   5400
cccgatggtc cacccggccc catgggtcct ccaggactcc ctggcctcaa aggagactcc   5460
ggtcccaaag gtgaaaaggg ccatccaggc ctgattggac tcatcggccc tccgggagag   5520
caaggtgaaa agggtgaccg tggactccca ggcccccagg gttcatctgg tcctaaagga   5580
gatcagggca tcacaggtcc ttctggccca cttgggcctc ctggtcctcc tggcttgccg   5640
ggccctccag gtcccaaagg tgctaagggc tcttcgggtc ccaccggccc gaagggtgag   5700
gcaggccacc caggactccc cggcccacct ggccctccgg gtgaggtcat ccagcccctg   5760
ccaatccagg cctccaggac tcggcggaac attgatgcca gccagctcct ggacgatggg   5820
gctggggaga gctacgtgga ttatgcagat ggcatggaag agatctttgg ttccctcaac   5880
tccctgaagc tggagattga acagatgaag cgaccactgg gcacccagca gaacccagcc   5940
cgtacctgca aggatctaca gctctgtcat cctgacttcc cagatggcga atactgggtc   6000
gatcccaacc aagggtgctc cagggactcc ttcaaagtct actgcaattt cacagctgga   6060
gggtccacgt gcgtcttccc tgacaagaag tctgagggaa gtaaaatggc ccggtggccc   6120
aaagaacagc cttccacctg gtatagtcag tacaagcggg gttccctgct ctcctatgtg   6180
gatgctgaag gcaaccccgt gggcgtggta caaatgacct tcctgcggct gctgagcgcc   6240
tctgcccacc agaacgtcac ctacaactgc taccagtccg tggcctggca ggatgccgcc   6300
acaggcagct atgataaggc tatccgcttc ttgggctcca acgatgagga aatgtcttat   6360
gataacaacc cctacatccg tgccctggtg gatggctgtg ctaccaagaa aggctaccag   6420
aagacggtgc tggagatcga cacgcccaaa gtagagcaag tccccattgt ggacatcatg   6480
```

```
ttcaacgact ttggcgaagc ctcacagaaa tttggatttg aagtggggcc agcttgcttc   6540

ctaggctag                                                           6549


<210> SEQ ID NO 4
<211> LENGTH: 2182
<212> TYPE: PRT
<213> ORGANISM: Artificial Sequence
<220> FEATURE:
<223> OTHER INFORMATION: synthetic peptide

<400> SEQUENCE: 4

Met Asp Val His Thr Arg Trp Lys Ala Ala Arg Pro Gly Ala Leu Leu
1               5                   10                  15

Leu Ser Ser Pro Leu Leu Leu Phe Leu Leu Leu Leu Trp Ala Pro Pro
            20                  25                  30

Ser Ser Arg Ala Ala Gln Pro Ala Asp Leu Leu Glu Met Leu Asp Phe
        35                  40                  45

His Asn Leu Pro Ser Gly Val Thr Lys Thr Thr Gly Phe Cys Ala Thr
    50                  55                  60

Arg Arg Ser Ser Ser Glu Pro Asp Val Ala Tyr Arg Val Ser Lys Asp
65                  70                  75                  80

Ala Gln Leu Ser Met Pro Thr Lys Gln Leu Tyr Pro Glu Ser Gly Phe
                85                  90                  95

Pro Glu Asp Phe Ser Ile Leu Thr Thr Val Lys Ala Lys Lys Gly Ser
            100                 105                 110

Gln Ala Phe Leu Val Ser Ile Tyr Asn Glu Gln Gly Ile Gln Gln Leu
        115                 120                 125

Gly Leu Glu Leu Gly Arg Ser Pro Val Phe Leu Tyr Glu Asp His Thr
    130                 135                 140

Gly Lys Pro Gly Pro Glu Glu Tyr Pro Leu Phe Pro Gly Ile Asn Leu
145                 150                 155                 160

Ser Asp Gly Lys Trp His Arg Ile Ala Leu Ser Val Tyr Lys Lys Asn
                165                 170                 175

Val Thr Leu Ile Leu Asp Cys Lys Lys Lys Ile Thr Lys Phe Leu Ser
            180                 185                 190

Arg Ser Asp His Pro Ile Ile Asp Thr Asn Gly Ile Val Met Phe Gly
        195                 200                 205

Ser Arg Ile Leu Asp Asp Glu Ile Phe Glu Gly Asp Ile Gln Gln Leu
    210                 215                 220

Leu Phe Val Ser Asp Asn Arg Ala Ala Tyr Asp Tyr Cys Glu His Tyr
225                 230                 235                 240

Ser Pro Asp Cys Asp Thr Ala Val Pro Asp Thr Pro Gln Ser Gln Asp
                245                 250                 255

Pro Asn Pro Asp Glu Tyr Tyr Pro Glu Gly Glu Gly Glu Thr Tyr Tyr
            260                 265                 270

Tyr Glu Tyr Pro Tyr Tyr Glu Asp Pro Glu Asp Pro Gly Lys Glu Pro
        275                 280                 285

Ala Pro Thr Gln Lys Pro Val Glu Ala Ala Arg Glu Thr Thr Glu Val
    290                 295                 300

Pro Glu Glu Gln Thr Gln Pro Leu Pro Glu Ala Pro Thr Val Pro Glu
305                 310                 315                 320

Thr Ser Asp Thr Ala Asp Lys Glu Asp Ser Leu Gly Ile Gly Asp Tyr
                325                 330                 335

Asp Tyr Val Pro Pro Asp Asp Tyr Tyr Thr Pro Pro Pro Tyr Glu Asp
            340                 345                 350
```

```
Phe Gly Tyr Gly Glu Gly Val Glu Asn Pro Asp Gln Pro Thr Asn Pro
        355                 360                 365

Asp Ser Gly Ala Glu Val Pro Thr Ser Thr Thr Val Thr Ser Asn Thr
    370                 375                 380

Ser Asn Pro Ala Pro Gly Glu Gly Lys Asp Asp Leu Gly Gly Glu Phe
385                 390                 395                 400

Thr Glu Glu Thr Ile Lys Asn Leu Glu Glu Asn Tyr Tyr Asp Pro Tyr
                405                 410                 415

Phe Asp Pro Asp Ser Asp Ser Ser Val Ser Pro Ser Glu Ile Gly Pro
            420                 425                 430

Gly Met Pro Ala Asn Gln Asp Thr Ile Phe Glu Ala Ile Ala Gly Ser
        435                 440                 445

Thr Ser Gly Ser Gly Lys Pro Gly Ser Gly Glu Gly Ser Thr Lys Pro
    450                 455                 460

Gly Ala Ser Met Ala Glu Ile Gly Thr Gly Phe Pro Phe Asp Pro His
465                 470                 475                 480

Tyr Val Glu Val Leu Gly Glu Arg Met His Tyr Val Asp Val Gly Pro
                485                 490                 495

Arg Asp Gly Thr Pro Val Leu Phe Leu His Gly Asn Pro Thr Ser Ser
            500                 505                 510

Tyr Val Trp Arg Asn Ile Ile Pro His Val Ala Pro Thr His Arg Cys
        515                 520                 525

Ile Ala Pro Asp Leu Ile Gly Met Gly Lys Ser Asp Lys Pro Asp Leu
    530                 535                 540

Gly Tyr Phe Phe Asp Asp His Val Arg Phe Met Asp Ala Phe Ile Glu
545                 550                 555                 560

Ala Leu Gly Leu Glu Glu Val Val Leu Val Ile His Asp Trp Gly Ser
                565                 570                 575

Ala Leu Gly Phe His Trp Ala Lys Arg Asn Pro Glu Arg Val Lys Gly
            580                 585                 590

Ile Ala Phe Met Glu Phe Ile Arg Pro Ile Pro Thr Trp Asp Glu Trp
        595                 600                 605

Pro Glu Phe Ala Arg Glu Thr Phe Gln Ala Phe Arg Thr Thr Asp Val
    610                 615                 620

Gly Arg Lys Leu Ile Ile Asp Gln Asn Val Phe Ile Glu Gly Thr Leu
625                 630                 635                 640

Pro Met Gly Val Val Arg Pro Leu Thr Glu Val Glu Met Asp His Tyr
                645                 650                 655

Arg Glu Pro Phe Leu Asn Pro Val Asp Arg Glu Pro Leu Trp Arg Phe
            660                 665                 670

Pro Asn Glu Leu Pro Ile Ala Gly Glu Pro Ala Asn Ile Val Ala Leu
        675                 680                 685

Val Glu Glu Tyr Met Asp Trp Leu His Gln Ser Pro Val Pro Lys Leu
    690                 695                 700

Leu Phe Trp Gly Thr Pro Gly Val Leu Ile Pro Pro Ala Glu Ala Ala
705                 710                 715                 720

Arg Leu Ala Lys Ser Leu Pro Asn Cys Lys Ala Val Asp Ile Gly Pro
                725                 730                 735

Gly Leu Asn Leu Leu Gln Glu Asp Asn Pro Asp Leu Ile Gly Ser Glu
            740                 745                 750

Ile Ala Arg Trp Leu Ser Thr Leu Glu Ile Ser Gly Leu Asp Gly Ser
        755                 760                 765
```

```
Thr Ser Gly Ser Gly Lys Pro Gly Ser Gly Glu Gly Ser Thr Lys Pro
    770                 775                 780

Gly Thr Ser Gly Ile Gly Gly Pro Arg Gly Glu Lys Gly Gln Lys Gly
785                 790                 795                 800

Glu Pro Ala Ile Ile Glu Pro Gly Met Leu Ile Glu Gly Pro Pro Gly
                805                 810                 815

Pro Glu Gly Pro Ala Gly Leu Pro Gly Pro Pro Gly Thr Thr Gly Pro
            820                 825                 830

Thr Gly Gln Met Gly Asp Pro Gly Glu Arg Gly Pro Pro Gly Arg Pro
        835                 840                 845

Gly Leu Pro Gly Ala Asp Gly Leu Pro Gly Pro Pro Gly Thr Met Leu
    850                 855                 860

Met Leu Pro Phe Arg Phe Gly Gly Gly Gly Asp Ala Gly Ser Lys Gly
865                 870                 875                 880

Pro Met Val Ser Ala Gln Glu Ser Gln Ala Gln Ala Ile Leu Gln Gln
                885                 890                 895

Ala Arg Leu Ala Leu Arg Gly Pro Ala Gly Pro Met Gly Leu Thr Gly
            900                 905                 910

Arg Pro Gly Pro Met Gly Pro Pro Gly Ser Gly Gly Leu Lys Gly Glu
        915                 920                 925

Pro Gly Asp Met Gly Pro Gln Gly Pro Arg Gly Val Gln Gly Pro Pro
    930                 935                 940

Gly Pro Thr Gly Lys Pro Gly Arg Arg Gly Arg Ala Gly Ser Asp Gly
945                 950                 955                 960

Ala Arg Gly Met Pro Gly Gln Thr Gly Pro Lys Gly Asp Arg Gly Phe
                965                 970                 975

Asp Gly Leu Ala Gly Leu Pro Gly Glu Lys Gly His Arg Gly Asp Pro
            980                 985                 990

Gly Pro Ser Gly Pro Pro Gly Ile  Pro Gly Asp Asp Gly  Glu Arg Gly
        995                 1000                1005

Asp Asp  Gly Glu Val Gly Pro  Arg Gly Leu Pro Gly  Glu Pro Gly
    1010                1015                1020

Pro Arg  Gly Leu Leu Gly Pro  Lys Gly Pro Pro Gly  Pro Pro Gly
    1025                1030                1035

Pro Pro  Gly Val Thr Gly Met  Asp Gly Gln Pro Gly  Pro Lys Gly
    1040                1045                1050

Asn Val  Gly Pro Gln Gly Glu  Pro Gly Pro Pro Gly  Gln Gln Gly
    1055                1060                1065

Asn Pro  Gly Ala Gln Gly Leu  Pro Gly Pro Gln Gly  Ala Ile Gly
    1070                1075                1080

Pro Pro  Gly Glu Lys Gly Pro  Leu Gly Lys Pro Gly  Leu Pro Gly
    1085                1090                1095

Met Pro  Gly Ala Asp Gly Pro  Pro Gly His Pro Gly  Lys Glu Gly
    1100                1105                1110

Pro Pro  Gly Glu Lys Gly Gly  Gln Gly Pro Pro Gly  Pro Gln Gly
    1115                1120                1125

Pro Ile  Gly Tyr Pro Gly Pro  Arg Gly Val Lys Gly  Ala Asp Gly
    1130                1135                1140

Ile Arg  Gly Leu Lys Gly Thr  Lys Gly Glu Lys Gly  Glu Asp Gly
    1145                1150                1155

Phe Pro  Gly Phe Lys Gly Asp  Met Gly Ile Lys Gly  Asp Arg Gly
    1160                1165                1170

Glu Ile  Gly Pro Pro Gly Pro  Arg Gly Glu Asp Gly  Pro Glu Gly
```

```
    1175                1180                1185

Pro Lys  Gly Arg Gly Gly Pro  Asn Gly Asp Pro Gly  Pro Leu Gly
    1190                1195                1200

Pro Thr  Gly Glu Lys Gly Lys  Leu Gly Val Pro Gly  Leu Pro Gly
    1205                1210                1215

Tyr Pro  Gly Arg Gln Gly Pro  Lys Gly Ser Ile Gly  Phe Pro Gly
    1220                1225                1230

Phe Pro  Gly Ala Asn Gly Glu  Lys Gly Gly Arg Gly  Thr Pro Gly
    1235                1240                1245

Lys Pro  Gly Pro Arg Gly Gln  Arg Gly Pro Thr Gly  Pro Arg Gly
    1250                1255                1260

Glu Arg  Gly Pro Arg Gly Ile  Thr Gly Lys Pro Gly  Pro Lys Gly
    1265                1270                1275

Asn Ser  Gly Gly Asp Gly Pro  Ala Gly Pro Pro Gly  Glu Arg Gly
    1280                1285                1290

Pro Asn  Gly Pro Gln Gly Pro  Thr Gly Phe Pro Gly  Pro Lys Gly
    1295                1300                1305

Pro Pro  Gly Pro Pro Gly Lys  Asp Gly Leu Pro Gly  His Pro Gly
    1310                1315                1320

Gln Arg  Gly Glu Thr Gly Phe  Gln Gly Lys Thr Gly  Pro Pro Gly
    1325                1330                1335

Pro Pro  Gly Val Val Gly Pro  Gln Gly Pro Thr Gly  Glu Thr Gly
    1340                1345                1350

Pro Met  Gly Glu Arg Gly His  Pro Gly Pro Pro Gly  Pro Pro Gly
    1355                1360                1365

Glu Gln  Gly Leu Pro Gly Ala  Ala Gly Lys Glu Gly  Thr Lys Gly
    1370                1375                1380

Asp Pro  Gly Pro Ala Gly Leu  Pro Gly Lys Asp Gly  Pro Pro Gly
    1385                1390                1395

Leu Arg  Gly Phe Pro Gly Asp  Arg Gly Leu Pro Gly  Pro Val Gly
    1400                1405                1410

Ala Leu  Gly Leu Lys Gly Ser  Glu Gly Pro Pro Gly  Pro Pro Gly
    1415                1420                1425

Pro Ala  Gly Ser Pro Gly Glu  Arg Gly Pro Ala Gly  Ala Ala Gly
    1430                1435                1440

Pro Ile  Gly Ile Pro Gly Arg  Pro Gly Pro Gln Gly  Pro Pro Gly
    1445                1450                1455

Pro Ala  Gly Glu Lys Gly Leu  Pro Gly Glu Lys Gly  Pro Gln Gly
    1460                1465                1470

Pro Ala  Gly Arg Asp Gly Leu  Gln Gly Pro Val Gly  Leu Pro Gly
    1475                1480                1485

Pro Ala  Gly Pro Val Gly Pro  Pro Gly Glu Asp Gly  Asp Lys Gly
    1490                1495                1500

Glu Ile  Gly Glu Pro Gly Gln  Lys Gly Ser Lys Gly  Asp Lys Gly
    1505                1510                1515

Glu Gln  Gly Pro Pro Gly Pro  Thr Gly Pro Gln Gly  Pro Ile Gly
    1520                1525                1530

Gln Pro  Gly Pro Ser Gly Ala  Asp Gly Glu Pro Gly  Pro Arg Gly
    1535                1540                1545

Gln Gln  Gly Leu Phe Gly Gln  Lys Gly Asp Glu Gly  Ser Arg Gly
    1550                1555                1560

Phe Pro  Gly Pro Pro Gly Pro  Val Gly Leu Gln Gly  Leu Pro Gly
    1565                1570                1575
```

-continued

```
Pro Pro  Gly Glu Lys Gly Glu  Thr Gly Asp Val Gly  Gln Met Gly
    1580                 1585                 1590

Pro Pro  Gly Pro Pro Gly Pro  Arg Gly Pro Ser Gly  Ala Pro Gly
    1595                 1600                 1605

Ala Asp  Gly Pro Gln Gly Pro  Pro Gly Gly Ile Gly  Asn Pro Gly
    1610                 1615                 1620

Ala Val  Gly Glu Lys Gly Glu  Pro Gly Glu Ala Gly  Asp Pro Gly
    1625                 1630                 1635

Leu Pro  Gly Glu Gly Gly Pro  Leu Gly Pro Lys Gly  Glu Arg Gly
    1640                 1645                 1650

Glu Lys  Gly Glu Ala Gly Pro  Ser Gly Ala Ala Gly  Pro Pro Gly
    1655                 1660                 1665

Pro Lys  Gly Pro Pro Gly Asp  Asp Gly Pro Lys Gly  Ser Pro Gly
    1670                 1675                 1680

Pro Val  Gly Phe Pro Gly Asp  Pro Gly Pro Pro Gly  Glu Pro Gly
    1685                 1690                 1695

Pro Ala  Gly Gln Asp Gly Pro  Pro Gly Asp Lys Gly  Asp Asp Gly
    1700                 1705                 1710

Glu Pro  Gly Gln Thr Gly Ser  Pro Gly Pro Thr Gly  Glu Pro Gly
    1715                 1720                 1725

Pro Ser  Gly Pro Pro Gly Lys  Arg Gly Pro Pro Gly  Pro Ala Gly
    1730                 1735                 1740

Pro Glu  Gly Arg Gln Gly Glu  Lys Gly Ala Lys Gly  Glu Ala Gly
    1745                 1750                 1755

Leu Glu  Gly Pro Pro Gly Lys  Thr Gly Pro Ile Gly  Pro Gln Gly
    1760                 1765                 1770

Ala Pro  Gly Lys Pro Gly Pro  Asp Gly Leu Arg Gly  Ile Pro Gly
    1775                 1780                 1785

Pro Val  Gly Glu Gln Gly Leu  Pro Gly Ser Pro Gly  Pro Asp Gly
    1790                 1795                 1800

Pro Pro  Gly Pro Met Gly Pro  Pro Gly Leu Pro Gly  Leu Lys Gly
    1805                 1810                 1815

Asp Ser  Gly Pro Lys Gly Glu  Lys Gly His Pro Gly  Leu Ile Gly
    1820                 1825                 1830

Leu Ile  Gly Pro Pro Gly Glu  Gln Gly Glu Lys Gly  Asp Arg Gly
    1835                 1840                 1845

Leu Pro  Gly Pro Gln Gly Ser  Ser Gly Pro Lys Gly  Asp Gln Gly
    1850                 1855                 1860

Ile Thr  Gly Pro Ser Gly Pro  Leu Gly Pro Pro Gly  Pro Pro Gly
    1865                 1870                 1875

Leu Pro  Gly Pro Pro Gly Pro  Lys Gly Ala Lys Gly  Ser Ser Gly
    1880                 1885                 1890

Pro Thr  Gly Pro Lys Gly Glu  Ala Gly His Pro Gly  Leu Pro Gly
    1895                 1900                 1905

Pro Pro  Gly Pro Pro Gly Glu  Val Ile Gln Pro Leu  Pro Ile Gln
    1910                 1915                 1920

Ala Ser  Arg Thr Arg Arg Asn  Ile Asp Ala Ser Gln  Leu Leu Asp
    1925                 1930                 1935

Asp Gly  Ala Gly Glu Ser Tyr  Val Asp Tyr Ala Asp  Gly Met Glu
    1940                 1945                 1950

Glu Ile  Phe Gly Ser Leu Asn  Ser Leu Lys Leu Glu  Ile Glu Gln
    1955                 1960                 1965
```

```
Met Lys  Arg Pro Leu Gly Thr  Gln Gln Asn Pro Ala  Arg Thr Cys
    1970                 1975                 1980

Lys Asp  Leu Gln Leu Cys His  Pro Asp Phe Pro Asp  Gly Glu Tyr
    1985                 1990                 1995

Trp Val  Asp Pro Asn Gln Gly  Cys Ser Arg Asp Ser  Phe Lys Val
    2000                 2005                 2010

Tyr Cys  Asn Phe Thr Ala Gly  Gly Ser Thr Cys Val  Phe Pro Asp
    2015                 2020                 2025

Lys Lys  Ser Glu Gly Ser Lys  Met Ala Arg Trp Pro  Lys Glu Gln
    2030                 2035                 2040

Pro Ser  Thr Trp Tyr Ser Gln  Tyr Lys Arg Gly Ser  Leu Leu Ser
    2045                 2050                 2055

Tyr Val  Asp Ala Glu Gly Asn  Pro Val Gly Val Val  Gln Met Thr
    2060                 2065                 2070

Phe Leu  Arg Leu Leu Ser Ala  Ser Ala His Gln Asn  Val Thr Tyr
    2075                 2080                 2085

Asn Cys  Tyr Gln Ser Val Ala  Trp Gln Asp Ala Ala  Thr Gly Ser
    2090                 2095                 2100

Tyr Asp  Lys Ala Ile Arg Phe  Leu Gly Ser Asn Asp  Glu Glu Met
    2105                 2110                 2115

Ser Tyr  Asp Asn Asn Pro Tyr  Ile Arg Ala Leu Val  Asp Gly Cys
    2120                 2125                 2130

Ala Thr  Lys Lys Gly Tyr Gln  Lys Thr Val Leu Glu  Ile Asp Thr
    2135                 2140                 2145

Pro Lys  Val Glu Gln Val Pro  Ile Val Asp Ile Met  Phe Asn Asp
    2150                 2155                 2160

Phe Gly  Glu Ala Ser Gln Lys  Phe Gly Phe Glu Val  Gly Pro Ala
    2165                 2170                 2175

Cys Phe  Leu Gly
    2180
```

<210> SEQ ID NO 5
<211> LENGTH: 16140
<212> TYPE: DNA
<213> ORGANISM: Artificial Sequence
<220> FEATURE:
<223> OTHER INFORMATION: synthetic polynucleotide

<400> SEQUENCE: 5

```
tagttattaa tagtaatcaa ttacggggtc attagttcat agcccatata tggagttccg     60

cgttacataa cttacggtaa atggcccgcc tggctgaccg cccaacgacc cccgcccatt    120

gacgtcaata atgacgtatg ttcccatagt aacgccaata gggactttcc attgacgtca    180

atgggtggag tatttacggt aaactgccca cttggcagta catcaagtgt atcatatgcc    240

aagtacgccc cctattgacg tcaatgacgg taaatggccc gcctggcatt atgcccagta    300

catgacctta tgggactttc ctacttggca gtacatctac gtattagtca tcgctattac    360

catggtgatg cggttttggc agtacatcaa tgggcgtgga tagcggtttg actcacgggg    420

atttccaagt ctccacccca ttgacgtcaa tgggagtttg ttttggcacc aaaatcaacg    480

ggactttcca aaatgtcgta acaactccgc cccattgacg caaatgggcg gtaggcgtgt    540

acggtgggag gtctatataa gcagagctgg tttagtgaac cgtcagatcc gctagcctgg    600

cttgaggctc aggacgcaaa tcttgaggat gttcagcggg agttttccgg gctgcgagta    660

attggtgatg aggacgagga tggttcggag gatggggaat tttcagacct ggatctgtct    720
```

-continued

```
gacagcgacc atgaagggga tgagggtggg ggggctgttg gagggggcag gagtctgcac    780
tccctgtatt cactgagcgt cgtctaataa agatgtctat tgatctcttt tagtgtgaat    840
catgtctgac gaggggccag gtacaggacc tggaaatggc ctaggagaga agggagacac    900
atctggacca gaaggctccg gcggcagtgg acctcaaaga agagggggtg ataaccatgg    960
acgaggacgg ggaagaggac gaggacgagg aggcggaaga ccaggagccc cgggcggctc   1020
aggatcaggg ccaagacata gagatggtgt ccggagaccc caaaaacgtc caagttgcat   1080
tggctgcaaa gggacccacg gtggaacagg agcaggagca ggagcgggag gggcaggagc   1140
aggaggggca ggagcaggag gaggggcagg agcaggagga ggggcaggag gggcaggagg   1200
ggcaggaggg gcaggagcag gaggaggggc aggagcagga ggaggggcag gaggggcagg   1260
aggggcagga gcaggaggag gggcaggagc aggaggaggg gcaggagggg caggagcagg   1320
aggaggggca ggaggggcag gaggggcagg agcaggagga ggggcaggag caggaggagg   1380
ggcaggaggg gcaggagcag gaggaggggc aggaggggca ggaggggcag gagcaggagg   1440
aggggcagga gcaggagggg caggaggggc aggaggggca ggagcaggag gggcaggagc   1500
aggaggaggg gcaggagggg caggaggggc aggagcagga ggggcaggag caggaggggc   1560
aggagcagga ggggcaggag caggaggggc aggaggggca ggagcaggag gggcaggagg   1620
ggcaggagca ggaggggcag gaggggcagg agcaggagga ggggcaggag gggcaggagc   1680
aggaggaggg gcaggagggg caggagcagg aggggcagga ggggcaggag caggaggggc   1740
aggaggggca ggagcaggag gggcaggagg ggcaggagca ggaggagggg caggagcagg   1800
aggggcagga gcaggaggtg gaggccgggg tcgaggaggc agtggaggcc ggggtcgagg   1860
aggtagtgga ggccggggtc gaggaggtag tggaggccgc cggggtagag gacgtgaaag   1920
agccaggggg ggaagtcgtg aaagagccag ggggagaggt cgtggacgtg gagaaaagag   1980
gcccaggagt cccagtagtc agtcatcatc atccgggtct ccaccgcgca ggccccctcc   2040
aggtagaagg ccatttttcc accctgtagg ggaagccgat tattttgaat accaccaaga   2100
aggtggccca gatggtgagc ctgacgtgcc cccgggagcg atagagcagg gccccgcaga   2160
tgacccagga gaaggcccaa gcactggacc ccggggtcag ggtgatggag gcaggcgcaa   2220
aaaaggaggg tggtttggaa agcatcgtgg tcaaggaggt tccaacccga aatttgagaa   2280
cattgcagaa ggtttaagag ctctcctggc taggagtcac gtagaaagga ctaccgacga   2340
aggaacttgg gtcgccggtg tgttcgtata tggaggtagt aagacctccc tttacaacct   2400
aaggcgagga actgcccttg ctattccaca atgtcgtctt acaccattga gtcgtctccc   2460
ctttggaatg gcccctggac ccggcccaca acctggcccg ctaagggagt ccattgtctg   2520
ttatttcatg gtctttttac aaactcatat atttgctgag gttttgaagg atgcgattaa   2580
ggaccttgtt atgacaaagc ccgctcctac ctgcaatatc agggtgactg tgtgcagctt   2640
tgacgatgga gtagatttgc ctccctggtt tccacctatg gtggaagggg ctgccgcgga   2700
gggtgatgac ggagatgacg gagatgaagg aggtgatgga gatgagggtg aggaagggca   2760
ggagtgatgt aacttgttag gagacgccct caatcgtatt aaaagccgtg tattcccccg   2820
cactaaagaa taaatcccca gtagacatca tgcgtgctgt tggtgtattt ctggccatct   2880
gtcttgtcac catttcgtc ctcccaacat ggggcaattg ggcataccca tgttgtcacg   2940
tcactcagct ccgcgctcaa caccttctcg cgttggaaaa cattagcgac atttacctgg   3000
tgagcaatca gacatgcgac ggctttagcc tggcctcctt aaattcacct aagaatggga   3060
gcaaccagca ggaaaaggac aagcagcgaa aattcacgcc cccttgggag gtggcggcat   3120
```

```
atgcaaagga tagcactccc actctactac tgggtatcat atgctgactg tatatgcatg   3180
aggatagcat atgctacccg gatacagatt aggatagcat atactaccca gatatagatt   3240
aggatagcat atgctaccca gatatagatt aggatagcct atgctaccca gatataaatt   3300
aggatagcat atactaccca gatatagatt aggatagcat atgctaccca gatatagatt   3360
aggatagcct atgctaccca gatatagatt aggatagcat atgctaccca gatatagatt   3420
aggatagcat atgctatcca gatatttggg tagtatatgc tacccagata taaattagga   3480
tagcatatac taccctaatc tctattagga tagcatatgc tacccggata cagattagga   3540
tagcatatac tacccagata tagattagga tagcatatgc tacccagata tagattagga   3600
tagcctatgc tacccagata taaattagga tagcatatac tacccagata tagattagga   3660
tagcatatgc tacccagata tagattagga tagcctatgc tacccagata tagattagga   3720
tagcatatgc tatccagata tttgggtagt atatgctacc catggcaaca ttagcccacc   3780
gtgctctcag cgacctcgtg aatatgagga ccaacaaccc tgtgcttggc gctcaggcgc   3840
aagtgtgtgt aatttgtcct ccagatcgca gcaatcgcgc ccctatcttg gcccgcccac   3900
ctacttatgc aggtattccc cggggtgcca ttagtggttt tgtgggcaag tggtttgacc   3960
gcagtggtta gcggggttac aatcagccaa gttattacac ccttatttta cagtccaaaa   4020
ccgcagggcg gcgtgtgggg gctgacgcga tcgctgttcc ttaggaccct tttactaacc   4080
ctaattcgat agcatatgct tcccgttggg taacatatgc tattgaatta gggttagtct   4140
ggatagtata tactactacc cgggaagcat atgctacccg tttagggtta acaagggggc   4200
cttataaaca ctattgctaa tgccctcttg agggtccgct tatcggtagc tacacaggcc   4260
cctctgattg acgttggtgt agcctcccgt agtcttcctg ggcccctggg aggtacatgt   4320
cccccagcat tggtgtaaga gcttcagcca agagttacac ataaaggcaa tgttgtgttg   4380
cagtccacag actgcaaagt ctgctccagg atgaaagcca ctcagtgttg gcaaatgtgc   4440
acatccattt ataaggatgt caactacagt cagagaaccc ctttgtgttt ggtccccccc   4500
cgtgtcacat gtggaacagg gcccagttgg caagttgtac caaccaactg aagggattac   4560
atgcactgcc ccgtgaccaa tacaaaacaa aagcgctcct cgtaccagcg aagaaggggc   4620
agagatgccg tagtcaggtt tagttcgtcc ggcggcggga tctcgacatt gattattgac   4680
tagttattaa tartaatcaa ttacggggtc attagttcat agcccatata tggagttccg   4740
cgttacataa cttacggtaa atggcccgcc tggctgaccg cccaacgacc cccgcccatt   4800
gacgtcaata atgacgtatg ttcccatagt aacgccaata gggactttcc attgacgtca   4860
atgggtggac tatttacggt aaactgccca cttggcagta catcaagtgt atcatatgcc   4920
aagtacgccc cctattgacg tcaatgacgg taaatggccc gcctggcatt atgcccagta   4980
catgacctta tgggactttc ctacttggca gtacatctac gtattagtca tcgctattac   5040
catgggtcga ggtgagcccc acgttctgct tcactctccc catctccccc ccctccccac   5100
ccccaatttt gtatttattt atttttaat tattttgtgc agcgatgggg gcgggggggg   5160
ggggggcgcg cgccaggcgg ggcggggcgg ggcgaggggc ggggcggggc gaggcggaga   5220
ggtgcggcgg cagccaatca gagcggcgcg ctccgaaagt ttcctttat ggcgaggcgg   5280
cggcggcggc ggccctataa aaagcgaagc gcgcggcggg cgggagtcgc tgcgttgcct   5340
tcgccccgtg ccccgctccg cgccgcctcg cgccgcccgc cccggctctg actgaccgcg   5400
ttactcccac aggtgagcgg gcgggacggc ccttctcctc cgggctgtaa ttagcgcttg   5460
```

-continued

```
gtttaatgac ggctcgtttc ttttctgtgg ctgcgtgaaa gccttaaagg gctccgggag   5520
ggccctttgt gcggggggga gcggctcggg gggtgcgtgc gtgtgtgtgt gcgtggggag   5580
cgccgcgtgc ggcccgcgct gcccggcggc tgtgagcgct gcgggcgcgg cgcggggctt   5640
tgtgcgctcc gcgtgtgcgc gaggggagcg cggccggggg cggtgccccg cggtgcgggg   5700
gggctgcgag gggaacaaag gctgcgtgcg gggtgtgtgc gtgggggggt gagcaggggg   5760
tgtgggcgcg gcggtcgggc tgtaaccccc ccctgcaccc ccctccccga gttgctgagc   5820
acggcccggc ttcgggtgcg gggctccgtg cggggcgtgg cgcggggctc gccgtgccgg   5880
gcgggggggtg gcggcaggtg gggggtgccgg gcggggcggg gccgcctcgg gccggggagg   5940
gctcggggga ggggcgcggc ggccccggag cgccggcggc tgtcgaggcg cggcgagccg   6000
cagccattgc cttttatggt aatcgtgcga gagggcgcag ggacttcctt tgtcccaaat   6060
ctggcggagc cgaaatctgg gaggcgccgc cgcacccccct ctagcgggcg cgggcgaagc   6120
ggtgcggcgc cggcaggaag gaaatgggcg gggagggcct tcgtgcgtcg ccgcgccgcc   6180
gtccccttct ccatctccag cctcggggct gccgcagggg gacggctgcc ttcggggggg   6240
acggggcagg gcggggttcg gcttctggcg tgtgaccggc ggctctagag cctctgctaa   6300
ccatgttcat gccttcttct ttttcctaca gctcctgggc aacgtgctgg ttgttgtgct   6360
gtctcatcat tttggcaaag aattaaccct cactaaaggg taccgggccc cccctcgagg   6420
tcgaccgccg gcatggacgt acacacccgc tggaaagctg cgcgcccagg cgccctgctg   6480
ctgtcttcgc cgctactcct gttcctgctg ctgctgtggg cgccgccttc gagccgcgca   6540
gctcagccag cagatcttct ggagatgcta gattttcaca atttgccctc aggggtaacg   6600
aaaaccacag gtttctgtgc tactcgaaga tcttccagcg agccggatgt tgcctaccga   6660
gtctctaaag atgcacagct cagcatgccc accaagcagc tgtaccctga gtctggtttt   6720
cccgaggact tctccatcct gacaaccgtg aaagccaaga aaggcagcca ggccttccta   6780
gtctccattt acaatgagca gggcatccag cagttggggc tggagctggg ccgctcccct   6840
gtcttcctct atgaggacca cacagggaag cccgggcctg aagagtatcc gcttttccct   6900
ggcatcaact tgtccgatgg caagtggcac cgaattgctc tcagtgtcta caagaaaaat   6960
gtcaccttga tcctcgactg taagaagaag attacgaagt tcctcagccg cagtgaccac   7020
cccataatag acaccaatgg gattgtcatg tttggctccc ggattctgga tgatgaaata   7080
tttgagggtg acatccaaca gttgcttttc gtctctgaca accgagctgc ctatgactac   7140
tgtgagcact acagccccga ctgtgacact gcggtccctg acacacctca gtcacaggac   7200
cctaacccgg atgaatatta cccagaagga gagggtgaga cctattacta tgagtatcca   7260
tattatgaag accctgaaga cccgggaaag gagcctgccc ctactcagaa gccagtggaa   7320
gctgccagag aaaccacaga ggttcctgag gagcagaccc agcccctacc cgaagcccct   7380
acagtgcctg agaccagtga cacggctgac aaggaggaca gtctagggat cggggactat   7440
gactacgtgc ccccagatga ctattacact ccaccccccat atgaagactt tggatatggc   7500
gagggtgtgg agaaccctga ccagcccacc aaccccgact caggggctga ggtccccacc   7560
agcaccactg ttacctccaa cacctccaat ccagctccag gagaagggaa ggatgacctg   7620
ggcggcgaat tcaccgagga aaccatcaag aatctagagg aaaactacta tgacccgtac   7680
tttgaccccg actccgactc cagtgtctct ccatcagaga tagggccagg catgcccgct   7740
aaccaggaca ccatctttga ggcgatcgct ggctccacct ccggctccgg caagcccggc   7800
tccggcgagg gctccaccaa gcccggcgct agtatggtga gcaagggcga ggagctgttc   7860
```

```
accggggtgg tgcccatcct ggtcgagctg gacggcgacg taaacggcca caagttcagc   7920
gtgtccggcg agggcgaggg cgatgccacc tacggcaagc tgaccctgaa gttcatctgc   7980
accaccggca agctgcccgt gccctggccc accctcgtga ccaccctgac ctacggcgtg   8040
cagtgcttca gccgctaccc cgaccacatg aagcagcacg acttcttcaa gtccgccatg   8100
cccgaaggct acgtccagga gcgcaccatc ttcttcaagg acgacggcaa ctacaagacc   8160
cgcgccgagg tgaagttcga gggcgacacc ctggtgaacc gcatcgagct gaagggcatc   8220
gacttcaagg aggacggcaa catcctgggg cacaagctgg agtacaacta caacagccac   8280
aacgtctata tcatggccga caagcagaag aacggcatca aggtgaactt caagatccgc   8340
cacaacatcg aggacggcag cgtgcagctc gccgaccact accagcagaa cacccccatc   8400
ggcgacggcc ccgtgctgct gcccgacaac cactacctga gcacccagtc cgccctgagc   8460
aaagacccca acgagaagcg cgatcacatg gtcctgctgg agttcgtgac cgccgccggg   8520
atcactctcg gcatggacga gctgtacaag ctcgacggct ccacctccgg ctccggcaag   8580
cccggctccg gcgagggctc caccaagccc ggcactagcg ggattggagg accccgaggt   8640
gagaaagggc aaaagggaga accagccatc attgagccgg ggatgctgat cgagggggcc   8700
cctggccctg aaggccctgc tggtcttcca ggacctccag gaactacagg tcctactggc   8760
caaatgggtg accctggaga aaggggtccc cctgggcgcc caggtcttcc tggagctgat   8820
ggcttgcctg gcccccccagg taccatgctc atgctgccgt tccggtttgg aggcggtggc   8880
gatgccggtt ctaagggccc catggtctct gcgcaggagt cccaggccca ggctatcctc   8940
cagcaagcca ggttggcact gaggggacca gctggcccaa tgggtctcac cgggagacct   9000
ggccccatgg gtcctcctgg gagtggcggt ttgaaaggtg agccaggaga catgggacct   9060
cagggtcctc gaggtgtgca aggcccacct ggcccaacag ggaagcctgg aagacggggc   9120
cgtgctggaa gtgatggagc cagaggcatg cctggacaaa caggccccaa gggtgaccgt   9180
ggctttgatg gtctggctgg gttgccggga gagaaaggcc atagaggtga ccctggtcct   9240
tctggcccgc ccggaatccc aggagatgat ggagagaaagg gtgacgatgg agaagttggg   9300
cccaggggac tgcccgggga gcctggacca cgtggtctgc ttgggccaaa aggcccccca   9360
gggcctcctg gacctcctgg tgtaacgggt atggatggcc agcctggccc aaaaggaaat   9420
gtgggtcccc agggagagcc tgggccgcca ggacagcagg gtaatcctgg tgcccagggt   9480
cttccaggtc cccagggtgc cattggtcct ccaggagaaa agggtccttt ggggaaacca   9540
ggtctcccag gaatgccagg cgctgatgga cccccggggc accctggaaa agaaggtcct   9600
ccaggagaga aaggaggcca gggtcctcct ggcccccagg gtcccattgg ctaccccggt   9660
ccacgaggag tcaagggggc agatggcatc cgaggtctga agggcaccaa gggggagaag   9720
ggtgaagacg gcttccctgg gtttaaaggc gacatgggaa taaagggtga ccggggggaa   9780
atcggcccac ctggtccccg aggagaagat ggtcctgaag gtccaaaggg tcgaggtggt   9840
cccaatggtg atcctggtcc cctggggccc actggggaaa agggaaagct tggcgtgccc   9900
ggattaccgg ggtacccagg aagacaaggg ccaaagggtt ccattggatt ccctggcttc   9960
ccgggcgcca acggagagaa gggtggcagg gggacacctg gaaagccagg accacgggga   10020
cagagaggcc caacgggccc gcggggtgaa cgaggcccac gaggcatcac ggggaagcct   10080
ggccctaagg gcaactccgg aggtgatggc ccagctggcc ctcctggtga acggggaccc   10140
aacggacccc aaggtcccac cggctttcct ggacccaagg gtcccccggg cccaccaggc   10200
```

-continued

```
aaggacggac tccctggaca ccctgggcag agaggggaga ccggtttcca aggcaagact  10260
ggccctccag ggcccccagg agtggttggc cctcagggtc ccacaggaga gacgggcccc  10320
atgggtgagc gtggccatcc tggtcctcca ggccctcctg gtgaacaggg cctcccaggt  10380
gctgctggga aagaaggaac gaagggtgac ccaggtcctg ctggcctccc tgggaaggat  10440
ggccctccag gattgcgtgg attccctggg gaccgagggc tacctggccc cgtgggagcc  10500
cttggactca aggcagtgga aggccccccct ggcccaccag gtcctgcggg ttctccaggg  10560
gagagaggac cagctggtgc cgctgggccc atcggaattc cagggagacc tgggcctcag  10620
ggacctccgg ggcctgctgg agagaaagga cttcctggcg agaaaggtcc acaaggccca  10680
gctggccgag atggcctcca aggtcccgtg gggctccctg gaccagccgg cccagtgggt  10740
cctcctggag aagatggaga taagggagag atcggagagc cagggcagaa gggaagcaag  10800
ggcgacaaag gcgagcaggg tcctcctggg cctaccggtc ctcaaggccc gattggacag  10860
ccaggccctt cgggagcaga tggtgaacct ggccctcgtg gacagcaggg cctgtttggg  10920
cagaaaggag atgaaggttc aagaggtttc ccaggacccc ccgggccagt gggattgcag  10980
ggtttgccag gacctccagg agaaaagggc gagacaggag acgtgggcca gatgggccct  11040
cctggtccac caggcccccg aggaccctct ggagctccag gtgccgatgg accacagggt  11100
cctcctggag ggattggcaa ccctggtgca gtcggagaaa agggagaacc tggtgaagct  11160
ggagatcctg gccttccagg agaaggaggt cccctgggac ctaaaggaga aagaggggag  11220
aagggagagg ctggcccctc tggtgctgct ggacccccctg gacccaaagg ccctcctgga  11280
gatgatggcc ccaaaggcag ccctggccct gtgggctttc ctggagatcc tggtccccct  11340
ggagagccag gccccgcagg tcaagacggc ccacctggtg acaaagggga cgatggtgaa  11400
cctgggcaga cggggtcccc gggccctact ggtgaacctg gtccatctgg gcctccagga  11460
aagaggggtc ccccaggccc tgcaggccct gaaggcaggc agggggagaa aggagccaag  11520
ggagaagctg gcttagaagg ccctcctggg aagactggcc ccattggccc ccaaggggcc  11580
cctgggaagc ctggccccga tggtctccgt ggaatccctg gtcctgtggg tgagcaaggc  11640
ctcccaggat ccccaggccc cgatggtcca cccggcccca tgggtcctcc aggactccct  11700
ggcctcaaag gagactccgg tcccaaaggt gaaaagggcc atccaggcct gattggactc  11760
atcggccctc cgggagagca aggtgaaaag ggtgaccgtg gactcccagg cccccagggt  11820
tcatctggtc ctaaaggaga tcagggcatc acaggtcctt ctggcccact tgggcctcct  11880
ggtcctcctg gcttgccggg ccctccaggt cccaaaggtg ctaagggctc ttcgggtccc  11940
accggcccga agggtgaggc aggccaccca ggactccccg gcccacctgg ccctccgggt  12000
gaggtcatcc agcccctgcc aatccaggcc tccaggactc ggcggaacat tgatgccagc  12060
cagctcctgg acgatggggc tggggagagc tacgtggatt atgcagatgg catggaagag  12120
atctttggtt ccctcaactc cctgaagctg gagattgaac agatgaagcg accactgggc  12180
acccagcaga acccagcccg tacctgcaag gatctacagc tctgtcatcc tgacttccca  12240
gatggcgaat actgggtcga tcccaaccaa gggtgctcca gggactcctt caaagtctac  12300
tgcaatttca cagctggagg gtccacgtgc gtcttccctg acaagaagtc tgagggaagt  12360
aaaatggccc ggtggcccaa agaacagcct tccacctggt atagtcagta caagcggggt  12420
tccctgctct cctatgtgga tgctgaaggc aaccccgtgg gcgtggtaca aatgaccttc  12480
ctgcggctgc tgagcgcctc tgcccaccag aacgtcacct acaactgcta ccagtccgtg  12540
gcctggcagg atgccgccac aggcagctat gataaggcta tccgcttctt gggctccaac  12600
```

```
gatgaggaaa tgtcttatga taacaacccc tacatccgtg ccctggtgga tggctgtgct  12660
accaagaaag gctaccagaa gacggtgctg gagatcgaca cgcccaaagt agagcaagtc  12720
cccattgtgg acatcatgtt caacgacttt ggcgaagcct cacagaaatt tggatttgaa  12780
gtggggccag cttgcttcct aggctagcgg ccgcgactct agatcataat cagccatacc  12840
acatttgtag aggttttact tgctttaaaa aacctcccac acctccccct gaacctgaaa  12900
cataaaatga atgcaattgt tgttgttaac ttgtttattg cagcttataa tggttacaaa  12960
taaagcaata gcatcacaaa tttcacaaat aaagcatttt tttcactgca ttctagttgt  13020
ggtttgtcca aactcatcaa tgtatcttaa ggcgtaaatt gtaagcgtta atattttgtt  13080
aaaattcgcg ttaaattttt gttaaatcag ctcatttttt aaccaatagg ccgaaatcgg  13140
caaaatccct tataaatcaa aagaatagac cgagataggg ttgagtgttg ttccagtttg  13200
gaacaagagt ccactattaa agaacgtgga ctccaacgtc aaagggcgaa aaaccgtcta  13260
tcagggcgat ggcccactac gtgaaccatc accctaatca agttttttgg ggtcgaggtg  13320
ccgtaaagca ctaaatcgga accctaaagg gagcccccga tttagagctt gacggggaaa  13380
gccggcgaac gtggcgagaa aggaagggaa gaaagcgaaa ggagcgggcg ctagggcgct  13440
ggcaagtgta gcggtcacgc tgcgcgtaac caccacaccc gccgcgctta atgcgccgct  13500
acagggcgcg tcaggtggca cttttcgggg aaatgtgcgc ggaaccccta tttgtttatt  13560
tttctaaata cattcaaata tgtatccgct catgagacaa taaccctgat aaatgcttca  13620
ataatattga aaaaggaaga gtcctgaggc ggaaagaacc agctgtggaa tgtgtgtcag  13680
ttagggtgtg gaaagtcccc aggctcccca gcaggcagaa gtatgcaaag catgcatctc  13740
aattagtcag caaccaggtg tggaaagtcc ccaggctccc cagcaggcag aagtatgcaa  13800
agcatgcatc tcaattagtc agcaaccata gtcccgcccc taactccgcc catcccgccc  13860
ctaactccgc ccagttccgc ccattctccg ccccatggct gactaatttt ttttatttat  13920
gcagaggccg aggccgcctc ggcctctgag ctattccaga agtagtgagg aggctttttt  13980
ggaggcctag gcttttgcaa agatcgatca agagacagga tgaggatcgt ttcgcatgat  14040
tgaacaagat ggattgcacg caggttctcc ggccgcttgg gtggagaggc tattcggcta  14100
tgactgggca caacagacaa tcggctgctc tgatgccgcc gtgttccggc tgtcagcgca  14160
ggggcgcccg gttctttttg tcaagaccga cctgtccggt gccctgaatg aactgcaaga  14220
cgaggcagcg cggctatcgt ggctggccac gacgggcgtt ccttgcgcag ctgtgctcga  14280
cgttgtcact gaagcgggaa gggactggct gctattgggc gaagtgccgg ggcaggatct  14340
cctgtcatct caccttgctc ctgccgagaa agtatccatc atggctgatg caatgcggcg  14400
gctgcatacg cttgatccgg ctacctgccc attcgaccac caagcgaaac atcgcatcga  14460
gcgagcacgt actcggatgg aagccggtct tgtcgatcag gatgatctgg acgaagagca  14520
tcaggggctc gcgccagccg aactgttcgc caggctcaag gcgagcatgc ccgacggcga  14580
ggatctcgtc gtgacccatg gcgatgcctg cttgccgaat atcatggtgg aaaatggccg  14640
cttttctgga ttcatcgact gtggccggct gggtgtggcg gaccgctatc aggacatagc  14700
gttggctacc cgtgatattg ctgaagagct tggcggcgaa tgggctgacc gcttcctcgt  14760
gctttacggt atcgccgctc ccgattcgca gcgcatcgcc ttctatcgcc ttcttgacga  14820
gttcttctga gcgggactct ggggttcgaa atgaccgacc aagcgacgcc caacctgcca  14880
tcacgagatt tcgattccac cgccgccttc tatgaaaggt tgggcttcgg aatcgttttc  14940
```

```
cgggacgccg gctggatgat cctccagcgc ggggatctca tgctggagtt cttcgcccac  15000
cctaggggga ggctaactga aacacggaag gagacaatac cggaaggaac ccgcgctatg  15060
acggcaataa aaagacagaa taaaacgcac ggtgttgggt cgtttgttca taaacgcggg  15120
gttcggtccc agggctggca ctctgtcgat accccaccga gaccccattg gggccaatac  15180
gcccgcgttt cttccttttc cccaccccac cccccaagtt cgggtgaagg cccagggctc  15240
gcagccaacg tcggggcggc aggccctgcc atagcctcag gttactcata tatactttag  15300
attgatttaa aacttcattt ttaatttaaa aggatctagg tgaagatcct ttttgataat  15360
ctcatgacca aaatccctta acgtgagttt tcgttccact gagcgtcaga ccccgtagaa  15420
aagatcaaag gatcttcttg agatcctttt tttctgcgcg taatctgctg cttgcaaaca  15480
aaaaaaccac cgctaccagc ggtggtttgt ttgccggatc aagagctacc aactcttttt  15540
ccgaaggtaa ctggcttcag cagagcgcag ataccaaata ctgtccttct agtgtagccg  15600
tagttaggcc accacttcaa gaactctgta gcaccgccta catacctcgc tctgctaatc  15660
ctgttaccag tggctgctgc cagtggcgat aagtcgtgtc ttaccgggtt ggactcaaga  15720
cgatagttac cggataaggc gcagcggtcg ggctgaacgg ggggttcgtg cacacagccc  15780
agcttggagc gaacgaccta caccgaactg agatacctac agcgtgagct atgagaaagc  15840
gccacgcttc ccgaagggag aaaggcggac aggtatccgg taagcggcag ggtcggaaca  15900
ggagagcgca cgagggagct tccaggggga aacgcctggt atctttatag tcctgtcggg  15960
tttcgccacc tctgacttga gcgtcgattt ttgtgatgct cgtcaggggg gcggagccta  16020
tggaaaaacg ccagcaacgc ggccttttta cggttcctgg ccttttgctg gccttttgct  16080
cacatgttct ttcctgcgtt atcccctgat tctgtggata accgtattac cgccatgcat  16140
```

<210> SEQ ID NO 6
<211> LENGTH: 16314
<212> TYPE: DNA
<213> ORGANISM: Artificial Sequence
<220> FEATURE:
<223> OTHER INFORMATION: synthetic polynucleotide

<400> SEQUENCE: 6

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcctgg    600
cttgaggctc aggacgcaaa tcttgaggat gttcagcggg agttttccgg gctgcgagta    660
attggtgatg aggacgagga tggttcggag gatggggaat tttcagacct ggatctgtct    720
gacagcgacc atgaagggga tgagggtggg gggctgttgg gagggggcag gagtctgcac    780
tccctgtatt cactgagcgt cgtctaataa agatgtctat tgatctcttt tagtgtgaat    840
catgtctgac gaggggccag gtacaggacc tggaaatggc ctaggagaga agggagacac    900
```

```
atctggacca gaaggctccg gcggcagtgg acctcaaaga agagggggtg ataaccatgg    960
acgaggacgg ggaagaggac gaggacgagg aggcggaaga ccaggagccc cgggcggctc   1020
aggatcaggg ccaagacata gagatggtgt ccggagaccc caaaaacgtc caagttgcat   1080
tggctgcaaa gggacccacg gtggaacagg agcaggagca ggagcgggag gggcaggagc   1140
aggaggggca ggagcaggag gaggggcagg agcaggagga ggggcaggag gggcaggagg   1200
ggcaggaggg gcaggagcag gaggaggggc aggagcagga ggaggggcag gaggggcagg   1260
aggggcagga gcaggaggag gggcaggagc aggaggaggg gcaggagggg caggagcagg   1320
aggaggggca ggaggggcag gaggggcagg agcaggagga ggggcaggag caggaggagg   1380
ggcaggaggg gcaggagcag gaggaggggc aggaggggca ggaggggcag gagcaggagg   1440
aggggcagga gcaggagggg caggaggggc aggaggggca ggagcaggag gggcaggagc   1500
aggaggaggg gcaggagggg caggaggggc aggagcagga ggggcaggag caggaggggc   1560
aggagcagga ggggcaggag caggaggggc aggaggggca ggagcaggag gggcaggagg   1620
ggcaggagca ggaggggcag gaggggcagg agcaggagga ggggcaggag gggcaggagc   1680
aggaggaggg gcaggagggg caggagcagg aggggcagga ggggcaggag caggaggggc   1740
aggaggggca ggagcaggag gggcaggagg ggcaggagca ggaggagggg caggagcagg   1800
aggggcagga gcaggaggtg gaggccgggg tcgaggaggc agtggaggcc ggggtcgagg   1860
aggtagtgga ggccggggtc gaggaggtag tggaggccgc cggggtagag gacgtgaaag   1920
agccaggggg ggaagtcgtg aaagagccag gggagaggt cgtggacgtg gagaaaagag   1980
gcccaggagt cccagtagtc agtcatcatc atccgggtct ccaccgcgca ggccccctcc   2040
aggtagaagg ccatttttcc accctgtagg ggaagccgat tattttgaat accaccaaga   2100
aggtggccca gatggtgagc ctgacgtgcc cccgggagcg atagagcagg gccccgcaga   2160
tgacccagga gaaggcccaa gcactggacc ccggggtcag ggtgatggag gcaggcgcaa   2220
aaaaggaggg tggtttggaa agcatcgtgg tcaaggaggt tccaacccga aatttgagaa   2280
cattgcagaa ggtttaagag ctctcctggc taggagtcac gtagaaagga ctaccgacga   2340
aggaacttgg gtcgccggtg tgttcgtata tggaggtagt aagacctccc tttacaacct   2400
aaggcgagga actgcccttg ctattccaca atgtcgtctt acaccattga gtcgtctccc   2460
ctttggaatg gcccctggac ccggcccaca acctggcccg ctaagggagt ccattgtctg   2520
ttatttcatg gtctttttac aaactcatat atttgctgag gttttgaagg atgcgattaa   2580
ggaccttgtt atgacaaagc ccgctcctac ctgcaatatc agggtgactg tgtgcagctt   2640
tgacgatgga gtagatttgc ctccctggtt tccacctatg gtggaagggg ctgccgcgga   2700
gggtgatgac ggagatgacg gagatgaagg aggtgatgga gatgagggtg aggaagggca   2760
ggagtgatgt aacttgttag gagacgccct caatcgtatt aaaagccgtg tattcccccg   2820
cactaaagaa taaatcccca gtagacatca tgcgtgctgt tggtgtattt ctggccatct   2880
gtcttgtcac cattttcgtc ctcccaacat ggggcaattg ggcataccca tgttgtcacg   2940
tcactcagct ccgcgctcaa caccttctcg cgttggaaaa cattagcgac atttacctgg   3000
tgagcaatca gacatgcgac ggctttagcc tggcctcctt aaattcacct aagaatggga   3060
gcaaccagca ggaaaaggac aagcagcgaa aattcacgcc cccttgggag gtggcggcat   3120
atgcaaagga tagcactccc actctactac tgggtatcat atgctgactg tatatgcatg   3180
aggatagcat atgctacccg gatacagatt aggatagcat atactaccca gatatagatt   3240
```

```
aggatagcat atgctaccca gatatagatt aggatagcct atgctaccca gatataaatt   3300
aggatagcat atactaccca gatatagatt aggatagcat atgctaccca gatatagatt   3360
aggatagcct atgctaccca gatatagatt aggatagcat atgctaccca gatatagatt   3420
aggatagcat atgctatcca gatatttggg tagtatatgc tacccagata taaattagga   3480
tagcatatac taccctaatc tctattagga tagcatatgc tacccggata cagattagga   3540
tagcatatac tacccagata tagattagga tagcatatgc tacccagata tagattagga   3600
tagcctatgc tacccagata taaattagga tagcatatac tacccagata tagattagga   3660
tagcatatgc tacccagata tagattagga tagcctatgc tacccagata tagattagga   3720
tagcatatgc tatccagata tttgggtagt atatgctacc catggcaaca ttagcccacc   3780
gtgctctcag cgacctcgtg aatatgagga ccaacaaccc tgtgcttggc gctcaggcgc   3840
aagtgtgtgt aatttgtcct ccagatcgca gcaatcgcgc ccctatcttg gcccgcccac   3900
ctacttatgc aggtattccc cggggtgcca ttagtggttt tgtgggcaag tggtttgacc   3960
gcagtggtta gcggggttac aatcagccaa gttattacac ccttatttta cagtccaaaa   4020
ccgcagggcg gcgtgtgggg gctgacgcga tcgctgttcc ttaggaccct tttactaacc   4080
ctaattcgat agcatatgct tcccgttggg taacatatgc tattgaatta gggttagtct   4140
ggatagtata tactactacc cgggaagcat atgctacccg tttagggtta acaagggggc   4200
cttataaaca ctattgctaa tgccctcttg agggtccgct tatcggtagc tacacaggcc   4260
cctctgattg acgttggtgt agcctcccgt agtcttcctg ggcccctggg aggtacatgt   4320
cccccagcat tggtgtaaga gcttcagcca agagttacac ataaaggcaa tgttgtgttg   4380
cagtccacag actgcaaagt ctgctccagg atgaaagcca ctcagtgttg gcaaatgtgc   4440
acatccattt ataaggatgt caactacagt cagagaaccc ctttgtgttt ggtccccccc   4500
cgtgtcacat gtggaacagg gcccagttgg caagttgtac caaccaactg aagggattac   4560
atgcactgcc ccgtgaccaa tacaaaacaa aagcgctcct cgtaccagcg aagaaggggc   4620
agagatgccg tagtcaggtt tagttcgtcc ggcggcggga tctcgacatt gattattgac   4680
tagttattaa tartaatcaa ttacggggtc attagttcat agcccatata tggagttccg   4740
cgttacataa cttacggtaa atggcccgcc tggctgaccg cccaacgacc cccgcccatt   4800
gacgtcaata atgacgtatg ttcccatagt aacgccaata gggactttcc attgacgtca   4860
atgggtggac tatttacggt aaactgccca cttggcagta catcaagtgt atcatatgcc   4920
aagtacgccc cctattgacg tcaatgacgg taaatggccc gcctggcatt atgcccagta   4980
catgacctta tgggactttc ctacttggca gtacatctac gtattagtca tcgctattac   5040
catgggtcga ggtgagcccc acgttctgct tcactctccc catctccccc ccctccccac   5100
ccccaatttt gtatttattt atttttttaat tattttgtgc agcgatgggg gcgggggggg   5160
ggggggcgcg cgccaggcgg ggcggggcgg ggcgaggggc ggggcggggc gaggcggaga   5220
ggtgcggcgg cagccaatca gagcggcgcg ctccgaaagt ttccttttat ggcgaggcgg   5280
cggcggcggc ggccctataa aaagcgaagc gcgcggcggg cgggagtcgc tgcgttgcct   5340
tcgccccgtg ccccgctccg cgccgcctcg cgccgcccgc cccggctctg actgaccgcg   5400
ttactcccac aggtgagcgg gcgggacggc ccttctcctc cgggctgtaa ttagcgcttg   5460
gtttaatgac ggctcgtttc ttttctgtgg ctgcgtgaaa gccttaaagg gctccgggag   5520
ggccctttgt gcggggggga gcggctcggg gggtgcgtgc gtgtgtgtgt gcgtggggag   5580
cgccgcgtgc ggcccgcgct gcccggcggc tgtgagcgct gcgggcgcgg cgcggggctt   5640
```

```
tgtgcgctcc gcgtgtgcgc gaggggagcg cggccggggg cggtgccccg cggtgcgggg   5700
gggctgcgag gggaacaaag gctgcgtgcg ggtgtgtgc gtgggggggt gagcaggggg   5760
tgtgggcgcg gcggtcgggc tgtaaccccc ccctgcaccc ccctccccga gttgctgagc   5820
acggcccggc ttcgggtgcg gggctccgtg cggggcgtgg cgcggggctc gccgtgccgg   5880
gcgggggggtg gcggcaggtg gggtgccgg gcggggcggg gccgcctcgg gccggggagg   5940
gctcggggga ggggcgcggc ggccccggag cgccggcggc tgtcgaggcg cggcgagccg   6000
cagccattgc cttttatggt aatcgtgcga gagggcgcag ggacttcctt tgtcccaaat   6060
ctggcggagc cgaaatctgg gaggcgccgc cgcacccccct ctagcgggcg cgggcgaagc   6120
ggtgcggcgc cggcaggaag gaaatgggcg gggagggcct tcgtgcgtcg ccgcgccgcc   6180
gtccccttct ccatctccag cctcggggct gccgcagggg gacggctgcc ttcggggggg   6240
acggggcagg gcggggttcg gcttctggcg tgtgaccggc ggctctagag cctctgctaa   6300
ccatgttcat gccttcttct ttttcctaca gctcctgggc aacgtgctgg ttgttgtgct   6360
gtctcatcat tttggcaaag aattaaccct cactaaaggg taccgggccc cccctcgagg   6420
tcgaccgccg gcatggacgt acacacccgc tggaaagctg cgcgcccagg cgccctgctg   6480
ctgtcttcgc cgctactcct gttcctgctg ctgctgtggg cgccgccttc gagccgcgca   6540
gctcagccag cagatcttct ggagatgcta gattttcaca atttgccctc aggggtaacg   6600
aaaaccacag gtttctgtgc tactcgaaga tcttccagcg agccggatgt tgcctaccga   6660
gtctctaaag atgcacagct cagcatgccc accaagcagc tgtaccctga gtctggtttt   6720
cccgaggact tctccatcct gacaaccgtg aaagccaaga aaggcagcca ggccttccta   6780
gtctccattt acaatgagca gggcatccag cagttggggc tggagctggg ccgctcccct   6840
gtcttcctct atgaggacca cacagggaag cccgggcctg aagagtatcc gcttttccct   6900
ggcatcaact tgtccgatgg caagtggcac cgaattgctc tcagtgtcta caagaaaaat   6960
gtcaccttga tcctcgactg taagaagaag attacgaagt tcctcagccg cagtgaccac   7020
cccataatag acaccaatgg gattgtcatg tttggctccc ggattctgga tgatgaaata   7080
tttgagggtg acatccaaca gttgcttttc gtctctgaca accgagctgc ctatgactac   7140
tgtgagcact acagccccga ctgtgacact gcggtccctg acacacctca gtcacaggac   7200
cctaacccgg atgaatatta cccagaagga gagggtgaga cctattacta tgagtatcca   7260
tattatgaag accctgaaga cccgggaaag gagcctgccc ctactcagaa gccagtggaa   7320
gctgccagag aaaccacaga ggttcctgag gagcagaccc agcccctacc cgaagcccct   7380
acagtgcctg agaccagtga cacggctgac aaggaggaca gtctagggat cggggactat   7440
gactacgtgc ccccagatga ctattacact ccaccccat atgaagactt tggatatggc   7500
gagggtgtgg agaaccctga ccagcccacc aaccccgact caggggctga ggtccccacc   7560
agcaccactg ttacctccaa cacctccaat ccagctccag gagaagggaa ggatgacctg   7620
ggcggcgaat tcaccgagga aaccatcaag aatctagagg aaaactacta tgacccgtac   7680
tttgaccccg actccgactc cagtgtctct ccatcagaga tagggccagg catgcccgct   7740
aaccaggaca ccatctttga ggcgatcgct ggctccacct ccggctccgg caagcccggc   7800
tccggcgagg gctccaccaa gcccggcgct agtatggcag aaatcggtac tggctttcca   7860
ttcgaccccc attatgtgga agtcctgggc gagcgcatgc actacgtcga tgttggtccg   7920
cgcgatggca cccctgtgct gttcctgcac ggtaacccga cctcctccta cgtgtggcgc   7980
```

```
aacatcatcc cgcatgttgc accgacccat cgctgcattg ctccagacct gatcggtatg   8040

ggcaaatccg acaaaccaga cctgggttat ttcttcgacg accacgtccg cttcatggat   8100

gccttcatcg aagccctggg tctggaagag gtcgtcctgg tcattcacga ctggggctcc   8160

gctctgggtt tccactgggc caagcgcaat ccagagcgcg tcaaaggtat tgcatttatg   8220

gagttcatcc gccctatccc gacctgggac gaatggccag aatttgcccg cgagaccttc   8280

caggccttcc gcaccaccga cgtcggccgc aagctgatca tcgatcagaa cgtttttatc   8340

gagggtacgc tgccgatggg tgtcgtccgc ccgctgactg aagtcgagat ggaccattac   8400

cgcgagccgt tcctgaatcc tgttgaccgc gagccactgt ggcgcttccc aaacgagctg   8460

ccaatcgccg gtgagccagc gaacatcgtc gcgctggtcg aagaatacat ggactggctg   8520

caccagtccc ctgtcccgaa gctgctgttc tggggcaccc caggcgttct gatcccaccg   8580

gccgaagccg ctcgcctggc caaaagcctg cctaactgca aggctgtgga catcggcccg   8640

ggtctgaatc tgctgcaaga agacaacccg gacctgatcg gcagcgagat cgcgcgctgg   8700

ctgtctactc tggagatttc cggtctcgac ggctccacct ccggctccgg caagcccggc   8760

tccggcgagg gctccaccaa gcccggcact agcgggattg gaggaccccg aggtgagaaa   8820

gggcaaaagg gagaaccagc catcattgag ccggggatgc tgatcgaggg gccccctggc   8880

cctgaaggcc ctgctggtct tccaggacct ccaggaacta caggtcctac tggccaaatg   8940

ggtgaccctg gagaaagggg tcccccctggg cgcccaggtc ttcctggagc tgatggcttg   9000

cctggccccc caggtaccat gctcatgctg ccgttccggt ttggaggcgg tggcgatgcc   9060

ggttctaagg gccccatggt ctctgcgcag gagtcccagg cccaggctat cctccagcaa   9120

gccaggttgg cactgagggg accagctggc ccaatgggtc tcaccgggag acctggcccc   9180

atgggtcctc ctgggagtgg cggtttgaaa ggtgagccag gagacatggg acctcagggt   9240

cctcgaggtg tgcaaggccc acctggccca acagggaagc ctggaagacg ggggccgtgct   9300

ggaagtgatg gagccagagg catgcctgga caaacaggcc ccaagggtga ccgtggcttt   9360

gatggtctgg ctgggttgcc gggagagaaa ggccatagag gtgaccctgg tccttctggc   9420

ccgcccggaa tcccaggaga tgatggagaa aggggtgacg atggagaagt tgggcccagg   9480

ggactgcccg gggagcctgg accacgtggt ctgcttgggc caaaaggccc cccagggcct   9540

cctggacctc ctggtgtaac gggtatggat ggccagcctg gcccaaaagg aaatgtgggt   9600

ccccagggag agcctgggcc gccaggacag cagggtaatc ctggtgccca gggtcttcca   9660

ggtccccagg gtgccattgg tcctccagga gaaaagggtc ctttggggaa accaggtctc   9720

ccaggaatgc caggcgctga tggacccccg gggcaccctg gaaaagaagg tcctccagga   9780

gagaaaggag gccagggtcc tcctggcccc cagggtccca ttggctaccc cggtccacga   9840

ggagtcaagg gggcagatgg catccgaggt ctgaagggca ccaaggggga gaagggtgaa   9900

gacggcttcc ctgggtttaa aggcgacatg ggaataaagg gtgaccgggg ggaaatcggc   9960

ccacctggtc cccgaggaga agatggtcct gaaggtccaa agggtcgagg tggtcccaat  10020

ggtgatcctg gtcccctggg gcccactggg gaaaagggaa agcttggcgt gcccggatta  10080

ccggggtacc caggaagaca agggccaaag ggttccattg gattccctgg cttcccgggc  10140

gccaacggag agaagggtgg caggggggaca cctggaaagc caggaccacg gggacagaga  10200

ggcccaacgg gcccgcgggg tgaacgaggc ccacgaggca tcacggggaa gcctggccct  10260

aagggcaact ccggaggtga tggcccagct ggccctcctg gtgaacgggg acccaacgga  10320

ccccaaggtc ccaccggctt tcctggaccc aagggtcccc cgggcccacc aggcaaggac  10380
```

```
ggactccctg gacaccctgg gcagagaggg gagaccggtt tccaaggcaa gactggccct  10440
ccagggcccc caggagtggt tggccctcag ggtcccacag gagagacggg ccccatgggt  10500
gagcgtggcc atcctggtcc tccaggccct cctggtgaac agggcctccc aggtgctgct  10560
gggaaagaag gaacgaaggg tgacccaggt cctgctggcc tccctgggaa ggatggccct  10620
ccaggattgc gtggattccc tggggaccga gggctacctg gccccgtggg agcccttgga  10680
ctcaaaggca gtgaaggccc ccctggccca ccaggtcctg cgggttctcc aggggagaga  10740
ggaccagctg gtgccgctgg gcccatcgga attccaggga gacctgggcc tcagggacct  10800
ccggggcctg ctggagagaa aggacttcct ggcgagaaag gtccacaagg cccagctggc  10860
cgagatggcc tccaaggtcc cgtggggctc cctggaccag ccggcccagt gggtcctcct  10920
ggagaagatg gagataaggg agagatcgga gagccagggc agaagggaag caagggcgac  10980
aaaggcgagc agggtcctcc tgggcctacc ggtcctcaag gcccgattgg acagccaggc  11040
ccttcgggag cagatggtga acctggccct cgtggacagc agggcctgtt tgggcagaaa  11100
ggagatgaag gttcaagagg tttcccagga ccccccgggc cagtgggatt gcagggtttg  11160
ccaggacctc caggagaaaa gggcgagaca ggagacgtgg gccagatggg ccctcctggt  11220
ccaccaggcc cccgaggacc ctctggagct ccaggtgccg atggaccaca gggtcctccc  11280
ggagggattg gcaaccctgg tgcagtcgga gaaaagggag aacctggtga agctggagat  11340
cctggccttc caggagaagg aggtcccctg ggacctaaag gagaaagagg ggagaaggga  11400
gaggctggcc cctctggtgc tgctggaccc cctggaccca aaggccctcc tggagatgat  11460
ggccccaaag gcagccctgg ccctgtgggc tttcctggag atcctggtcc ccctggagag  11520
ccaggccccg caggtcaaga cggcccacct ggtgacaaag gggacgatgg tgaacctggg  11580
cagacggggt ccccgggccc tactggtgaa cctggtccat ctgggcctcc aggaaagagg  11640
ggtcccccag gccctgcagg ccctgaaggc aggcaggggg agaaaggagc caagggagaa  11700
gctggcttag aaggccctcc tgggaagact ggccccattg gcccccaagg ggcccctggg  11760
aagcctggcc ccgatggtct ccgtggaatc cctggtcctg tgggtgagca aggcctccca  11820
ggatccccag gccccgatgg tccacccggc cccatgggtc ctccaggact ccctggcctc  11880
aaaggagact ccggtcccaa aggtgaaaag ggccatccag gcctgattgg actcatcggc  11940
cctccgggag agcaaggtga aaagggtgac cgtggactcc caggccccca gggttcatct  12000
ggtcctaaag gagatcaggg catcacaggt ccttctggcc cacttgggcc tcctggtcct  12060
cctggcttgc cgggccctcc aggtcccaaa ggtgctaagg gctcttcggg tcccaccggc  12120
ccgaagggtg aggcaggcca cccaggactc cccggcccac ctggccctcc gggtgaggtc  12180
atccagcccc tgccaatcca ggcctccagg actcggcgga acattgatgc cagccagctc  12240
ctggacgatg ggggctgggga gagctacgtg gattatgcag atggcatgga agagatcttt  12300
ggttccctca actccctgaa gctggagatt gaacagatga agcgaccact gggcacccag  12360
cagaacccag cccgtacctg caaggatcta cagctctgtc atcctgactt cccagatggc  12420
gaatactggg tcgatcccaa ccaagggtgc tccagggact ccttcaaagt ctactgcaat  12480
ttcacagctg gagggtccac gtgcgtcttc cctgacaaga agtctgaggg aagtaaaatg  12540
gcccggtggc ccaaagaaca gccttccacc tggtatagtc agtacaagcg gggttccctg  12600
ctctcctatg tggatgctga aggcaacccc gtgggcgtgg tacaaatgac cttcctgcgg  12660
ctgctgagcg cctctgccca ccagaacgtc acctacaact gctaccagtc cgtggcctgg  12720
```

```
caggatgccg ccacaggcag ctatgataag gctatccgct tcttgggctc caacgatgag  12780
gaaatgtctt atgataacaa cccctacatc cgtgccctgg tggatggctg tgctaccaag  12840
aaaggctacc agaagacggt gctggagatc gacacgccca aagtagagca agtccccatt  12900
gtggacatca tgttcaacga ctttggcgaa gcctcacaga aatttggatt tgaagtgggg  12960
ccagcttgct tcctaggcta gcggccgcga ctctagatca taatcagcca taccacattt  13020
gtagaggttt tacttgcttt aaaaaacctc ccacacctcc ccctgaacct gaaacataaa  13080
atgaatgcaa ttgttgttgt taacttgttt attgcagctt ataatggtta caaataaagc  13140
aatagcatca caaatttcac aaataaagca tttttttcac tgcattctag ttgtggtttg  13200
tccaaactca tcaatgtatc ttaaggcgta aattgtaagc gttaatattt tgttaaaatt  13260
cgcgttaaat ttttgttaaa tcagctcatt ttttaaccaa taggccgaaa tcggcaaaat  13320
cccttataaa tcaaaagaat agaccgagat agggttgagt gttgttccag tttggaacaa  13380
gagtccacta ttaaagaacg tggactccaa cgtcaaaggg cgaaaaaccg tctatcaggg  13440
cgatggccca ctacgtgaac catcacccta atcaagtttt ttggggtcga ggtgccgtaa  13500
agcactaaat cggaacccta aagggagccc ccgatttaga gcttgacggg gaaagccggc  13560
gaacgtggcg agaaaggaag ggaagaaagc gaaaggagcg ggcgctaggg cgctggcaag  13620
tgtagcggtc acgctgcgcg taaccaccac acccgccgcg cttaatgcgc cgctacaggg  13680
cgcgtcaggt ggcacttttc ggggaaatgt gcgcggaacc cctatttgtt tatttttcta  13740
aatacattca aatatgtatc cgctcatgag acaataaccc tgataaatgc ttcaataata  13800
ttgaaaaagg aagagtcctg aggcggaaag aaccagctgt ggaatgtgtg tcagttaggg  13860
tgtggaaagt ccccaggctc cccagcaggc agaagtatgc aaagcatgca tctcaattag  13920
tcagcaacca ggtgtggaaa gtccccaggc tccccagcag gcagaagtat gcaaagcatg  13980
catctcaatt agtcagcaac catagtcccg cccctaactc cgcccatccc gcccctaact  14040
ccgcccagtt ccgcccattc tccgccccat ggctgactaa ttttttttat ttatgcagag  14100
gccgaggccg cctcggcctc tgagctattc cagaagtagt gaggaggctt ttttggaggc  14160
ctaggctttt gcaaagatcg atcaagagac aggatgagga tcgtttcgca tgattgaaca  14220
agatggattg cacgcaggtt ctccggccgc ttgggtggag aggctattcg gctatgactg  14280
ggcacaacag acaatcggct gctctgatgc cgccgtgttc cggctgtcag cgcaggggcg  14340
cccggttctt tttgtcaaga ccgacctgtc cggtgccctg aatgaactgc aagacgaggc  14400
agcgcggcta tcgtggctgg ccacgacggg cgttccttgc gcagctgtgc tcgacgttgt  14460
cactgaagcg ggaagggact ggctgctatt gggcgaagtg ccggggcagg atctcctgtc  14520
atctcacctt gctcctgccg agaaagtatc catcatggct gatgcaatgc ggcggctgca  14580
tacgcttgat ccggctacct gcccattcga ccaccaagcg aaacatcgca tcgagcgagc  14640
acgtactcgg atggaagccg gtcttgtcga tcaggatgat ctggacgaag agcatcaggg  14700
gctcgcgcca gccgaactgt tcgccaggct caaggcgagc atgcccgacg gcgaggatct  14760
cgtcgtgacc catggcgatg cctgcttgcc gaatatcatg gtggaaaatg gccgcttttc  14820
tggattcatc gactgtggcc ggctgggtgt ggcggaccgc tatcaggaca tagcgttggc  14880
tacccgtgat attgctgaag agcttggcgg cgaatgggct gaccgcttcc tcgtgcttta  14940
cggtatcgcc gctcccgatt cgcagcgcat cgccttctat cgccttcttg acgagttctt  15000
ctgagcggga ctctggggtt cgaaatgacc gaccaagcga cgcccaacct gccatcacga  15060
gatttcgatt ccaccgccgc cttctatgaa aggttgggct tcggaatcgt tttccgggac  15120
```

gccggctgga tgatcctcca gcgcggggat ctcatgctgg agttcttcgc ccaccctagg 15180
gggaggctaa ctgaaacacg gaaggagaca ataccggaag gaacccgcgc tatgacggca 15240
ataaaaagac agaataaaac gcacggtgtt gggtcgtttg ttcataaacg cggggttcgg 15300
tcccagggct ggcactctgt cgataccca ccgagacccc attggggcca atacgcccgc 15360
gtttcttcct tttccccacc ccacccccca agttcgggtg aaggcccagg gctcgcagcc 15420
aacgtcgggg cggcaggccc tgccatagcc tcaggttact catatatact ttagattgat 15480
ttaaaacttc atttttaatt taaaaggatc taggtgaaga tcctttttga taatctcatg 15540
accaaaatcc cttaacgtga gttttcgttc cactgagcgt cagaccccgt agaaaagatc 15600
aaaggatctt cttgagatcc tttttttctg cgcgtaatct gctgcttgca aacaaaaaaa 15660
ccaccgctac cagcggtggt ttgtttgccg gatcaagagc taccaactct ttttccgaag 15720
gtaactggct tcagcagagc gcagatacca aatactgtcc ttctagtgta gccgtagtta 15780
ggccaccact tcaagaactc tgtagcaccg cctacatacc tcgctctgct aatcctgtta 15840
ccagtggctg ctgccagtgg cgataagtcg tgtcttaccg ggttggactc aagacgatag 15900
ttaccggata aggcgcagcg gtcgggctga acggggggtt cgtgcacaca gcccagcttg 15960
gagcgaacga cctacaccga actgagatac ctacagcgtg agctatgaga aagcgccacg 16020
cttcccgaag ggagaaaggc ggacaggtat ccggtaagcg gcagggtcgg aacaggagag 16080
cgcacgaggg agcttccagg gggaaacgcc tggtatcttt atagtcctgt cgggtttcgc 16140
cacctctgac ttgagcgtcg atttttgtga tgctcgtcag gggggcggag cctatggaaa 16200
aacgccagca acgcggcctt tttacggttc ctggcctttt gctggccttt tgctcacatg 16260
ttctttcctg cgttatcccc tgattctgtg gataaccgta ttaccgccat gcat 16314

<210> SEQ ID NO 7
<211> LENGTH: 72
<212> TYPE: DNA
<213> ORGANISM: Artificial Sequence
<220> FEATURE:
<223> OTHER INFORMATION: synthetic polynucleotide

<400> SEQUENCE: 7
gcgatcgctg gctccacctc cggctccggc aagcccggct ccggcgaggg ctccaccaag 60
cccggcgcta gt 72

<210> SEQ ID NO 8
<211> LENGTH: 24
<212> TYPE: PRT
<213> ORGANISM: Artificial Sequence
<220> FEATURE:
<223> OTHER INFORMATION: synthetic peptide

<400> SEQUENCE: 8

Ala Ile Ala Gly Ser Thr Ser Gly Ser Gly Lys Pro Gly Ser Gly Glu
1 5 10 15

Gly Ser Thr Lys Pro Gly Ala Ser
20

<210> SEQ ID NO 9
<211> LENGTH: 8075
<212> TYPE: DNA
<213> ORGANISM: Mus musculus

<400> SEQUENCE: 9

-continued

```
ccagcagcga gggagggagg gaaagggggg aaaagtgctc agcgccgaag gcgaggtccg     60
cactcctggt ccccgcggct ggcgcaggac ctcactccag cggagcgccc acggggagcg    120
ggtcgcgggg cagcagcggt gaggaggcca cgagactaga aggaggagga cagggagtgc    180
gcgagcagcc agcgaggggg tcccggccgt cccgggccac agtcgatccc tgcgccgtgg    240
gcgagcgcgc ccgctgcctc ttccagaaca gccaccgccg cgggggagat cgggcgggtg    300
ccgagcttcc tatgactccc tgaagttgtc gtgctcccct agcgtccgcc acccgggacg    360
tgtctctggt ccccgtgcat cgtgtgcgtc tcccgctccc cggcccgcgc accccgccgg    420
catggacgta cacacccgct ggaaagctgc gcgcccaggc gccctgctgc tgtcttcgcc    480
gctactcctg ttcctgctgc tgctgtgggc gccgccttcg agccgcgcag ctcagccagc    540
agatcttctg gagatgctag attttcacaa tttgccctca ggggtaacga aaaccacagg    600
tttctgtgct actcgaagat cttccagcga gccggatgtt gcctaccgag tctctaaaga    660
tgcacagctc agcatgccca ccaagcagct gtaccctgag tctggttttc ccgaggactt    720
ctccatcctg acaaccgtga aagccaagaa aggcagccag gccttcctag tctccattta    780
caatgagcag ggcatccagc agttggggct ggagctgggc cgctcccctg tcttcctcta    840
tgaggaccac acagggaagc ccgggcctga agagtatccg cttttccctg gcatcaactt    900
gtccgatggc aagtggcacc gaattgctct cagtgtctac aagaaaaatg tcaccttgat    960
cctcgactgt aagaagaaga ttacgaagtt cctcagccgc agtgaccacc ccataataga   1020
caccaatggg attgtcatgt ttggctcccg gattctggat gatgaaatat ttgagggtga   1080
catccaacag ttgcttttcg tctctgacaa ccgagctgcc tatgactact gtgagcacta   1140
cagccccgac tgtgacactg cggtccctga cacacctcag tcacaggacc ctaacccgga   1200
tgaatattac ccagaaggag agggtgagac ctattactat gagtatccat attatgaaga   1260
ccctgaagac ccgggaaagg agcctgcccc tactcagaag ccagtggaag ctgccagaga   1320
aaccacagag gttcctgagg agcagaccca gcccctaccc gaagccccta cagtgcctga   1380
gaccagtgac acggctgaca aggaggacag tctagggatc ggggactatg actacgtgcc   1440
cccagatgac tattacactc cacccccata tgaagacttt ggatatggcg agggtgtgga   1500
gaaccctgac cagcccacca accccgactc aggggctgag gtccccacca gcaccactgt   1560
tacctccaac acctccaatc cagctccagg agaagggaag gatgacctgg gcggcgaatt   1620
caccgaggaa accatcaaga atctagagga aaactactat gacccgtact ttgaccccga   1680
ctccgactcc agtgtctctc catcagagat agggccaggc atgcccgcta accaggacac   1740
catctttgag ggaattggag gaccccgagg tgagaaaggg caaaagggag aaccagccat   1800
cattgagccg gggatgctga tcgaggggcc ccctggccct gaaggccctg ctggtcttcc   1860
aggacctcca ggaactacag gtcctactgg ccaaatgggt gaccctggag aaaggggtcc   1920
ccctgggcgc ccaggtcttc ctggagctga tggcttgcct ggcccccccag gtaccatgct   1980
catgctgccg ttccggtttg gaggcggtgg cgatgccggt tctaagggcc ccatggtctc   2040
tgcgcaggag tcccaggccc aggctatcct ccagcaagcc aggttggcac tgaggggacc   2100
agctggccca atgggtctca ccgggagacc tggccccatg ggtcctcctg ggagtggcgg   2160
tttgaaaggt gagccaggag acatgggacc tcagggtcct cgaggtgtgc aaggcccacc   2220
tggcccaaca gggaagcctg gaagacgggg ccgtgctgga agtgatggag ccagaggcat   2280
gcctggacaa acaggcccca agggtgaccg tggctttgat ggtctggctg ggttgccggg   2340
agagaaaggc catagaggtg accctggtcc ttctggcccg cccggaatcc caggagatga   2400
```

```
tggagaaagg ggtgacgatg gagaagttgg gcccagggga ctgcccgggg agcctggacc   2460
acgtggtctg cttgggccaa aaggcccccc agggcctcct ggacctcctg gtgtaacggg   2520
tatggatggc cagcctggcc caaaaggaaa tgtgggtccc cagggagagc ctgggccgcc   2580
aggacagcag ggtaatcctg gtgcccaggg tcttccaggt ccccagggtg ccattggtcc   2640
tccaggagaa aagggtcctt tggggaaacc aggtctccca ggaatgccag gcgctgatgg   2700
acccccgggg caccctggaa aagaaggtcc tccaggagag aaaggaggcc agggtcctcc   2760
tggcccccag ggtcccattg gctaccccgg tccacgagga gtcaaggggg cagatggcat   2820
ccgaggtctg aagggcacca agggggagaa gggtgaagac ggcttccctg ggtttaaagg   2880
cgacatggga ataaagggtg accgggggga aatcggccca cctggtcccc gaggagaaga   2940
tggtcctgaa ggtccaaagg gtcgaggtgg tcccaatggt gatcctggtc cctggggcc    3000
cactggggaa aagggaaagc ttggcgtgcc cggattaccg gggtacccag gaagacaagg   3060
gccaaagggt tccattggat tccctggctt cccgggcgcc aacggagaga agggtggcag   3120
ggggacacct ggaaagccag gaccacgggg acagagaggc ccaacgggcc cgcggggtga   3180
acgaggccca cgaggcatca cggggaagcc tggccctaag ggcaactccg gaggtgatgg   3240
cccagctggc cctcctggtg aacggggacc caacggaccc caaggtccca ccggctttcc   3300
tggacccaag ggtcccccgg gcccaccagg caaggacgga ctccctggac accctgggca   3360
gagaggggag accggtttcc aaggcaagac tggccctcca gggcccccag gagtggttgg   3420
ccctcagggt cccacaggag agacgggccc catgggtgag cgtggccatc ctggtcctcc   3480
aggccctcct ggtgaacagg gcctcccagg tgctgctggg aaagaaggaa cgaagggtga   3540
cccaggtcct gctggcctcc ctgggaagga tggccctcca ggattgcgtg gattccctgg   3600
ggaccgaggg ctacctggcc ccgtgggagc ccttggactc aaaggcagtg aaggcccccc   3660
tggcccacca ggtcctgcgg gttctccagg ggagagagga ccagctggtg ccgctgggcc   3720
catcggaatt ccagggagac ctgggcctca gggacctccg gggcctgctg gagagaaagg   3780
acttcctggc gagaaaggtc cacaaggccc agctggccga gatggcctcc aaggtcccgt   3840
ggggctccct ggaccagccg gcccagtggg tcctcctgga gaagatggag ataagggaga   3900
gatcggagag ccagggcaga agggaagcaa gggcgacaaa ggcgagcagg gtcctcctgg   3960
gcctaccggt cctcaaggcc cgattggaca gccaggccct tcgggagcag atggtgaacc   4020
tggccctcgt ggacagcagg gcctgtttgg gcagaaagga gatgaaggtt caagaggttt   4080
cccaggaccc cccgggccag tgggattgca gggtttgcca ggacctccag gagaaaaggg   4140
cgagacagga gacgtgggcc agatgggccc tcctggtcca ccaggccccc gaggaccctc   4200
tggagctcca ggtgccgatg gaccacaggg tcctcctgga gggattggca accctggtgc   4260
agtcggagaa aagggagaac ctggtgaagc tggagatcct ggccttccag gagaaggagg   4320
tcccctggga cctaaaggag aaagagggga gaagggagag gctggcccct ctggtgctgc   4380
tggaccccct ggacccaaag gccctcctgg agatgatggc cccaaaggca gccctggccc   4440
tgtgggcttt cctggagatc ctggtccccc tggagagcca ggccccgcag gtcaagacgg   4500
cccacctggt gacaaagggg acgatggtga acctgggcag acggggtccc cgggccctac   4560
tggtgaacct ggtccatctg ggcctccagg aaagaggggt cccccaggcc ctgcaggccc   4620
tgaaggcagg caggggggaga aaggagccaa gggagaagct ggcttagaag gccctcctgg   4680
gaagactggc cccattggcc cccaaggggc ccctgggaag cctggccccg atggtctccg   4740
```

```
tggaatccct ggtcctgtgg gtgagcaagg cctcccagga tccccaggcc ccgatggtcc   4800
acccggcccc atgggtcctc caggactccc tggcctcaaa ggagactccg gtcccaaagg   4860
tgaaaagggc catccaggcc tgattggact catcggccct ccgggagagc aaggtgaaaa   4920
gggtgaccgt ggactcccag gcccccaggg ttcatctggt cctaaaggag atcagggcat   4980
cacaggtcct tctggcccac ttgggcctcc tggtcctcct ggcttgccgg gccctccagg   5040
tcccaaaggt gctaagggct cttcgggtcc caccggcccg aagggtgagg caggccaccc   5100
aggactcccc ggcccacctg gccctccggg tgaggtcatc cagcccctgc caatccaggc   5160
ctccaggact cggcggaaca ttgatgccag ccagctcctg gacgatgggg ctggggagag   5220
ctacgtggat tatgcagatg gcatggaaga gatctttggt tccctcaact ccctgaagct   5280
ggagattgaa cagatgaagc gaccactggg cacccagcag aacccagccc gtacctgcaa   5340
ggatctacag ctctgtcatc ctgacttccc agatggcgaa tactgggtcg atcccaacca   5400
agggtgctcc agggactcct tcaaagtcta ctgcaatttc acagctggag ggtccacgtg   5460
cgtcttccct gacaagaagt ctgagggaag taaaatggcc cggtggccca aagaacagcc   5520
ttccacctgg tatagtcagt acaagcgggg ttccctgctc tcctatgtgg atgctgaagg   5580
caaccccgtg ggcgtggtac aaatgacctt cctgcggctg ctgagcgcct ctgcccacca   5640
gaacgtcacc tacaactgct accagtccgt ggcctggcag gatgccgcca caggcagcta   5700
tgataaggct atccgcttct tgggctccaa cgatgaggaa atgtcttatg ataacaaccc   5760
ctacatccgt gccctggtgg atggctgtgc taccaagaaa ggctaccaga agacggtgct   5820
ggagatcgac acgcccaaag tagagcaagt ccccattgtg gacatcatgt tcaacgactt   5880
tggcgaagcc tcacagaaat ttggatttga agtggggcca gcttgcttcc taggctagga   5940
gctgctgagc ccaccggtct ccagagcaac ctcgtgacct cagcacccca cctgtgggcg   6000
tcctgtgcac ggcccatccc ggacagtgaa catttctcac ccctgcctgc ctgactcatc   6060
tgtgcctcgg accctccgtg gcattggacc ccatgcccag agagaacaaa gggaaagagc   6120
cgtgtcccca cggagccgaa tcacatgacc tagccacacc acagcctctt gccacccttc   6180
agctctcagg ataggttcat taaaggtgtt aatggaccgt tggccgggag tgggggcggg   6240
acagtatttg aagatcactt taaaaaaaat tcaacttgaa gatatgtatt ccccctgacc   6300
ttcaaaagat gttctgaggt ggtcttgtaa aggtcgccaa agcctccatt ttttttaaa   6360
acaaccctca acacatccac tcagaggcca aatgtcattc cacacgtgcc tttccgatgg   6420
attaaaggtg cttatgtttt tgtgagaatt ttaagtaaat atttgtattg tattgttata   6480
aatgttaagt gtgcctggct ttcagtcttg catggaaacc cagccttagg cccatggggg   6540
cagcgggcag ctgggacaag tcacccgctc gggctcgaaa tccggctctc ggtagagggc   6600
atcgccttac ccccaccccc acaagaatgt gcaataattt ggaaatttgc ccagtcagca   6660
agaagcggca ttgccactgc aggtgcctgg gcccctttcc agactcttta tttttttctt   6720
tttgattagc tctggataat tttttatggg gaggggaaaa aggcatttga tatcctgcct   6780
ttcctacagc actcagatta aaacacaggc ttaaattaat tctgattgct tcctttttcc   6840
ttgttccttc ctgcagaggc tgatgggaca gtgtccaggg ctggagagcc acgtgttctg   6900
tagatgataa ataactatga acatttggtg ctgaattttt tacacttgtc tcttgtggtg   6960
ctatgtgtcc ggagaccctt aggtggccct agggtgcctg ccatgcctca ttccctcccc   7020
caccttcctt tatcctggcc atttctccac attctgagat tttgccaagg gacctgaaga   7080
ccagattggt gccagagacc tttcttccct cctggcacct tgtactcatg atggtgggga   7140
```

```
gtcccttcct gaagcctgtc cccctctctg ggctctgctt atgtcatttg aaaacacatg   7200

agcaaaacaa agacttcgtg catggccggc ccatggtgta cccatggtct tgttcagttg   7260

ctgaatgttt gtggtgctaa tctctgtgtg tgtgccaaga tggaatggaa gctgctgtgt   7320

gcccacctga cagccagact tcattgagag ccataggtgg cttgagaaat gtgggatgga   7380

ctctggctcc agggtcgctg agctgactga gtttccagca gaggagtgtc ctgggtgctg   7440

cagtcagtgc tggggtccat agggatccct ctggatgctg ccctcttcct cctctccctc   7500

ctcctccagg gtgtgtgtgg tggctgggcg ggaggggtgc tgccttctga gtgcagaggt   7560

ctccaggtcc aacaaggaaa acctcactga gagttacctg ccttccacca cgagaaagct   7620

gtggtgccca cagagagtca ctctggtgct tgtgtcccca ccccacccct gaagtgaaga   7680

aaacgaccgt gaggcacccg ggagcagcca ggattgatga acgccaccaa cacgcatccc   7740

ccaaagttcc ctgaagaaca agttctactc ttgccaaaga aatgcctggc ctggagagct   7800

ctcctggaag ccaggatgcc atcgtgagcc agggactgct gtgcatgcct ctgcatgaga   7860

aaaagccata ttggaagacg gccatacgcc ctgtggattc tgtgtaggtc atgtgattcg   7920

gattctgcct cccactccat ctgactttgc tctgtcctgt tcttctgtcg gtcccttcca   7980

cgttgtaatt tgcattgaaa cccaaaatgt gttctgttct cctcagtcca ctttagctcc   8040

aatattttac aataaaatta cttcttatat ttgca                              8075
```

```
<210> SEQ ID NO 10
<211> LENGTH: 1838
<212> TYPE: PRT
<213> ORGANISM: Mus musculus

<400> SEQUENCE: 10

Met Asp Val His Thr Arg Trp Lys Ala Ala Arg Pro Gly Ala Leu Leu
1               5                   10                  15

Leu Ser Ser Pro Leu Leu Leu Phe Leu Leu Leu Leu Trp Ala Pro Pro
            20                  25                  30

Ser Ser Arg Ala Ala Gln Pro Ala Asp Leu Leu Glu Met Leu Asp Phe
        35                  40                  45

His Asn Leu Pro Ser Gly Val Thr Lys Thr Thr Gly Phe Cys Ala Thr
    50                  55                  60

Arg Arg Ser Ser Ser Glu Pro Asp Val Ala Tyr Arg Val Ser Lys Asp
65                  70                  75                  80

Ala Gln Leu Ser Met Pro Thr Lys Gln Leu Tyr Pro Glu Ser Gly Phe
                85                  90                  95

Pro Glu Asp Phe Ser Ile Leu Thr Thr Val Lys Ala Lys Lys Gly Ser
            100                 105                 110

Gln Ala Phe Leu Val Ser Ile Tyr Asn Glu Gln Gly Ile Gln Gln Leu
        115                 120                 125

Gly Leu Glu Leu Gly Arg Ser Pro Val Phe Leu Tyr Glu Asp His Thr
    130                 135                 140

Gly Lys Pro Gly Pro Glu Glu Tyr Pro Leu Phe Pro Gly Ile Asn Leu
145                 150                 155                 160

Ser Asp Gly Lys Trp His Arg Ile Ala Leu Ser Val Tyr Lys Lys Asn
                165                 170                 175

Val Thr Leu Ile Leu Asp Cys Lys Lys Lys Ile Thr Lys Phe Leu Ser
            180                 185                 190

Arg Ser Asp His Pro Ile Ile Asp Thr Asn Gly Ile Val Met Phe Gly
        195                 200                 205
```

```
Ser Arg Ile Leu Asp Asp Glu Ile Phe Glu Gly Asp Ile Gln Gln Leu
    210                 215                 220

Leu Phe Val Ser Asp Asn Arg Ala Ala Tyr Asp Tyr Cys Glu His Tyr
225                 230                 235                 240

Ser Pro Asp Cys Asp Thr Ala Val Pro Asp Thr Pro Gln Ser Gln Asp
                245                 250                 255

Pro Asn Pro Asp Glu Tyr Tyr Pro Glu Gly Glu Gly Glu Thr Tyr Tyr
            260                 265                 270

Tyr Glu Tyr Pro Tyr Tyr Glu Asp Pro Glu Asp Pro Gly Lys Glu Pro
        275                 280                 285

Ala Pro Thr Gln Lys Pro Val Glu Ala Ala Arg Glu Thr Thr Glu Val
    290                 295                 300

Pro Glu Glu Gln Thr Gln Pro Leu Pro Glu Ala Pro Thr Val Pro Glu
305                 310                 315                 320

Thr Ser Asp Thr Ala Asp Lys Glu Asp Ser Leu Gly Ile Gly Asp Tyr
                325                 330                 335

Asp Tyr Val Pro Pro Asp Asp Tyr Tyr Thr Pro Pro Pro Tyr Glu Asp
            340                 345                 350

Phe Gly Tyr Gly Glu Gly Val Glu Asn Pro Asp Gln Pro Thr Asn Pro
        355                 360                 365

Asp Ser Gly Ala Glu Val Pro Thr Ser Thr Thr Val Thr Ser Asn Thr
    370                 375                 380

Ser Asn Pro Ala Pro Gly Glu Gly Lys Asp Asp Leu Gly Gly Glu Phe
385                 390                 395                 400

Thr Glu Glu Thr Ile Lys Asn Leu Glu Glu Asn Tyr Tyr Asp Pro Tyr
                405                 410                 415

Phe Asp Pro Asp Ser Asp Ser Ser Val Ser Pro Ser Glu Ile Gly Pro
            420                 425                 430

Gly Met Pro Ala Asn Gln Asp Thr Ile Phe Glu Gly Ile Gly Gly Pro
        435                 440                 445

Arg Gly Glu Lys Gly Gln Lys Gly Glu Pro Ala Ile Ile Glu Pro Gly
    450                 455                 460

Met Leu Ile Glu Gly Pro Pro Gly Pro Glu Gly Pro Ala Gly Leu Pro
465                 470                 475                 480

Gly Pro Pro Gly Thr Thr Gly Pro Thr Gly Gln Met Gly Asp Pro Gly
                485                 490                 495

Glu Arg Gly Pro Pro Gly Arg Pro Gly Leu Pro Gly Ala Asp Gly Leu
            500                 505                 510

Pro Gly Pro Pro Gly Thr Met Leu Met Leu Pro Phe Arg Phe Gly Gly
        515                 520                 525

Gly Gly Asp Ala Gly Ser Lys Gly Pro Met Val Ser Ala Gln Glu Ser
    530                 535                 540

Gln Ala Gln Ala Ile Leu Gln Gln Ala Arg Leu Ala Leu Arg Gly Pro
545                 550                 555                 560

Ala Gly Pro Met Gly Leu Thr Gly Arg Pro Gly Pro Met Gly Pro Pro
                565                 570                 575

Gly Ser Gly Gly Leu Lys Gly Glu Pro Gly Asp Met Gly Pro Gln Gly
            580                 585                 590

Pro Arg Gly Val Gln Gly Pro Pro Gly Pro Thr Gly Lys Pro Gly Arg
        595                 600                 605

Arg Gly Arg Ala Gly Ser Asp Gly Ala Arg Gly Met Pro Gly Gln Thr
    610                 615                 620
```

```
Gly Pro Lys Gly Asp Arg Gly Phe Asp Gly Leu Ala Gly Leu Pro Gly
625                 630                 635                 640

Glu Lys Gly His Arg Gly Asp Pro Gly Pro Ser Gly Pro Pro Gly Ile
                645                 650                 655

Pro Gly Asp Asp Gly Glu Arg Gly Asp Asp Gly Glu Val Gly Pro Arg
            660                 665                 670

Gly Leu Pro Gly Glu Pro Gly Pro Arg Gly Leu Leu Gly Pro Lys Gly
        675                 680                 685

Pro Pro Gly Pro Pro Gly Pro Pro Gly Val Thr Gly Met Asp Gly Gln
    690                 695                 700

Pro Gly Pro Lys Gly Asn Val Gly Pro Gln Gly Glu Pro Gly Pro Pro
705                 710                 715                 720

Gly Gln Gln Gly Asn Pro Gly Ala Gln Gly Leu Pro Gly Pro Gln Gly
                725                 730                 735

Ala Ile Gly Pro Pro Gly Glu Lys Gly Pro Leu Gly Lys Pro Gly Leu
            740                 745                 750

Pro Gly Met Pro Gly Ala Asp Gly Pro Pro Gly His Pro Gly Lys Glu
        755                 760                 765

Gly Pro Pro Gly Glu Lys Gly Gly Gln Gly Pro Pro Gly Pro Gln Gly
    770                 775                 780

Pro Ile Gly Tyr Pro Gly Pro Arg Gly Val Lys Gly Ala Asp Gly Ile
785                 790                 795                 800

Arg Gly Leu Lys Gly Thr Lys Gly Glu Lys Gly Glu Asp Gly Phe Pro
                805                 810                 815

Gly Phe Lys Gly Asp Met Gly Ile Lys Gly Asp Arg Gly Glu Ile Gly
            820                 825                 830

Pro Pro Gly Pro Arg Gly Glu Asp Gly Pro Glu Gly Pro Lys Gly Arg
        835                 840                 845

Gly Gly Pro Asn Gly Asp Pro Gly Pro Leu Gly Pro Thr Gly Glu Lys
    850                 855                 860

Gly Lys Leu Gly Val Pro Gly Leu Pro Gly Tyr Pro Gly Arg Gln Gly
865                 870                 875                 880

Pro Lys Gly Ser Ile Gly Phe Pro Gly Phe Pro Gly Ala Asn Gly Glu
                885                 890                 895

Lys Gly Gly Arg Gly Thr Pro Gly Lys Pro Gly Pro Arg Gly Gln Arg
            900                 905                 910

Gly Pro Thr Gly Pro Arg Gly Glu Arg Gly Pro Arg Gly Ile Thr Gly
        915                 920                 925

Lys Pro Gly Pro Lys Gly Asn Ser Gly Gly Asp Gly Pro Ala Gly Pro
    930                 935                 940

Pro Gly Glu Arg Gly Pro Asn Gly Pro Gln Gly Pro Thr Gly Phe Pro
945                 950                 955                 960

Gly Pro Lys Gly Pro Pro Gly Pro Pro Gly Lys Asp Gly Leu Pro Gly
                965                 970                 975

His Pro Gly Gln Arg Gly Glu Thr Gly Phe Gln Gly Lys Thr Gly Pro
            980                 985                 990

Pro Gly Pro Pro Gly Val Val Gly  Pro Gln Gly Pro Thr  Gly Glu Thr
        995                 1000                1005

Gly Pro  Met Gly Glu Arg Gly  His Pro Gly Pro Pro  Gly Pro Pro
    1010                1015                1020

Gly Glu  Gln Gly Leu Pro Gly  Ala Ala Gly Lys Glu  Gly Thr Lys
    1025                1030                1035

Gly Asp  Pro Gly Pro Ala Gly  Leu Pro Gly Lys Asp  Gly Pro Pro
```

```
    1040                1045                1050

Gly Leu  Arg Gly Phe Pro Gly  Asp Arg Gly Leu Pro  Gly Pro Val
    1055                1060                1065

Gly Ala  Leu Gly Leu Lys Gly  Ser Glu Gly Pro Pro  Gly Pro Pro
    1070                1075                1080

Gly Pro  Ala Gly Ser Pro Gly  Glu Arg Gly Pro Ala  Gly Ala Ala
    1085                1090                1095

Gly Pro  Ile Gly Ile Pro Gly  Arg Pro Gly Pro Gln  Gly Pro Pro
    1100                1105                1110

Gly Pro  Ala Gly Glu Lys Gly  Leu Pro Gly Glu Lys  Gly Pro Gln
    1115                1120                1125

Gly Pro  Ala Gly Arg Asp Gly  Leu Gln Gly Pro Val  Gly Leu Pro
    1130                1135                1140

Gly Pro  Ala Gly Pro Val Gly  Pro Pro Gly Glu Asp  Gly Asp Lys
    1145                1150                1155

Gly Glu  Ile Gly Glu Pro Gly  Gln Lys Gly Ser Lys  Gly Asp Lys
    1160                1165                1170

Gly Glu  Gln Gly Pro Pro Gly  Pro Thr Gly Pro Gln  Gly Pro Ile
    1175                1180                1185

Gly Gln  Pro Gly Pro Ser Gly  Ala Asp Gly Glu Pro  Gly Pro Arg
    1190                1195                1200

Gly Gln  Gln Gly Leu Phe Gly  Gln Lys Gly Asp Glu  Gly Ser Arg
    1205                1210                1215

Gly Phe  Pro Gly Pro Pro Gly  Pro Val Gly Leu Gln  Gly Leu Pro
    1220                1225                1230

Gly Pro  Pro Gly Glu Lys Gly  Glu Thr Gly Asp Val  Gly Gln Met
    1235                1240                1245

Gly Pro  Pro Gly Pro Pro Gly  Pro Arg Gly Pro Ser  Gly Ala Pro
    1250                1255                1260

Gly Ala  Asp Gly Pro Gln Gly  Pro Pro Gly Gly Ile  Gly Asn Pro
    1265                1270                1275

Gly Ala  Val Gly Glu Lys Gly  Glu Pro Gly Glu Ala  Gly Asp Pro
    1280                1285                1290

Gly Leu  Pro Gly Glu Gly Gly  Pro Leu Gly Pro Lys  Gly Glu Arg
    1295                1300                1305

Gly Glu  Lys Gly Glu Ala Gly  Pro Ser Gly Ala Ala  Gly Pro Pro
    1310                1315                1320

Gly Pro  Lys Gly Pro Pro Gly  Asp Asp Gly Pro Lys  Gly Ser Pro
    1325                1330                1335

Gly Pro  Val Gly Phe Pro Gly  Asp Pro Gly Pro Pro  Gly Glu Pro
    1340                1345                1350

Gly Pro  Ala Gly Gln Asp Gly  Pro Pro Gly Asp Lys  Gly Asp Asp
    1355                1360                1365

Gly Glu  Pro Gly Gln Thr Gly  Ser Pro Gly Pro Thr  Gly Glu Pro
    1370                1375                1380

Gly Pro  Ser Gly Pro Pro Gly  Lys Arg Gly Pro Pro  Gly Pro Ala
    1385                1390                1395

Gly Pro  Glu Gly Arg Gln Gly  Glu Lys Gly Ala Lys  Gly Glu Ala
    1400                1405                1410

Gly Leu  Glu Gly Pro Pro Gly  Lys Thr Gly Pro Ile  Gly Pro Gln
    1415                1420                1425

Gly Ala  Pro Gly Lys Pro Gly  Pro Asp Gly Leu Arg  Gly Ile Pro
    1430                1435                1440
```

```
Gly Pro  Val Gly Glu Gln Gly  Leu Pro Gly Ser Pro  Gly Pro Asp
    1445                 1450                 1455

Gly Pro  Pro Gly Pro Met Gly  Pro Pro Gly Leu Pro  Gly Leu Lys
    1460                 1465                 1470

Gly Asp  Ser Gly Pro Lys Gly  Glu Lys Gly His Pro  Gly Leu Ile
    1475                 1480                 1485

Gly Leu  Ile Gly Pro Pro Gly  Glu Gln Gly Glu Lys  Gly Asp Arg
    1490                 1495                 1500

Gly Leu  Pro Gly Pro Gln Gly  Ser Ser Gly Pro Lys  Gly Asp Gln
    1505                 1510                 1515

Gly Ile  Thr Gly Pro Ser Gly  Pro Leu Gly Pro Pro  Gly Pro Pro
    1520                 1525                 1530

Gly Leu  Pro Gly Pro Pro Gly  Pro Lys Gly Ala Lys  Gly Ser Ser
    1535                 1540                 1545

Gly Pro  Thr Gly Pro Lys Gly  Glu Ala Gly His Pro  Gly Leu Pro
    1550                 1555                 1560

Gly Pro  Pro Gly Pro Pro Gly  Glu Val Ile Gln Pro  Leu Pro Ile
    1565                 1570                 1575

Gln Ala  Ser Arg Thr Arg Arg  Asn Ile Asp Ala Ser  Gln Leu Leu
    1580                 1585                 1590

Asp Asp  Gly Ala Gly Glu Ser  Tyr Val Asp Tyr Ala  Asp Gly Met
    1595                 1600                 1605

Glu Glu  Ile Phe Gly Ser Leu  Asn Ser Leu Lys Leu  Glu Ile Glu
    1610                 1615                 1620

Gln Met  Lys Arg Pro Leu Gly  Thr Gln Gln Asn Pro  Ala Arg Thr
    1625                 1630                 1635

Cys Lys  Asp Leu Gln Leu Cys  His Pro Asp Phe Pro  Asp Gly Glu
    1640                 1645                 1650

Tyr Trp  Val Asp Pro Asn Gln  Gly Cys Ser Arg Asp  Ser Phe Lys
    1655                 1660                 1665

Val Tyr  Cys Asn Phe Thr Ala  Gly Gly Ser Thr Cys  Val Phe Pro
    1670                 1675                 1680

Asp Lys  Lys Ser Glu Gly Ser  Lys Met Ala Arg Trp  Pro Lys Glu
    1685                 1690                 1695

Gln Pro  Ser Thr Trp Tyr Ser  Gln Tyr Lys Arg Gly  Ser Leu Leu
    1700                 1705                 1710

Ser Tyr  Val Asp Ala Glu Gly  Asn Pro Val Gly Val  Val Gln Met
    1715                 1720                 1725

Thr Phe  Leu Arg Leu Leu Ser  Ala Ser Ala His Gln  Asn Val Thr
    1730                 1735                 1740

Tyr Asn  Cys Tyr Gln Ser Val  Ala Trp Gln Asp Ala  Ala Thr Gly
    1745                 1750                 1755

Ser Tyr  Asp Lys Ala Ile Arg  Phe Leu Gly Ser Asn  Asp Glu Glu
    1760                 1765                 1770

Met Ser  Tyr Asp Asn Asn Pro  Tyr Ile Arg Ala Leu  Val Asp Gly
    1775                 1780                 1785

Cys Ala  Thr Lys Lys Gly Tyr  Gln Lys Thr Val Leu  Glu Ile Asp
    1790                 1795                 1800

Thr Pro  Lys Val Glu Gln Val  Pro Ile Val Asp Ile  Met Phe Asn
    1805                 1810                 1815

Asp Phe  Gly Glu Ala Ser Gln  Lys Phe Gly Phe Glu  Val Gly Pro
    1820                 1825                 1830
```

Ala Cys Phe Leu Gly
1835

<210> SEQ ID NO 11
<211> LENGTH: 3934
<212> TYPE: DNA
<213> ORGANISM: Mus musculus

<400> SEQUENCE: 11

```
gtccgggccc cgcccggcaa gggctctaga gcgcagggcg cggccagggc ggggtctcgg     60
gcagtctcca gcagatcctc acagcctccg gctgtccaga gtgactgctc ccaggaagac    120
cagtccacat ccccttggc cttggtgcac caggccccgc tgggatgaga agctgccgga    180
gactggatca gcttcaggcc ggcctctgcc tgctcctggc ctccctgcag ctcgtgtcct    240
ggacgctggc tgcagaacct gtggacgtac tggaagcctg ggtgtgcat agagaccagg    300
ctggggtggc tgaagggcct ggcttctgcc ccctgaggat tccacagggt gaccgagcat    360
tcagggtggg caagtccagc cttctcagtg tccccacgtg gcagctcttc ccagatgggc    420
attttcctga gaacttttct gtgctgctca cactgagggc ccagccagcc aatcagtctg    480
tccttctgtc tatttatgat gagaagggtg tccggcagct ggggctggca ctggggccag    540
ctctgggcct ccttggtgac tccttcaggc ccctccccaa gcaagtcaac attatggatg    600
gcaggtggca ccgtgtggca gtcagcatca gtggtaacaa ggtgaccctg gtggttgact    660
gtgaaccgca gcccccaaca tttggtcagg ggcctcggtt tataagtaca gctggactca    720
ctgtgatggg aacccaggac accagggaag agtcttttga gggagacatc caggagctgc    780
tgttaattcc agaccctcag gctgccttcc aggcctgtga gagctacctc cctggttgtg    840
aaaccctcga ttccacaacc acagggggccc ccaaagacga tgaaccagaa acccctgccc    900
ctcgtcgtcg aaagggcaaa gggaagaaaa aagggcgggg tcgaaagggc aagggaagaa    960
agaaaaacaa ggagacctca gagctgagtc cgacccctgg tgcccctgag aaccagacct   1020
ccctccacat ccctgagaca gagaagacag ttccccacct gcctctgact cccacacctc   1080
tggccatcac caccactgtc acgattggac aaaatgccac agtctcgcag gggttggact   1140
ccggtactga aaccgagcag acgactccag aggtggactc tactgaggag ggtgaaggag   1200
gtggccccac catgggcccc aagttccggg cagcagagca gtccttacag actgagttcc   1260
agatctttcc tggtgctgga gaaaagggag cgaaaggaga gcctgcgaca gtagagcagg   1320
gacagcagtt tgaggggcct gcaggagctc caggaccccg ggaatatct ggtccttcag    1380
gccctcctgg gcctccgggc ttccctgggg accgtggtct accgggtcct gccggcctcc   1440
caggaatccc aggcatcgat ggagcccggg gcctgccggg cacagtgatt atgatgccgt   1500
tccattttgc aagcagctcg atgaagggac cccagtgtc cttccagcag gcccaggccc    1560
aggcagtatt gcaacaggct cagctgtcca tgaaagggcc ccctggtcca gtagggctca   1620
ctgggcgccc aggccctgtg ggcctccctg gatatccagg tctgaaaggt gaactgggag   1680
aagtggggcc acagggcccc cgaggattac agggccctcc tgggcctcct ggacgggaag   1740
gcaagacagg ccgagctgga gcagatgggg ctcgggggct cccgggagac acaggaccta   1800
agggtgacag gggctttgat ggcctgcccg ggctgcctgg tgagaagggc caaaggggtg   1860
actttggacg agtagggcaa cctggtcccc caggagagga tggtgtaaag ggcctgcagg   1920
gacctccagg gcccactggc caggctggag agccgggtcc ccgaggtctg attggcccca   1980
gaggtctccc aggtccccta ggacgcccgg gtgtgacagg gagtgatggc gcaccagggg   2040
```

-continued

```
ccaaaggcaa cgtgggtcct cctggagaac caggaccccc aggacagcaa ggaaaccacg   2100

gctcccaggg aattccaggc ccccaggggc ccattggcac tcccggggaa aagggtcccc   2160

ctggaaaccc cggaattcca ggtgtcccag gatctgaggg ccccccgggc cacccaggcc   2220

acgagggtcc cacaggagaa aaaggggctc agggcccacc aggatcagca ggccctcggg   2280

gctatcctgg acttcgtggt gtgaagggta cctctggtaa ccggggtctc caaggcgaga   2340

aaggagaaag gggagaggat ggctttcctg gcttcaaggg tgatgaggga ccaaaaggcg   2400

accggggaaa ccccggaccc ccaggtccca gaggagagga tggtccagaa ggacaaaagg   2460

ggcctggggg actgcctggt gatgagggtc ctccaggagc agcaggggag aagggcaagc   2520

ttggggtgcc aggtctccca ggttatccag gacgcccagg acctaaggga tctattggat   2580

ttcctggacc cttgggacca ctgggggaga aaggcaagcg gggcaaagca ggacagccag   2640

gagaggaagg agaacgcggc acaccgggca cccgaggaga caggggacag ccgggggcca   2700

caggccagcc tggccccaag ggtgacgtgg gccagaatgg gtctcctggg ccccctggag   2760

aaaagggtct acccggtctt caaggcccac caggattccc cggaccaaaa ggcccccccgg   2820

gtcctcaggg gaaagatggg atatctgggc accctggaca aagaggagaa ttgggcttcc   2880

aaggtctgac aggcccccct ggaccagctg gcgtccttgg tcctcaggga aaggtagggg   2940

acgtggggcc tctaggcgag agaggccccc cagggcctcc tggacctcct ggtgaacaag   3000

gtctgccagg catagaaggc agagaagggg ccaagggtga gctaggaccc ctggggtccg   3060

tcgggaagga ggggccacct gggcccaggg gcttccctgg cccccaagga gcccccggag   3120

acccaggacc cattggtttg aagggtgaca aaggtccccc aggccctgtt ggggcaaatg   3180

gctccccggg agagcgtggt cctgtaggcc cctctggtgg cattgggctt cctggccaga   3240

gtggagggca aggccctatt ggtcctgctg gcgagaaggg gtccccggga gaacggggta   3300

ctcctggtcc tactggcaaa gatggtattc caggaccccc ggggcttcag ggcccctctg   3360

gagctgcggg gccttctggg gaagaaggag acaaggggga agtagggatg cctggtcaca   3420

aaggaagcaa aggggataaa ggagatgcag gcccacctgg accaacagga ataagaggtc   3480

cagcaggcca ttcaggcctc ccgaaacaac tgtatatacg atgctgcatt tcttaataag   3540

cttactcagc ataagacatg gcttgtgcga gacccccgtc cccagctctc tgtcttcttt   3600

gccttcccat ctcctgggca tttttccctt aggaccctgt cactgaagaa tgacctgctg   3660

gtccaggtca gagtgtcacc aaaacattag gtcataactt ccaacctagc cctaaaacct   3720

accccagcct cctacaaacc ttacctgctc ataaccttac ctgagccaca tccctgattc   3780

actgtgtcag taactcagaa acatcacctg ccctttacat caaactaaaa cctgattctc   3840

accaaacttg atcccaaccc ctagcctcag tcctgacctt ggaccctgtc tgcagccttt   3900

gatctggaca ccaactgtgt tgtccccaac attt                                3934
```

<210> SEQ ID NO 12
<211> LENGTH: 1123
<212> TYPE: PRT
<213> ORGANISM: Mus musculus

<400> SEQUENCE: 12

```
Met Arg Ser Cys Arg Arg Leu Asp Gln Leu Gln Ala Gly Leu Cys Leu
1               5                   10                  15

Leu Leu Ala Ser Leu Gln Leu Val Ser Trp Thr Leu Ala Ala Glu Pro
            20                  25                  30

Val Asp Val Leu Glu Ala Trp Gly Val His Arg Asp Gln Ala Gly Val
```

```
        35                  40                  45

Ala Glu Gly Pro Gly Phe Cys Pro Leu Arg Ile Pro Gln Gly Asp Arg
    50                  55                  60

Ala Phe Arg Val Gly Lys Ser Ser Leu Leu Ser Val Pro Thr Trp Gln
65                  70                  75                  80

Leu Phe Pro Asp Gly His Phe Pro Glu Asn Phe Ser Val Leu Leu Thr
                85                  90                  95

Leu Arg Ala Gln Pro Ala Asn Gln Ser Val Leu Leu Ser Ile Tyr Asp
            100                 105                 110

Glu Lys Gly Val Arg Gln Leu Gly Leu Ala Leu Gly Pro Ala Leu Gly
        115                 120                 125

Leu Leu Gly Asp Ser Phe Arg Pro Leu Pro Lys Gln Val Asn Ile Met
    130                 135                 140

Asp Gly Arg Trp His Arg Val Ala Val Ser Ile Ser Gly Asn Lys Val
145                 150                 155                 160

Thr Leu Val Val Asp Cys Glu Pro Gln Pro Pro Thr Phe Gly Gln Gly
                165                 170                 175

Pro Arg Phe Ile Ser Thr Ala Gly Leu Thr Val Met Gly Thr Gln Asp
            180                 185                 190

Thr Arg Glu Glu Ser Phe Glu Gly Asp Ile Gln Glu Leu Leu Leu Ile
        195                 200                 205

Pro Asp Pro Gln Ala Ala Phe Gln Ala Cys Glu Ser Tyr Leu Pro Gly
    210                 215                 220

Cys Glu Thr Leu Asp Ser Thr Thr Thr Gly Ala Pro Lys Asp Asp Glu
225                 230                 235                 240

Pro Glu Thr Pro Ala Pro Arg Arg Arg Lys Gly Lys Gly Lys Lys Lys
                245                 250                 255

Gly Arg Gly Arg Lys Gly Lys Gly Arg Lys Lys Asn Lys Glu Thr Ser
            260                 265                 270

Glu Leu Ser Pro Thr Pro Gly Ala Pro Glu Asn Gln Thr Ser Leu His
        275                 280                 285

Ile Pro Glu Thr Glu Lys Thr Val Pro His Leu Pro Leu Thr Pro Thr
    290                 295                 300

Pro Leu Ala Ile Thr Thr Thr Val Thr Ile Gly Gln Asn Ala Thr Val
305                 310                 315                 320

Ser Gln Gly Leu Asp Ser Gly Thr Glu Thr Glu Gln Thr Thr Pro Glu
                325                 330                 335

Val Asp Ser Thr Glu Glu Gly Glu Gly Gly Gly Pro Thr Met Gly Pro
            340                 345                 350

Lys Phe Arg Ala Ala Glu Gln Ser Leu Gln Thr Glu Phe Gln Ile Phe
        355                 360                 365

Pro Gly Ala Gly Glu Lys Gly Ala Lys Gly Glu Pro Ala Thr Val Glu
    370                 375                 380

Gln Gly Gln Gln Phe Glu Gly Pro Ala Gly Ala Pro Gly Pro Arg Gly
385                 390                 395                 400

Ile Ser Gly Pro Ser Gly Pro Pro Gly Pro Pro Gly Phe Pro Gly Asp
                405                 410                 415

Arg Gly Leu Pro Gly Pro Ala Gly Leu Pro Gly Ile Pro Gly Ile Asp
            420                 425                 430

Gly Ala Arg Gly Leu Pro Gly Thr Val Ile Met Met Pro Phe His Phe
        435                 440                 445

Ala Ser Ser Ser Met Lys Gly Pro Pro Val Ser Phe Gln Gln Ala Gln
    450                 455                 460
```

```
Ala Gln Ala Val Leu Gln Gln Ala Gln Leu Ser Met Lys Gly Pro Pro
465                 470                 475                 480

Gly Pro Val Gly Leu Thr Gly Arg Pro Gly Pro Val Gly Leu Pro Gly
                485                 490                 495

Tyr Pro Gly Leu Lys Gly Glu Leu Gly Glu Val Gly Pro Gln Gly Pro
            500                 505                 510

Arg Gly Leu Gln Gly Pro Pro Gly Pro Pro Gly Arg Glu Gly Lys Thr
        515                 520                 525

Gly Arg Ala Gly Ala Asp Gly Ala Arg Gly Leu Pro Gly Asp Thr Gly
    530                 535                 540

Pro Lys Gly Asp Arg Gly Phe Asp Gly Leu Pro Gly Leu Pro Gly Glu
545                 550                 555                 560

Lys Gly Gln Arg Gly Asp Phe Gly Arg Val Gly Gln Pro Gly Pro Pro
                565                 570                 575

Gly Glu Asp Gly Val Lys Gly Leu Gln Gly Pro Pro Gly Pro Thr Gly
            580                 585                 590

Gln Ala Gly Glu Pro Gly Pro Arg Gly Leu Ile Gly Pro Arg Gly Leu
        595                 600                 605

Pro Gly Pro Leu Gly Arg Pro Gly Val Thr Gly Ser Asp Gly Ala Pro
    610                 615                 620

Gly Ala Lys Gly Asn Val Gly Pro Pro Gly Glu Pro Gly Pro Pro Gly
625                 630                 635                 640

Gln Gln Gly Asn His Gly Ser Gln Gly Ile Pro Gly Pro Gln Gly Pro
                645                 650                 655

Ile Gly Thr Pro Gly Glu Lys Gly Pro Pro Gly Asn Pro Gly Ile Pro
            660                 665                 670

Gly Val Pro Gly Ser Glu Gly Pro Pro Gly His Pro Gly His Glu Gly
        675                 680                 685

Pro Thr Gly Glu Lys Gly Ala Gln Gly Pro Pro Gly Ser Ala Gly Pro
    690                 695                 700

Arg Gly Tyr Pro Gly Leu Arg Gly Val Lys Gly Thr Ser Gly Asn Arg
705                 710                 715                 720

Gly Leu Gln Gly Glu Lys Gly Glu Arg Gly Glu Asp Gly Phe Pro Gly
                725                 730                 735

Phe Lys Gly Asp Glu Gly Pro Lys Gly Asp Arg Gly Asn Pro Gly Pro
            740                 745                 750

Pro Gly Pro Arg Gly Glu Asp Gly Pro Glu Gly Gln Lys Gly Pro Gly
        755                 760                 765

Gly Leu Pro Gly Asp Glu Gly Pro Pro Gly Ala Ala Gly Glu Lys Gly
    770                 775                 780

Lys Leu Gly Val Pro Gly Leu Pro Gly Tyr Pro Gly Arg Pro Gly Pro
785                 790                 795                 800

Lys Gly Ser Ile Gly Phe Pro Gly Pro Leu Gly Pro Leu Gly Glu Lys
                805                 810                 815

Gly Lys Arg Gly Lys Ala Gly Gln Pro Gly Glu Glu Gly Glu Arg Gly
            820                 825                 830

Thr Pro Gly Thr Arg Gly Asp Arg Gly Gln Pro Gly Ala Thr Gly Gln
        835                 840                 845

Pro Gly Pro Lys Gly Asp Val Gly Gln Asn Gly Ser Pro Gly Pro Pro
    850                 855                 860

Gly Glu Lys Gly Leu Pro Gly Leu Gln Gly Pro Pro Gly Phe Pro Gly
865                 870                 875                 880
```

```
Pro Lys Gly Pro Pro Gly Pro Gln Gly Lys Asp Gly Ile Ser Gly His
                885                 890                 895

Pro Gly Gln Arg Gly Glu Leu Gly Phe Gln Gly Leu Thr Gly Pro Pro
            900                 905                 910

Gly Pro Ala Gly Val Leu Gly Pro Gln Gly Lys Val Gly Asp Val Gly
        915                 920                 925

Pro Leu Gly Glu Arg Gly Pro Pro Gly Pro Pro Gly Pro Pro Gly Glu
    930                 935                 940

Gln Gly Leu Pro Gly Ile Glu Gly Arg Glu Gly Ala Lys Gly Glu Leu
945                 950                 955                 960

Gly Pro Leu Gly Ser Val Gly Lys Glu Gly Pro Pro Gly Pro Arg Gly
                965                 970                 975

Phe Pro Gly Pro Gln Gly Ala Pro Gly Asp Pro Gly Pro Ile Gly Leu
            980                 985                 990

Lys Gly Asp Lys Gly Pro Pro Gly  Pro Val Gly Ala Asn  Gly Ser Pro
        995                 1000                1005

Gly Glu  Arg Gly Pro Val Gly  Pro Ser Gly Gly Ile  Gly Leu Pro
    1010                 1015                 1020

Gly Gln  Ser Gly Gly Gln Gly  Pro Ile Gly Pro Ala  Gly Glu Lys
    1025                 1030                 1035

Gly Ser  Pro Gly Glu Arg Gly  Thr Pro Gly Pro Thr  Gly Lys Asp
    1040                 1045                 1050

Gly Ile  Pro Gly Pro Pro Gly  Leu Gln Gly Pro Ser  Gly Ala Ala
    1055                 1060                 1065

Gly Pro  Ser Gly Glu Glu Gly  Asp Lys Gly Glu Val  Gly Met Pro
    1070                 1075                 1080

Gly His  Lys Gly Ser Lys Gly  Asp Lys Gly Asp Ala  Gly Pro Pro
    1085                 1090                 1095

Gly Pro  Thr Gly Ile Arg Gly  Pro Ala Gly His Ser  Gly Leu Pro
    1100                 1105                 1110

Lys Gln  Leu Tyr Ile Arg Cys  Cys Ile Ser
    1115                 1120
```

```
<210> SEQ ID NO 13
<211> LENGTH: 7705
<212> TYPE: DNA
<213> ORGANISM: Mus musculus

<400> SEQUENCE: 13

gcgagcctct tgtccagccc acccacagca tgaagccttt aggggtgctc agtgctttcg      60

gctttttttc ttgaaaccct tcatctgccc tcagtctgaa ggcagggtca ggcgtaggac     120

gggtcccggg gtcgcagtct cctgcgggcc accccaaagg gagaggaggg ggcgagagac     180

aggaaggaag caaaccatca aattggaaaa aaaaaaatta gagccctttg acttttttttt     240

tttttactcc ctttcccttc cggatggctg tgtagcgaac gtaggcgaca ccttggaagg     300

gacaaagttg gtctgcagtg gcaatttcgt gggttcacag tcgtgagcgt ggggcttgga     360

gatggagccc tggtccaggt ggaaaacgaa acggtggatc tgggatctca ccatctcaac     420

cctcgccttg acttttctct tccaagctag agaggtcaga ggagctgctc cagttgatat     480

actaaaagca ttagattttc acaattctcc agtgggaata tctaaaacaa caggattttg     540

cacaaacaga aagaattcta aagatccaga tgttgcttat agagttacgg aggaagcaca     600

aatcagcgcc ccaacaaagc agctatttcc aggaggaatt tttccacaag atttttcaat     660

actatttaca ataaaaccca aaaaaggaac tcaagctttc ctcttgtccc tctacaatga     720
```

-continued

```
acatggcatt cagcaactcg gtgttgaggt tgggagatcg cccgtttttc tatttgaaga    780
ccacactgga aaacccacac cggaaaacta tcctctcttc tcaacagtta acattgctga    840
tggcaagtgg caccgggtcg caatcagtgt ggagaagaaa actgtgacaa tgattgttga    900
ttgtaagaag aaaatcacaa aacccctcga tagaagtgag agatcgatag tcgataccaa    960
tggaatcatg gtatttggaa caagaatttt agaaacagat gttttccagg gtgatattca   1020
gcagttcctg atcacaggag accccaaggc agcatacgac tactgtgacc attacagtcc   1080
agattgtgac ttaacatcca aggctgccca ggctcaggag cctcacattg atgagtatgc   1140
acctgaggat ataatcgagt atgactatga atatggggag acagactata aagaggctga   1200
gagtgtaaca gagatgccta cttttactga agaaacagta gcacaaacag aggcaaatat   1260
tgtggatgat tttcaagact acaactatgg aacaatggaa ccttaccaga ctgagactcc   1320
taggcgggta tcaggatcga atgagccaaa tccagttgaa gaaggtttta ctgaagaata   1380
tctaaccgga gaggattatg atgtccagag aaacacttcc gaggatattc tgtacgggaa   1440
caaaggagta gacggcaggg attctgatct cctggtagat ggagatttag gtgaatatga   1500
tttttatgaa tacaaagaat atgaagaaag gactacgacc tcccctaatg aagaatttgg   1560
cccaggtgtc ccagcagaaa ctgatttcac agaaacaagc ataaatggac atggtgcata   1620
tggagagaaa gggcagaagg gggaaccggc tgtggttgaa cccgggatgc ttgttgaagg   1680
accacctggg ccagcaggac cagcgggtct tatgggtcct ccagggctac aaggtccttc   1740
tgggcttccc ggcgaccctg gggatagggg cccaccagga cgtcctggct taccaggggc   1800
tgatggttta cctggacctc ctggaaccat gctgatgtta ccattccgct atgggggtga   1860
cggctccaaa ggaccaacaa tctctgcaca ggaagcccaa gctcaggcga ttcttcagca   1920
ggctcggatt gctctgagag gccctcctgg cccaatgggt cttactggaa gaccaggtcc   1980
tgtggggggt cctggttcag ctggagccaa aggtgagagt ggggatccag gtcctcaggg   2040
tcctcgaggt gtccaaggtc ctcctggtcc aacgggaaag cctggaaaga ggggccgtcc   2100
aggtgctgat ggaggaagag gcatgccagg agaatctggg tctaagggag accgagggtt   2160
tgatggactt ccaggtctgc ctggtgacaa aggtcacagg ggagaaagag gtccacaagg   2220
tccacctggc ctccctggcg atgatggaat gaggggagaa gatggggaga tcgggcccag   2280
gggtcttcca ggtgaagctg gtccaagagg cttgctggga ccaaggggaa ctccaggacc   2340
ccctgggcag cctggtatcg gaggtataga tggcccccaa ggaccaaaag gaaacatggg   2400
tccccaaggg gagcctggac caccaggtca gcaaggaaat ccaggacctc aaggacttcc   2460
tggtccacaa ggcccaattg gccctccagg agaaaaaggg ccacaaggaa aaccagggct   2520
tgcgggactt cctggtgctg atggacctcc tggtcatcct gggaaagaag gccagtctgg   2580
agaaaagggt gccctgggtc ctcctggtcc tcaggggcct attggttatc ctggtccccg   2640
tggagtaaag ggagcagatg gtgtcagagg tctcaagggc tctaaaggcg aaaagggtga   2700
agatggcttt ccaggattca aaggtgacat gggtcttaaa ggtgacagag gcgaggtggg   2760
tcaagttggc ccaagaggag aagatggccc tgaaggcccc aaaggccgtg caggcccaac   2820
tggagaccca ggtccctctg gccaagcagg agagaaggga aaacttgggg ttccaggatt   2880
gccgggatat ccaggaagac aaggtccaaa gggatccact ggatttcctg gatttccagg   2940
tgccaacggg gagaaaggtg cccggggaat tgctggcaaa ccaggccccc ggggacagcg   3000
tggtccaacg ggtcctcgag gttccagagg cgccagaggt cccacgggaa aacctggtcc   3060
```

```
gaagggtact tcaggtggtg atggccctcc tggtcctcca ggcgaaaggg gccctcaagg   3120
acctcaaggt ccagttggat tccctggacc aaaaggcccc cctggccctg ctgggaaaga   3180
tgggctacca ggacaccctg ggcagcgtgg tgagactgga tttcaaggca agacaggtcc   3240
ccctggacca ggaggtgtgg taggaccaca gggaccaact ggtgagactg gtcctatagg   3300
tgaacgtggc catcccggcc ctcctggtcc tcctggcgag caaggacttc ccggtgctgc   3360
agggaaagaa ggtgcaaagg gtgatcccgg gcctcaaggt atctcaggaa aagatggacc   3420
agcaggaata cgcggtttcc caggtgaaag aggccttcct ggagcccagg gtgcacctgg   3480
gctgaaagga ggagaaggtc cccagggccc acagggtcca gttggctctc ctggagagcg   3540
aggctcagca ggcacagcag gcccaattgg tttgccagga cgtccaggcc cccagggtcc   3600
tcctggtcca gctggagaaa aaggtgctcc tggagaaaag ggtccccagg gtcctgcagg   3660
tagagatggt gtccaaggcc ctgtgggtct cccaggacct gctggtcctg ctggctctcc   3720
tggagaagat ggagacaagg gtgaaattgg tgaaccaggc caaaagggca gcaaaggtga   3780
caaaggcgaa aatggtcctc ctggtccccc cggacttcaa ggacctgttg gtgctcctgg   3840
aatcgctgga ggcgatggtg agccaggtcc ccgaggacag cagggaatgt ttggacaaaa   3900
aggtgatgag ggcgcacgag gtttcccagg acttcctggc cccataggtc ttcaggggtt   3960
gccaggccca ccaggtgaaa agggcgaaaa tggagacgtt ggccccatgg gtccaccagg   4020
tcctcctggc ccacgaggcc ctcaaggtcc caatggagct gatggaccac aaggaccccc   4080
aggctccatt ggttcagttg gtgttgtggg agacaagggt gaacctggag aagcagggaa   4140
cccagggccc cctggggaag ctggctctgg tggtctcaaa ggagagagag gagagaaagg   4200
agaagctggg ccccctggtg ctgcaggtcc tgctggtatt aaggggccac caggtgatga   4260
tgggcccaag gggaacccgg gacccgttgg gtttcctgga gatcctggtc cacctggaga   4320
acctggtcct gcagggcaag atggtgttgg aggtgacaag ggtgaagatg gagatccagg   4380
acaaccaggt ccccctggtc catctggtga agctggccct ccaggtcctc ctgggaagag   4440
aggtccgcct ggagcttcag gttcagaagg aaggcaagga gaaaaaggtg ctaagggaga   4500
agctggtgct gaaggacctc ctgggaaaac tggccctgtc ggacctcagg gaccttctgg   4560
aaagcctggt ccagaaggtc ttcgaggcat ccctggtcct gtgggagaac aaggtctccc   4620
aggtgctgct ggccaagatg gacctcctgg tcctctggga cctcctggtt tacctggtct   4680
caaaggtgac cctggatcca agggtgaaaa gggacatcct ggtttaattg gattgattgg   4740
tcctccagga gaacaagggg aaaaaggtga cagaggactt cctgggactc aaggttctcc   4800
aggagccaaa ggcgatgggg gcatcccagg tcctgctggt cccataggtc cccctggtcc   4860
tccaggatta ccaggtcccg ctggcccgaa gggtaacaaa ggatcatctg gacctactgg   4920
ccagaagggt gacagtggta tgccagggcc tcccgggcct ccaggtcctc ctggagaagt   4980
gatacagcct ttgcctattt tgtcaccaaa aaagaccaga agacacactg aaagcatcca   5040
gggtgatgca ggagataata ttcttgacta ctcagatggc atggaggaga tatttggttc   5100
cctcaattct ctgaaacaag acattgaaca catgaagttt cccatgggca cacagaccaa   5160
cccagcacga acatgcaaag acctgcaact cagccatccc gacttcccag atggtgaata   5220
ttggattgat cctaaccaag gttgttcagg tgattccttc aaagtttact gtaatttcac   5280
agctggtggt gagacatgca tctatccgga taaaaaatct gagggagtaa gaatttcatc   5340
gtggccaaag gagaaaccag gaagttggta cagtgaattt aagagaggaa aactgctttc   5400
atatttagat gtggaaggca attccataaa tatggtacaa atgacattcc tgaagctcct   5460
```

```
gactgcctct gcccggcaaa acttcaccta caattgccat cagtcagctg cctggtatga   5520
cgtattatca ggaagttatg acaaagcact tcgatttctg ggatcaaatg atgaggaaat   5580
gtcctatgag aacaacccac acatcaaagc tttgtatgat ggctgtgcgt ctcgaaaagg   5640
ctatgaaaag acagtgattg agatcaatac tccgaaaatt gatcaggtac ccatcattga   5700
tgtaatgatc aatgattttg gtgatcagaa ccagaagttt ggatttgaag tcggtccagc   5760
ttgctttctt ggataagatt aggacgaaga ccttatgaaa ccaacaggaa aaaaaatacc   5820
ttggtgccac caaccatttt acgccacatg caagttttga ataaggacgg tatagaaaac   5880
gtgcttagga atcgctgttg cctactggag gcacagacag aggaaagagg ttttggtagt   5940
tatgacgatg taaggtagtg tggcggagat ggcaatgggg ctaattcttg attctcaacc   6000
ctcatctctc cttttcctat ttggatttcg ttggtgctgt agaaaacaaa aagagagaaa   6060
aatatatatt catttaaaaa atggtgctca ttcccatcca tcaaagatag agtaaaatta   6120
tgtttaataa agtgtaatta ttttatgtac agttctacac tgtcatccct gtgtccattt   6180
ccaaaacttg cacgtgactc tcaatcccac ccagctcaga tttcatgaca attgtggact   6240
gtgacggcaa taaatatttg tgatacaaaa ctcaagttgt atttctgctg actctaattg   6300
cctttccttg attaataata aaatgccttt gtatatgttg atgttgaaga cttcagttat   6360
ttgatgtcac tgacaaattt cacggtggtc aaatctagac tttcaggatc acacaccaat   6420
cgtcccttct ctgctaaccg taacttgttg cgtttcagcc agaagtatca tgcattttaa   6480
taattaattc agtgctatac ctcgaatatt ttcttctcag aatccagatt tcaccaaata   6540
cttgtatata tggggaacaa gaaaagttat atttttggac aggaaagtat gtatgagaaa   6600
ctgctttaac atccacccag aaaataactt tatgtacaat tatttctcta cgtaatcttc   6660
ttcattgtcc tcagagtgct tcagtaatgc caactaatac taaagatgga aaataagcaa   6720
ttatttataa atttgtgcaa tgttaggtta aagcaatgaa ctgttaaagt ggcatagtaa   6780
taatagtcgc aaatattatt ttacttgccc aacaaataca gttcctttgt tttaaaataa   6840
ttattttcaa catttgacca acctagtagc taaaaaatac atagggtgag ctgtttcaaa   6900
agtcatattt gctcaagaca atcaaccctt ctcttttttt ccacttaggt attttctttt   6960
acataccttg aactagcaat acaattttaa aatcaccaac tgaattttgt atctatttta   7020
agtaatatat gtaagacttg aaaataaatg ttttattata atttcttata tgaagtgtta   7080
aattaattga taccagtttc cactggaaca cttatcagct gataatttat ctcaaagaat   7140
ataatctgta atcttgacat ttaaaaatga acatttgtaa ttcagaattt ctttatttct   7200
gaaaccaagt ttgtaaatgt cctttggagg aaggagatat gaattttatc aataaatcaa   7260
gtcttgtcta cctggattgg tcattttctt tcttaaacag gttgcaattc actcttgtgt   7320
tcaaaagtac ttttgattgt catacttgac catccagaga agaattctgt aacccttgca   7380
tgttaacatt caaagataag ttctcaaata tacagcatag taaataatgg catacagtat   7440
ttccaataaa atgataattt atatttaatg tcacaaaatg gtttttagag gtaaaaggtt   7500
ttacaggtaa aagtctcata cttttgactt tggaactaaa aataatttcc aagcaaatta   7560
ttaagttttt aaatcacacg cgaaataata ttagtttaca aagttttcat atatgttaat   7620
ttatctgcat taattaaaga ctttgttgta tattaactta ttccaaatta gttgtctttt   7680
taatgaaata aatttgactc ctaag                                         7705
```

<210> SEQ ID NO 14

<211> LENGTH: 1804
<212> TYPE: PRT
<213> ORGANISM: Mus musculus

<400> SEQUENCE: 14

```
Met Glu Pro Trp Ser Arg Trp Lys Thr Lys Arg Trp Ile Trp Asp Leu
1               5                   10                  15

Thr Ile Ser Thr Leu Ala Leu Thr Phe Leu Phe Gln Ala Arg Glu Val
            20                  25                  30

Arg Gly Ala Ala Pro Val Asp Ile Leu Lys Ala Leu Asp Phe His Asn
        35                  40                  45

Ser Pro Val Gly Ile Ser Lys Thr Thr Gly Phe Cys Thr Asn Arg Lys
    50                  55                  60

Asn Ser Lys Asp Pro Asp Val Ala Tyr Arg Val Thr Glu Glu Ala Gln
65                  70                  75                  80

Ile Ser Ala Pro Thr Lys Gln Leu Phe Pro Gly Gly Ile Phe Pro Gln
                85                  90                  95

Asp Phe Ser Ile Leu Phe Thr Ile Lys Pro Lys Lys Gly Thr Gln Ala
            100                 105                 110

Phe Leu Leu Ser Leu Tyr Asn Glu His Gly Ile Gln Gln Leu Gly Val
        115                 120                 125

Glu Val Gly Arg Ser Pro Val Phe Leu Phe Glu Asp His Thr Gly Lys
    130                 135                 140

Pro Thr Pro Glu Asn Tyr Pro Leu Phe Ser Thr Val Asn Ile Ala Asp
145                 150                 155                 160

Gly Lys Trp His Arg Val Ala Ile Ser Val Glu Lys Lys Thr Val Thr
                165                 170                 175

Met Ile Val Asp Cys Lys Lys Lys Ile Thr Lys Pro Leu Asp Arg Ser
            180                 185                 190

Glu Arg Ser Ile Val Asp Thr Asn Gly Ile Met Val Phe Gly Thr Arg
        195                 200                 205

Ile Leu Glu Thr Asp Val Phe Gln Gly Asp Ile Gln Gln Phe Leu Ile
    210                 215                 220

Thr Gly Asp Pro Lys Ala Ala Tyr Asp Tyr Cys Asp His Tyr Ser Pro
225                 230                 235                 240

Asp Cys Asp Leu Thr Ser Lys Ala Ala Gln Ala Gln Glu Pro His Ile
                245                 250                 255

Asp Glu Tyr Ala Pro Glu Asp Ile Ile Glu Tyr Asp Tyr Glu Tyr Gly
            260                 265                 270

Glu Thr Asp Tyr Lys Glu Ala Glu Ser Val Thr Glu Met Pro Thr Phe
        275                 280                 285

Thr Glu Glu Thr Val Ala Gln Thr Glu Ala Asn Ile Val Asp Asp Phe
    290                 295                 300

Gln Asp Tyr Asn Tyr Gly Thr Met Glu Pro Tyr Gln Thr Glu Thr Pro
305                 310                 315                 320

Arg Arg Val Ser Gly Ser Asn Glu Pro Asn Pro Val Glu Glu Gly Phe
                325                 330                 335

Thr Glu Glu Tyr Leu Thr Gly Glu Asp Tyr Asp Val Gln Arg Asn Thr
            340                 345                 350

Ser Glu Asp Ile Leu Tyr Gly Asn Lys Gly Val Asp Gly Arg Asp Ser
        355                 360                 365

Asp Leu Leu Val Asp Gly Asp Leu Gly Glu Tyr Asp Phe Tyr Glu Tyr
    370                 375                 380

Lys Glu Tyr Glu Glu Arg Thr Thr Thr Ser Pro Asn Glu Glu Phe Gly
```

```
385                 390                 395                 400

Pro Gly Val Pro Ala Glu Thr Asp Phe Thr Glu Thr Ser Ile Asn Gly
                405                 410                 415

His Gly Ala Tyr Gly Glu Lys Gly Gln Lys Gly Glu Pro Ala Val Val
            420                 425                 430

Glu Pro Gly Met Leu Val Glu Gly Pro Pro Gly Pro Ala Gly Pro Ala
        435                 440                 445

Gly Leu Met Gly Pro Pro Gly Leu Gln Gly Pro Ser Gly Leu Pro Gly
    450                 455                 460

Asp Pro Gly Asp Arg Gly Pro Pro Gly Arg Pro Gly Leu Pro Gly Ala
465                 470                 475                 480

Asp Gly Leu Pro Gly Pro Pro Gly Thr Met Leu Met Leu Pro Phe Arg
                485                 490                 495

Tyr Gly Gly Asp Gly Ser Lys Gly Pro Thr Ile Ser Ala Gln Glu Ala
            500                 505                 510

Gln Ala Gln Ala Ile Leu Gln Gln Ala Arg Ile Ala Leu Arg Gly Pro
        515                 520                 525

Pro Gly Pro Met Gly Leu Thr Gly Arg Pro Gly Pro Val Gly Gly Pro
    530                 535                 540

Gly Ser Ala Gly Ala Lys Gly Glu Ser Gly Asp Pro Gly Pro Gln Gly
545                 550                 555                 560

Pro Arg Gly Val Gln Gly Pro Pro Gly Pro Thr Gly Lys Pro Gly Lys
                565                 570                 575

Arg Gly Arg Pro Gly Ala Asp Gly Gly Arg Gly Met Pro Gly Glu Ser
            580                 585                 590

Gly Ser Lys Gly Asp Arg Gly Phe Asp Gly Leu Pro Gly Leu Pro Gly
        595                 600                 605

Asp Lys Gly His Arg Gly Glu Arg Gly Pro Gln Gly Pro Pro Gly Leu
    610                 615                 620

Pro Gly Asp Asp Gly Met Arg Gly Glu Asp Gly Glu Ile Gly Pro Arg
625                 630                 635                 640

Gly Leu Pro Gly Glu Ala Gly Pro Arg Gly Leu Leu Gly Pro Arg Gly
                645                 650                 655

Thr Pro Gly Pro Pro Gly Gln Pro Gly Ile Gly Gly Ile Asp Gly Pro
            660                 665                 670

Gln Gly Pro Lys Gly Asn Met Gly Pro Gln Gly Glu Pro Gly Pro Pro
        675                 680                 685

Gly Gln Gln Gly Asn Pro Gly Pro Gln Gly Leu Pro Gly Pro Gln Gly
    690                 695                 700

Pro Ile Gly Pro Pro Gly Glu Lys Gly Pro Gln Gly Lys Pro Gly Leu
705                 710                 715                 720

Ala Gly Leu Pro Gly Ala Asp Gly Pro Pro Gly His Pro Gly Lys Glu
                725                 730                 735

Gly Gln Ser Gly Glu Lys Gly Ala Leu Gly Pro Pro Gly Pro Gln Gly
            740                 745                 750

Pro Ile Gly Tyr Pro Gly Pro Arg Gly Val Lys Gly Ala Asp Gly Val
        755                 760                 765

Arg Gly Leu Lys Gly Ser Lys Gly Glu Lys Gly Glu Asp Gly Phe Pro
    770                 775                 780

Gly Phe Lys Gly Asp Met Gly Leu Lys Gly Asp Arg Gly Glu Val Gly
785                 790                 795                 800

Gln Val Gly Pro Arg Gly Glu Asp Gly Pro Glu Gly Pro Lys Gly Arg
                805                 810                 815
```

```
Ala Gly Pro Thr Gly Asp Pro Gly Pro Ser Gly Gln Ala Gly Glu Lys
            820                 825                 830

Gly Lys Leu Gly Val Pro Gly Leu Pro Gly Tyr Pro Gly Arg Gln Gly
        835                 840                 845

Pro Lys Gly Ser Thr Gly Phe Pro Gly Phe Pro Gly Ala Asn Gly Glu
    850                 855                 860

Lys Gly Ala Arg Gly Ile Ala Gly Lys Pro Gly Pro Arg Gly Gln Arg
865                 870                 875                 880

Gly Pro Thr Gly Pro Arg Gly Ser Arg Gly Ala Arg Gly Pro Thr Gly
                885                 890                 895

Lys Pro Gly Pro Lys Gly Thr Ser Gly Gly Asp Gly Pro Pro Gly Pro
            900                 905                 910

Pro Gly Glu Arg Gly Pro Gln Gly Pro Gln Gly Pro Val Gly Phe Pro
        915                 920                 925

Gly Pro Lys Gly Pro Pro Gly Pro Ala Gly Lys Asp Gly Leu Pro Gly
    930                 935                 940

His Pro Gly Gln Arg Gly Glu Thr Gly Phe Gln Gly Lys Thr Gly Pro
945                 950                 955                 960

Pro Gly Pro Gly Gly Val Val Gly Pro Gln Gly Pro Thr Gly Glu Thr
                965                 970                 975

Gly Pro Ile Gly Glu Arg Gly His Pro Gly Pro Pro Gly Pro Pro Gly
            980                 985                 990

Glu Gln Gly Leu Pro Gly Ala Ala  Gly Lys Glu Gly Ala  Lys Gly Asp
        995                 1000                 1005

Pro Gly  Pro Gln Gly Ile Ser  Gly Lys Asp Gly Pro  Ala Gly Ile
    1010                 1015                 1020

Arg Gly  Phe Pro Gly Glu Arg  Gly Leu Pro Gly Ala  Gln Gly Ala
    1025                 1030                 1035

Pro Gly  Leu Lys Gly Gly Glu  Gly Pro Gln Gly Pro  Gln Gly Pro
    1040                 1045                 1050

Val Gly  Ser Pro Gly Glu Arg  Gly Ser Ala Gly Thr  Ala Gly Pro
    1055                 1060                 1065

Ile Gly  Leu Pro Gly Arg Pro  Gly Pro Gln Gly Pro  Pro Gly Pro
    1070                 1075                 1080

Ala Gly  Glu Lys Gly Ala Pro  Gly Glu Lys Gly Pro  Gln Gly Pro
    1085                 1090                 1095

Ala Gly  Arg Asp Gly Val Gln  Gly Pro Val Gly Leu  Pro Gly Pro
    1100                 1105                 1110

Ala Gly  Pro Ala Gly Ser Pro  Gly Glu Asp Gly Asp  Lys Gly Glu
    1115                 1120                 1125

Ile Gly  Glu Pro Gly Gln Lys  Gly Ser Lys Gly Asp  Lys Gly Glu
    1130                 1135                 1140

Asn Gly  Pro Pro Gly Pro Pro  Gly Leu Gln Gly Pro  Val Gly Ala
    1145                 1150                 1155

Pro Gly  Ile Ala Gly Gly Asp  Gly Glu Pro Gly Pro  Arg Gly Gln
    1160                 1165                 1170

Gln Gly  Met Phe Gly Gln Lys  Gly Asp Glu Gly Ala  Arg Gly Phe
    1175                 1180                 1185

Pro Gly  Leu Pro Gly Pro Ile  Gly Leu Gln Gly Leu  Pro Gly Pro
    1190                 1195                 1200

Pro Gly  Glu Lys Gly Glu Asn  Gly Asp Val Gly Pro  Met Gly Pro
    1205                 1210                 1215
```

```
Pro Gly  Pro Pro Gly Pro Arg  Gly Pro Gln Gly Pro  Asn Gly Ala
    1220                 1225                 1230

Asp Gly  Pro Gln Gly Pro Pro  Gly Ser Ile Gly Ser  Val Gly Val
    1235                 1240                 1245

Val Gly  Asp Lys Gly Glu Pro  Gly Glu Ala Gly Asn  Pro Gly Pro
    1250                 1255                 1260

Pro Gly  Glu Ala Gly Ser Gly  Gly Leu Lys Gly Glu  Arg Gly Glu
    1265                 1270                 1275

Lys Gly  Glu Ala Gly Pro Pro  Gly Ala Ala Gly Pro  Ala Gly Ile
    1280                 1285                 1290

Lys Gly  Pro Pro Gly Asp Asp  Gly Pro Lys Gly Asn  Pro Gly Pro
    1295                 1300                 1305

Val Gly  Phe Pro Gly Asp Pro  Gly Pro Pro Gly Glu  Pro Gly Pro
    1310                 1315                 1320

Ala Gly  Gln Asp Gly Val Gly  Gly Asp Lys Gly Glu  Asp Gly Asp
    1325                 1330                 1335

Pro Gly  Gln Pro Gly Pro Pro  Gly Pro Ser Gly Glu  Ala Gly Pro
    1340                 1345                 1350

Pro Gly  Pro Pro Gly Lys Arg  Gly Pro Pro Gly Ala  Ser Gly Ser
    1355                 1360                 1365

Glu Gly  Arg Gln Gly Glu Lys  Gly Ala Lys Gly Glu  Ala Gly Ala
    1370                 1375                 1380

Glu Gly  Pro Pro Gly Lys Thr  Gly Pro Val Gly Pro  Gln Gly Pro
    1385                 1390                 1395

Ser Gly  Lys Pro Gly Pro Glu  Gly Leu Arg Gly Ile  Pro Gly Pro
    1400                 1405                 1410

Val Gly  Glu Gln Gly Leu Pro  Gly Ala Ala Gly Gln  Asp Gly Pro
    1415                 1420                 1425

Pro Gly  Pro Leu Gly Pro Pro  Gly Leu Pro Gly Leu  Lys Gly Asp
    1430                 1435                 1440

Pro Gly  Ser Lys Gly Glu Lys  Gly His Pro Gly Leu  Ile Gly Leu
    1445                 1450                 1455

Ile Gly  Pro Pro Gly Glu Gln  Gly Glu Lys Gly Asp  Arg Gly Leu
    1460                 1465                 1470

Pro Gly  Thr Gln Gly Ser Pro  Gly Ala Lys Gly Asp  Gly Gly Ile
    1475                 1480                 1485

Pro Gly  Pro Ala Gly Pro Ile  Gly Pro Pro Gly Pro  Pro Gly Leu
    1490                 1495                 1500

Pro Gly  Pro Ala Gly Pro Lys  Gly Asn Lys Gly Ser  Ser Gly Pro
    1505                 1510                 1515

Thr Gly  Gln Lys Gly Asp Ser  Gly Met Pro Gly Pro  Pro Gly Pro
    1520                 1525                 1530

Pro Gly  Pro Pro Gly Glu Val  Ile Gln Pro Leu Pro  Ile Leu Ser
    1535                 1540                 1545

Pro Lys  Lys Thr Arg Arg His  Thr Glu Ser Ile Gln  Gly Asp Ala
    1550                 1555                 1560

Gly Asp  Asn Ile Leu Asp Tyr  Ser Asp Gly Met Glu  Glu Ile Phe
    1565                 1570                 1575

Gly Ser  Leu Asn Ser Leu Lys  Gln Asp Ile Glu His  Met Lys Phe
    1580                 1585                 1590

Pro Met  Gly Thr Gln Thr Asn  Pro Ala Arg Thr Cys  Lys Asp Leu
    1595                 1600                 1605

Gln Leu  Ser His Pro Asp Phe  Pro Asp Gly Glu Tyr  Trp Ile Asp
```

```
    1610                1615                1620

Pro Asn  Gln Gly Cys Ser Gly  Asp Ser Phe Lys Val  Tyr Cys Asn
    1625                1630                1635

Phe Thr  Ala Gly Gly Glu Thr  Cys Ile Tyr Pro Asp  Lys Lys Ser
    1640                1645                1650

Glu Gly  Val Arg Ile Ser Ser  Trp Pro Lys Glu Lys  Pro Gly Ser
    1655                1660                1665

Trp Tyr  Ser Glu Phe Lys Arg  Gly Lys Leu Leu Ser  Tyr Leu Asp
    1670                1675                1680

Val Glu  Gly Asn Ser Ile Asn  Met Val Gln Met Thr  Phe Leu Lys
    1685                1690                1695

Leu Leu  Thr Ala Ser Ala Arg  Gln Asn Phe Thr Tyr  Asn Cys His
    1700                1705                1710

Gln Ser  Ala Ala Trp Tyr Asp  Val Leu Ser Gly Ser  Tyr Asp Lys
    1715                1720                1725

Ala Leu  Arg Phe Leu Gly Ser  Asn Asp Glu Glu Met  Ser Tyr Glu
    1730                1735                1740

Asn Asn  Pro His Ile Lys Ala  Leu Tyr Asp Gly Cys  Ala Ser Arg
    1745                1750                1755

Lys Gly  Tyr Glu Lys Thr Val  Ile Glu Ile Asn Thr  Pro Lys Ile
    1760                1765                1770

Asp Gln  Val Pro Ile Ile Asp  Val Met Ile Asn Asp  Phe Gly Asp
    1775                1780                1785

Gln Asn  Gln Lys Phe Gly Phe  Glu Val Gly Pro Ala  Cys Phe Leu
    1790                1795                1800

Gly
```

<210> SEQ ID NO 15
<211> LENGTH: 6541
<212> TYPE: DNA
<213> ORGANISM: Mus musculus

<400> SEQUENCE: 15

```
ggactcttca taggggctct gggcccccaa gggcagctgc cgtggtgtga aaggactata     60

ggatcataaa agtgaagggg ctgaagaaga tatattctgt tcccacaaat gccatctgag    120

ggggcacgcg agctacctaa tccctccagg agtaggggtg taccattcca gggctagcga    180

gtgaggaagg tttccaaccc tcacactctc ctgcccaggt ggagatcggg gtggggtttc    240

cccttggtgg ctgtgggcgg gcgtcaggag gcgggagctg gacctagggg cgggggcgag    300

ctggggtctc tgagctgcca gggtggccag gggcacacag tagcggccac cgaagagcaa    360

gcagcactga caagaagagg tgcccccaca acggcacctt gctgcatgga gctgggccac    420

tgaaagctgc tgacatcccg gggtcctggt tccgaggctc agctggcttc tgtctgctgt    480

cagcaccagg actgcctggg atctggcatt ctgagccatg gagcggtgca gccgctgcca    540

ccgcctcctt ctgttcctac ctctggtgct gggtctgagc gctgccccgg gatgggcagg    600

tgctccctct gtggatgtgc ttcgtgccct gaggttcccc tcccttcccg atggtgttcg    660

gagatcaaaa ggggtctgtc cgggtgatgt ggcttaccgt gtggcacggc ctgcccagct    720

cagcgcaccc acgcgccagc tcttcccagg aggctttccc aaagacttct ctctgctgac    780

ggttgtccgg acccgccctg gcctccaggc tcccctcttg actctataca gcgcccaggg    840

agtccagcag ctgggcttgg agctcggccg ccctgtccgc tttctctatg aggaccagag    900

gggacggcca caagcctccg ctcagcccat cttccgaggc ctcagcctag cagatggcaa    960
```

```
atggcaccac gtggctgtgg ctgtgaaggg tcagtctgtc actctcattg tggactgtaa   1020
gaagcgagtt acccggcccc ttcccagaag tgtgcatccg gtgttggaca cccacggggt   1080
ggtgatcttt ggtgcccaca tcctcgacga tgaagtcttt gaaggcgatg ttcaggagct   1140
cctcgttgtc ccaggcgtcc aagctgccta tcagtcttgt gggcagaagg atctggaatg   1200
tgagagagaa cagagggacg gccctcagac tcagaagcct cacagagccc agagatctcc   1260
aaagaaggaa ccagcaagac ttcataagcc acagagccag gagccccaga agcagcccac   1320
tgagtctctc tactatgact acgaaccccc ctattacgat gtgatgacta cggggacagc   1380
ccctgattat caggagcaga cagatcttca ggtctcccca acagctgaca gtttccaggc   1440
agaggaatat ggggagggag gcacagactc cccagcaggg ttctacgatt acacctatgg   1500
ctatggggat gattatcgtg aggagaccga gcttggccct gccctctctg cggagacagc   1560
tcactcagga gccgttgccc acggaccccg gggctaaag ggagagaagg gagagcctgc    1620
agtgctggag cctggtatgt ttgtagaggg acccccaggc ccagaaggcc cagcgggatt   1680
agctggaccc cctggcatcc aggggaaccc aggcccggtt ggagaccccg gtgagagggg   1740
ccccccctggc cgagcagggc tccccggatc agatggaccc cctggtcctc ccggcacatc   1800
tctgatgctt ccattccggt ttggcagtag tgggggtgac aagggccccg tggtggcagc   1860
ccaggaggcc caggcccagg cgattctgca gcaggcacgg ctggcactcc gtgggccccc   1920
tggccccatg ggttacacgg gccgccctgg accattgggt cagcctggga gccctggctt   1980
gaagggagaa tctggagatc tgggcccaca gggccccaga ggacctcagg gcctcacagg   2040
tcctcctggc aaggctggac gaaggggccg agcaggtgct gatggagccc gtgggatgcc   2100
gggagaacct ggcatgaagg gtgaccgagg tttcgacgga cttccagggc tacctggcga   2160
gaagggacaa aggggtgata caggtgctca gggccttcct gggcctcctg gtgaggacgg   2220
agagaggggt gatgatggag agattgggcc acgggggctg cctggagagt cgggacctag   2280
aggactcctt ggccctaaag gcccgcctgg tattcctggg ccgccgggag tccgaggcat   2340
ggacggtccc cacggcccca aagggagctt gggacctcaa ggagagccag gacctcctgg   2400
acaacagggt actcctgggg cccagggcct ccccggacct cagggagcca tcggtcctca   2460
tggagagaag ggtgctcgtg ggaaaccagg cctccctggc atgcctggat cagatggact   2520
cccgggtcac ccagggaagg aaggtccccc tggaaccaaa gggaaccagg gcccgtccgg   2580
accacagggt cctctaggat acccaggccc tcgaggcgtc aagggtgtgg atggaattcg   2640
gggcctgaag ggccacaagg gtgaaaaggg cgaggacggc tttcctgggt tcaaaggtga   2700
cataggagtg aaaggagaca ggggcgaggt tggagtccct ggttccaggg gcgaagacgg   2760
ccctgaaggg ccaaaagggc gcactggacc tacaggagac cctggaccca ctgggctcat   2820
gggcgagaag ggcaagctag gtgttcctgg tctgcctggc tatcctggac gccagggccc   2880
caagggatct ctgggtttcc ctggttttcc tggagccagt ggagagaagg gagctcgggg   2940
cctgtctggg aaatcaggac ctcggggaga acggggcccc acgggtccaa ggggtcagcg   3000
gggacctcga ggtgccactg ggaaatctgg agctaaggga acatcaggtg gtgacggtcc   3060
ccacgggcca cccggagaga ggggtcttcc tggacctcaa ggccccaatg gatttcctgg   3120
ccccaaaggc cctccgggcc ctgcagggaa ggatgggctg ccgggacacc ccggccagag   3180
aggagaagtg ggattccaag gaaagaccgg cccaccaggc ccgcccggag tggtgggacc   3240
tcagggaaca gctggagaaa gtggtcccat gggagagaga ggtcactctg gcccccccagg   3300
```

```
acctcctgga gagcaaggat tgcctggaac atctgggaaa gaagggacca agggtgaccc   3360
tggtcctcct ggggccccag ggaaggatgg tcctgctggt ctgagaggct tcccaggaga   3420
gcgaggcctt ccaggcactg ctggtggacc cggcttgaaa ggaaatgaag gtccagctgg   3480
ccctcctggc cctgcaggct ctcctggcga gcgaggtgca gcaggatcag gggccccat   3540
tggtcccccg ggacgtccag gcccacaagg tcccccctgga gcagcaggag agaaaggcgt   3600
accgggcgag aaaggcccta ttggtcccac tggtcgtgat ggggtgcagg gccccgtggg   3660
gcttcctggt cctgcaggac ccccaggcgt ggctggagag gatggagaca agggtgaagt   3720
gggagaccct ggacagaagg gaaccaaagg aaacaagggt gaacatggcc ctcctggacc   3780
tcctggtccc atcgggcctg tggggcaacc tggagctgcg ggagctgatg gtgagcctgg   3840
agctcgggga ccccagggac actttggagc caaaggtgat gaaggaacaa gagggttcaa   3900
tggacccccg ggacccatcg gcctacaggg cctgccagga ccctctgggg agaaaggaga   3960
aacaggagac ggggggccta tgggaccccc tggccctcca ggacctcgag gccccgctgg   4020
acccaatggt gctgatggcc cacaaggttc ccctggaggt gttggaaact tgggtccccc   4080
tggagaaaag ggtgaaccgg gggagtcagg gtctccaggc gtccagggcg agccgggcgt   4140
caagggacca cgtggagagc gtggtgagaa aggagagtct gggcaggcgg gagaggctgg   4200
accaccgggg cccaaaggcc ctacaggcga caatggcccc aaggggaacc ctggtcctgt   4260
tggctttcct ggggaccctg gcccccctgg agaagctggc ccacggggcc aggatggtgc   4320
taagggagac cgaggcgagg atggcgagcc aggacaacct ggatcccctg gtcccaccgg   4380
ggagaatggg cccccctggac cccttggaaa gcggggacct gctggcactc ctggtccaga   4440
aggacggcaa ggagagaagg gagctaaggg ggaccctggt gctgtggggg ccccgggaaa   4500
gacaggccct gtgggtcctg caggcctagc aggaaagccc ggccccgatg gtcttcgggg   4560
gctcccgggt tcagtgggtc agcaaggccg ccctggagcc acaggccagg ctgggccccc   4620
aggtcctgtg ggacccccag ggcttcctgg cctccggggt gatgctggag ccaaggggga   4680
aaagggtcac ccaggtctca tcggactgat tgggccgact ggagagcaag gcgagaaggg   4740
cgaccgtggc ctccctggac ctcagggctc acccggacag aagggagaga cgggtatccc   4800
aggagcatct ggccccatcg gtcctggagg gcctcctggc ctgcctggac cctctggccc   4860
caaaggagcc aaaggagcca caggcccagc tggacccaag ggagagaagg gtgtccaggg   4920
ccctccagga cacccgggcc ccccgggaga ggtgatccag ccactgccca tccagatgcc   4980
caagaagacc cgccgttccg tggacggaag caaactgata caggatgagg aggctgtgcc   5040
cactggcggt gctccgggca gtcctgcggg gctggaggag atctttggct cactggactc   5100
tctgcgggag gagatcgagc agatgaggag gccggcgggg acccaggaca gccctgctcg   5160
cacctgccag gacttgaagc tgtgccaccc ggagcttcct gatggagagt actgggttga   5220
ccctaaccag ggctgtgctc gggatgcctt ccgggtgttc tgcaacttca cagcaggagg   5280
ggagacgtgt gtcacaccca gggatgacgt cacacagttc tcctacgtgg actccgaggg   5340
ctccccagtg ggcgtggtcc agctcacctt cctgcggctg ctcagcgtct ctgcccacca   5400
ggatgtctcc taccctttgct ctggagtatc ccaggatggt cccctgaaac tccgaggggc   5460
caacgaggat gagctgagcc ctgagaccag cccttatgtc aaggagttca gagatggctg   5520
tcagacccag caaggccgga cggtgttgga ggtgcgcacg cctgtactgg agcagctgcc   5580
cgtgctggat gcctccttcg cagacctggg ggcccccaca agacggggag gggtgcttct   5640
ggggcctgtc tgcttcatgg gctaggcctg tctctgacgc tgtcaaccaa aaccaggtct   5700
```

```
agctggagtc acacagcacg gactccatgt cacctctcgt gaggatctct catcgtctag   5760

agggccttgg gccaggcagg catctcaagc ctcaagtcag gcagcacacg ggctggggt    5820

gaaccagggg gtgccgggat agcccagggg gagggtggta cctgggcctc cagctctccc   5880

acttatgacc cattagagag ctgagacctt tatttaaaac acttccctgt caccccaaat   5940

aagtggaaga gaaaggacac tgtgtatttt gtatttaaaa aaataattat attaattatt   6000

taaagagtgg aagaacaaag taacaaagaa gataaagaga gaaatgccaa aaatcccagc   6060

agatattggg ggcaggtgct gcaagggtgg gcgggcagtc catcctccat tcagggtttc   6120

cctagtgcct gtgggtgtgg cttcctaaaa tgaacccctc cttcctctcc ttccacctgg   6180

ggcactaaga atgctggaac atggtctccc ctgcttcagg actccagccc tctttcccca   6240

gagtctaagc tctgtgacac atgtgtccct gggaggaatg acctgttact taagaccagg   6300

ccgctccttg aagggagacc agaccagagg gctgtgcagg acctgcctct ggcgggttat   6360

ggagatactg aagttctgcc agtggctctg agccactgtc ctggccacac ctcctcacct   6420

tccctgattc tggaaagaaa gctaaggtct agcctatggc cagaagggac tcccaggacc   6480

cctctagccc tatgcccaac gtccctgctg actgacggtt aaacaatgtg attgtctcct   6540

c                                                                   6541
```

```
<210> SEQ ID NO 16
<211> LENGTH: 1715
<212> TYPE: PRT
<213> ORGANISM: Mus musculus

<400> SEQUENCE: 16

Met Glu Arg Cys Ser Arg Cys His Arg Leu Leu Leu Phe Leu Pro Leu
1               5                   10                  15

Val Leu Gly Leu Ser Ala Ala Pro Gly Trp Ala Gly Ala Pro Ser Val
            20                  25                  30

Asp Val Leu Arg Ala Leu Arg Phe Pro Ser Leu Pro Asp Gly Val Arg
        35                  40                  45

Arg Ser Lys Gly Val Cys Pro Gly Asp Val Ala Tyr Arg Val Ala Arg
    50                  55                  60

Pro Ala Gln Leu Ser Ala Pro Thr Arg Gln Leu Phe Pro Gly Gly Phe
65                  70                  75                  80

Pro Lys Asp Phe Ser Leu Leu Thr Val Val Arg Thr Arg Pro Gly Leu
                85                  90                  95

Gln Ala Pro Leu Leu Thr Leu Tyr Ser Ala Gln Gly Val Gln Gln Leu
            100                 105                 110

Gly Leu Glu Leu Gly Arg Pro Val Arg Phe Leu Tyr Glu Asp Gln Arg
        115                 120                 125

Gly Arg Pro Gln Ala Ser Ala Gln Pro Ile Phe Arg Gly Leu Ser Leu
    130                 135                 140

Ala Asp Gly Lys Trp His His Val Ala Val Ala Val Lys Gly Gln Ser
145                 150                 155                 160

Val Thr Leu Ile Val Asp Cys Lys Lys Arg Val Thr Arg Pro Leu Pro
                165                 170                 175

Arg Ser Val His Pro Val Leu Asp Thr His Gly Val Val Ile Phe Gly
            180                 185                 190

Ala His Ile Leu Asp Asp Glu Val Phe Glu Gly Asp Val Gln Glu Leu
        195                 200                 205

Leu Val Val Pro Gly Val Gln Ala Ala Tyr Gln Ser Cys Gly Gln Lys
```

```
    210                 215                 220

Asp Leu Glu Cys Glu Arg Glu Gln Arg Asp Gly Pro Gln Thr Gln Lys
225                 230                 235                 240

Pro His Arg Ala Gln Arg Ser Pro Lys Lys Glu Pro Ala Arg Leu His
                245                 250                 255

Lys Pro Gln Ser Gln Glu Pro Gln Lys Gln Pro Thr Glu Ser Leu Tyr
            260                 265                 270

Tyr Asp Tyr Glu Pro Pro Tyr Tyr Asp Val Met Thr Thr Gly Thr Ala
        275                 280                 285

Pro Asp Tyr Gln Glu Gln Thr Asp Leu Gln Val Ser Pro Thr Ala Asp
    290                 295                 300

Ser Phe Gln Ala Glu Glu Tyr Gly Glu Gly Gly Thr Asp Ser Pro Ala
305                 310                 315                 320

Gly Phe Tyr Asp Tyr Thr Tyr Gly Tyr Gly Asp Asp Tyr Arg Glu Glu
                325                 330                 335

Thr Glu Leu Gly Pro Ala Leu Ser Ala Glu Thr Ala His Ser Gly Ala
            340                 345                 350

Val Ala His Gly Pro Arg Gly Leu Lys Gly Glu Lys Gly Glu Pro Ala
        355                 360                 365

Val Leu Glu Pro Gly Met Phe Val Glu Gly Pro Pro Gly Pro Glu Gly
    370                 375                 380

Pro Ala Gly Leu Ala Gly Pro Pro Gly Ile Gln Gly Asn Pro Gly Pro
385                 390                 395                 400

Val Gly Asp Pro Gly Glu Arg Gly Pro Pro Gly Arg Ala Gly Leu Pro
                405                 410                 415

Gly Ser Asp Gly Pro Pro Gly Pro Pro Gly Thr Ser Leu Met Leu Pro
            420                 425                 430

Phe Arg Phe Gly Ser Ser Gly Gly Asp Lys Gly Pro Val Val Ala Ala
        435                 440                 445

Gln Glu Ala Gln Ala Gln Ala Ile Leu Gln Gln Ala Arg Leu Ala Leu
    450                 455                 460

Arg Gly Pro Pro Gly Pro Met Gly Tyr Thr Gly Arg Pro Gly Pro Leu
465                 470                 475                 480

Gly Gln Pro Gly Ser Pro Gly Leu Lys Gly Glu Ser Gly Asp Leu Gly
                485                 490                 495

Pro Gln Gly Pro Arg Gly Pro Gln Gly Leu Thr Gly Pro Pro Gly Lys
            500                 505                 510

Ala Gly Arg Arg Gly Arg Ala Gly Ala Asp Gly Ala Arg Gly Met Pro
        515                 520                 525

Gly Glu Pro Gly Met Lys Gly Asp Arg Gly Phe Asp Gly Leu Pro Gly
    530                 535                 540

Leu Pro Gly Glu Lys Gly Gln Arg Gly Asp Thr Gly Ala Gln Gly Leu
545                 550                 555                 560

Pro Gly Pro Pro Gly Glu Asp Gly Glu Arg Gly Asp Asp Gly Glu Ile
                565                 570                 575

Gly Pro Arg Gly Leu Pro Gly Glu Ser Gly Pro Arg Gly Leu Leu Gly
            580                 585                 590

Pro Lys Gly Pro Pro Gly Ile Pro Gly Pro Pro Gly Val Arg Gly Met
        595                 600                 605

Asp Gly Pro His Gly Pro Lys Gly Ser Leu Gly Pro Gln Gly Glu Pro
    610                 615                 620

Gly Pro Pro Gly Gln Gln Gly Thr Pro Gly Ala Gln Gly Leu Pro Gly
625                 630                 635                 640
```

```
Pro Gln Gly Ala Ile Gly Pro His Gly Glu Lys Gly Ala Arg Gly Lys
                645                 650                 655

Pro Gly Leu Pro Gly Met Pro Gly Ser Asp Gly Leu Pro Gly His Pro
            660                 665                 670

Gly Lys Glu Gly Pro Pro Gly Thr Lys Gly Asn Gln Gly Pro Ser Gly
        675                 680                 685

Pro Gln Gly Pro Leu Gly Tyr Pro Gly Pro Arg Gly Val Lys Gly Val
    690                 695                 700

Asp Gly Ile Arg Gly Leu Lys Gly His Lys Gly Glu Lys Gly Glu Asp
705                 710                 715                 720

Gly Phe Pro Gly Phe Lys Gly Asp Ile Gly Val Lys Gly Asp Arg Gly
                725                 730                 735

Glu Val Gly Val Pro Gly Ser Arg Gly Glu Asp Gly Pro Glu Gly Pro
            740                 745                 750

Lys Gly Arg Thr Gly Pro Thr Gly Asp Pro Gly Pro Thr Gly Leu Met
        755                 760                 765

Gly Glu Lys Gly Lys Leu Gly Val Pro Gly Leu Pro Gly Tyr Pro Gly
    770                 775                 780

Arg Gln Gly Pro Lys Gly Ser Leu Gly Phe Pro Gly Phe Pro Gly Ala
785                 790                 795                 800

Ser Gly Glu Lys Gly Ala Arg Gly Leu Ser Gly Lys Ser Gly Pro Arg
                805                 810                 815

Gly Glu Arg Gly Pro Thr Gly Pro Arg Gly Gln Arg Gly Pro Arg Gly
            820                 825                 830

Ala Thr Gly Lys Ser Gly Ala Lys Gly Thr Ser Gly Gly Asp Gly Pro
        835                 840                 845

His Gly Pro Pro Gly Glu Arg Gly Leu Pro Gly Pro Gln Gly Pro Asn
    850                 855                 860

Gly Phe Pro Gly Pro Lys Gly Pro Pro Gly Pro Ala Gly Lys Asp Gly
865                 870                 875                 880

Leu Pro Gly His Pro Gly Gln Arg Gly Glu Val Gly Phe Gln Gly Lys
                885                 890                 895

Thr Gly Pro Pro Gly Pro Pro Gly Val Val Gly Pro Gln Gly Thr Ala
            900                 905                 910

Gly Glu Ser Gly Pro Met Gly Glu Arg Gly His Ser Gly Pro Pro Gly
        915                 920                 925

Pro Pro Gly Glu Gln Gly Leu Pro Gly Thr Ser Gly Lys Glu Gly Thr
    930                 935                 940

Lys Gly Asp Pro Gly Pro Pro Gly Ala Pro Gly Lys Asp Gly Pro Ala
945                 950                 955                 960

Gly Leu Arg Gly Phe Pro Gly Glu Arg Gly Leu Pro Gly Thr Ala Gly
                965                 970                 975

Gly Pro Gly Leu Lys Gly Asn Glu Gly Pro Ala Gly Pro Pro Gly Pro
            980                 985                 990

Ala Gly Ser Pro Gly Glu Arg Gly  Ala Ala Gly Ser Gly  Gly Pro Ile
        995                 1000                1005

Gly Pro  Pro Gly Arg Pro Gly  Pro Gln Gly Pro Pro  Gly Ala Ala
    1010                1015                1020

Gly Glu  Lys Gly Val Pro Gly  Glu Lys Gly Pro Ile  Gly Pro Thr
    1025                1030                1035

Gly Arg  Asp Gly Val Gln Gly  Pro Val Gly Leu Pro  Gly Pro Ala
    1040                1045                1050
```

```
Gly Pro  Pro Gly Val Ala Gly  Glu Asp Gly Asp Lys  Gly Glu Val
    1055                 1060                 1065

Gly Asp  Pro Gly Gln Lys Gly  Thr Lys Gly Asn Lys  Gly Glu His
    1070                 1075                 1080

Gly Pro  Pro Gly Pro Pro Gly  Pro Ile Gly Pro Val  Gly Gln Pro
    1085                 1090                 1095

Gly Ala  Ala Gly Ala Asp Gly  Glu Pro Gly Ala Arg  Gly Pro Gln
    1100                 1105                 1110

Gly His  Phe Gly Ala Lys Gly  Asp Glu Gly Thr Arg  Gly Phe Asn
    1115                 1120                 1125

Gly Pro  Pro Gly Pro Ile Gly  Leu Gln Gly Leu Pro  Gly Pro Ser
    1130                 1135                 1140

Gly Glu  Lys Gly Glu Thr Gly  Asp Gly Gly Pro Met  Gly Pro Pro
    1145                 1150                 1155

Gly Pro  Pro Gly Pro Arg Gly  Pro Ala Gly Pro Asn  Gly Ala Asp
    1160                 1165                 1170

Gly Pro  Gln Gly Ser Pro Gly  Gly Val Gly Asn Leu  Gly Pro Pro
    1175                 1180                 1185

Gly Glu  Lys Gly Glu Pro Gly  Glu Ser Gly Ser Pro  Gly Val Gln
    1190                 1195                 1200

Gly Glu  Pro Gly Val Lys Gly  Pro Arg Gly Glu Arg  Gly Glu Lys
    1205                 1210                 1215

Gly Glu  Ser Gly Gln Ala Gly  Glu Ala Gly Pro Pro  Gly Pro Lys
    1220                 1225                 1230

Gly Pro  Thr Gly Asp Asn Gly  Pro Lys Gly Asn Pro  Gly Pro Val
    1235                 1240                 1245

Gly Phe  Pro Gly Asp Pro Gly  Pro Pro Gly Glu Ala  Gly Pro Arg
    1250                 1255                 1260

Gly Gln  Asp Gly Ala Lys Gly  Asp Arg Gly Glu Asp  Gly Glu Pro
    1265                 1270                 1275

Gly Gln  Pro Gly Ser Pro Gly  Pro Thr Gly Glu Asn  Gly Pro Pro
    1280                 1285                 1290

Gly Pro  Leu Gly Lys Arg Gly  Pro Ala Gly Thr Pro  Gly Pro Glu
    1295                 1300                 1305

Gly Arg  Gln Gly Glu Lys Gly  Ala Lys Gly Asp Pro  Gly Ala Val
    1310                 1315                 1320

Gly Ala  Pro Gly Lys Thr Gly  Pro Val Gly Pro Ala  Gly Leu Ala
    1325                 1330                 1335

Gly Lys  Pro Gly Pro Asp Gly  Leu Arg Gly Leu Pro  Gly Ser Val
    1340                 1345                 1350

Gly Gln  Gln Gly Arg Pro Gly  Ala Thr Gly Gln Ala  Gly Pro Pro
    1355                 1360                 1365

Gly Pro  Val Gly Pro Pro Gly  Leu Pro Gly Leu Arg  Gly Asp Ala
    1370                 1375                 1380

Gly Ala  Lys Gly Glu Lys Gly  His Pro Gly Leu Ile  Gly Leu Ile
    1385                 1390                 1395

Gly Pro  Thr Gly Glu Gln Gly  Glu Lys Gly Asp Arg  Gly Leu Pro
    1400                 1405                 1410

Gly Pro  Gln Gly Ser Pro Gly  Gln Lys Gly Glu Thr  Gly Ile Pro
    1415                 1420                 1425

Gly Ala  Ser Gly Pro Ile Gly  Pro Gly Gly Pro Pro  Gly Leu Pro
    1430                 1435                 1440

Gly Pro  Ser Gly Pro Lys Gly  Ala Lys Gly Ala Thr  Gly Pro Ala
```

```
    1445                1450                1455

Gly Pro  Lys Gly Glu Lys Gly  Val Gln Gly Pro Pro  Gly His Pro
    1460                1465                1470

Gly Pro  Pro Gly Glu Val Ile  Gln Pro Leu Pro Ile  Gln Met Pro
    1475                1480                1485

Lys Lys  Thr Arg Arg Ser Val  Asp Gly Ser Lys Leu  Ile Gln Asp
    1490                1495                1500

Glu Glu  Ala Val Pro Thr Gly  Gly Ala Pro Gly Ser  Pro Ala Gly
    1505                1510                1515

Leu Glu  Glu Ile Phe Gly Ser  Leu Asp Ser Leu Arg  Glu Glu Ile
    1520                1525                1530

Glu Gln  Met Arg Arg Pro Ala  Gly Thr Gln Asp Ser  Pro Ala Arg
    1535                1540                1545

Thr Cys  Gln Asp Leu Lys Leu  Cys His Pro Glu Leu  Pro Asp Gly
    1550                1555                1560

Glu Tyr  Trp Val Asp Pro Asn  Gln Gly Cys Ala Arg  Asp Ala Phe
    1565                1570                1575

Arg Val  Phe Cys Asn Phe Thr  Ala Gly Gly Glu Thr  Cys Val Thr
    1580                1585                1590

Pro Arg  Asp Asp Val Thr Gln  Phe Ser Tyr Val Asp  Ser Glu Gly
    1595                1600                1605

Ser Pro  Val Gly Val Val Gln  Leu Thr Phe Leu Arg  Leu Leu Ser
    1610                1615                1620

Val Ser  Ala His Gln Asp Val  Ser Tyr Pro Cys Ser  Gly Val Ser
    1625                1630                1635

Gln Asp  Gly Pro Leu Lys Leu  Arg Gly Ala Asn Glu  Asp Glu Leu
    1640                1645                1650

Ser Pro  Glu Thr Ser Pro Tyr  Val Lys Glu Phe Arg  Asp Gly Cys
    1655                1660                1665

Gln Thr  Gln Gln Gly Arg Thr  Val Leu Glu Val Arg  Thr Pro Val
    1670                1675                1680

Leu Glu  Gln Leu Pro Val Leu  Asp Ala Ser Phe Ala  Asp Leu Gly
    1685                1690                1695

Ala Pro  Thr Arg Arg Gly Gly  Val Leu Leu Gly Pro  Val Cys Phe
    1700                1705                1710

Met Gly
    1715


<210> SEQ ID NO 17
<211> LENGTH: 4733
<212> TYPE: DNA
<213> ORGANISM: Artificial Sequence
<220> FEATURE:
<223> OTHER INFORMATION: synthetic polynucleotide

<400> SEQUENCE: 17

tagttattaa tagtaatcaa ttacggggtc attagttcat agcccatata tggagttccg      60

cgttacataa cttacggtaa atggcccgcc tggctgaccg cccaacgacc cccgcccatt     120

gacgtcaata atgacgtatg ttcccatagt aacgccaata gggactttcc attgacgtca     180

atgggtggag tatttacggt aaactgccca cttggcagta catcaagtgt atcatatgcc     240

aagtacgccc cctattgacg tcaatgacgg taaatggccc gcctggcatt atgcccagta     300

catgacctta tgggactttc ctacttggca gtacatctac gtattagtca tcgctattac     360

catggtgatg cggttttggc agtacatcaa tgggcgtgga tagcggtttg actcacgggg     420
```

```
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggactcag atctcgagct caagcttcga attctgcagt cgacggtacc gcgggcccgg    660
gatccaccgg tcgccaccat ggtgagcaag ggcgaggagc tgttcaccgg ggtggtgccc    720
atcctggtcg agctggacgg cgacgtaaac ggccacaagt tcagcgtgtc cggcgagggc    780
gagggcgatg ccacctacgg caagctgacc ctgaagttca tctgcaccac cggcaagctg    840
cccgtgccct ggcccaccct cgtgaccacc ctgacctacg gcgtgcagtg cttcagccgc    900
taccccgacc acatgaagca gcacgacttc ttcaagtccg ccatgcccga aggctacgtc    960
caggagcgca ccatcttctt caaggacgac ggcaactaca agacccgcgc cgaggtgaag   1020
ttcgagggcg acaccctggt gaaccgcatc gagctgaagg gcatcgactt caaggaggac   1080
ggcaacatcc tggggcacaa gctggagtac aactacaaca gccacaacgt ctatatcatg   1140
gccgacaagc agaagaacgg catcaaggtg aacttcaaga tccgccacaa catcgaggac   1200
ggcagcgtgc agctcgccga ccactaccag cagaacaccc ccatcggcga cggccccgtg   1260
ctgctgcccg acaaccacta cctgagcacc cagtccgccc tgagcaaaga ccccaacgag   1320
aagcgcgatc acatggtcct gctggagttc gtgaccgccg ccgggatcac tctcggcatg   1380
gacgagctgt acaagtaaag cggccgcgac tctagatcat aatcagccat accacatttg   1440
tagaggtttt acttgcttta aaaaacctcc cacacctccc cctgaacctg aaacataaaa   1500
tgaatgcaat tgttgttgtt aacttgttta ttgcagctta taatggttac aaataaagca   1560
atagcatcac aaatttcaca aataaagcat ttttttcact gcattctagt tgtggtttgt   1620
ccaaactcat caatgtatct taaggcgtaa attgtaagcg ttaatatttt gttaaaattc   1680
gcgttaaatt tttgttaaat cagctcattt tttaaccaat aggccgaaat cggcaaaatc   1740
ccttataaat caaaagaata gaccgagata gggttgagtg ttgttccagt ttggaacaag   1800
agtccactat taaagaacgt ggactccaac gtcaaagggc gaaaaaccgt ctatcagggc   1860
gatggcccac tacgtgaacc atcaccctaa tcaagttttt tggggtcgag gtgccgtaaa   1920
gcactaaatc ggaaccctaa agggagcccc cgatttagag cttgacgggg aaagccggcg   1980
aacgtggcga gaaaggaagg gaagaaagcg aaaggagcgg gcgctagggc gctggcaagt   2040
gtagcggtca cgctgcgcgt aaccaccaca cccgccgcgc ttaatgcgcc gctacagggc   2100
gcgtcaggtg gcacttttcg gggaaatgtg cgcggaaccc ctatttgttt atttttctaa   2160
atacattcaa atatgtatcc gctcatgaga caataaccct gataaatgct tcaataatat   2220
tgaaaaagga agagtcctga ggcggaaaga accagctgtg gaatgtgtgt cagttagggt   2280
gtggaaagtc cccaggctcc ccagcaggca gaagtatgca aagcatgcat ctcaattagt   2340
cagcaaccag gtgtggaaag tccccaggct ccccagcagg cagaagtatg caaagcatgc   2400
atctcaatta gtcagcaacc atagtcccgc ccctaactcc gcccatcccg cccctaactc   2460
cgcccagttc cgcccattct ccgccccatg gctgactaat tttttttatt tatgcagagg   2520
ccgaggccgc ctcggcctct gagctattcc agaagtagtg aggaggcttt tttggaggcc   2580
taggcttttg caaagatcga tcaagagaca ggatgaggat cgtttcgcat gattgaacaa   2640
gatggattgc acgcaggttc tccggccgct tgggtggaga ggctattcgg ctatgactgg   2700
gcacaacaga caatcggctg ctctgatgcc gccgtgttcc ggctgtcagc gcaggggcgc   2760
```

```
ccggttcttt ttgtcaagac cgacctgtcc ggtgccctga atgaactgca agacgaggca   2820

gcgcggctat cgtggctggc cacgacgggc gttccttgcg cagctgtgct cgacgttgtc   2880

actgaagcgg gaagggactg gctgctattg ggcgaagtgc cggggcagga tctcctgtca   2940

tctcaccttg ctcctgccga gaaagtatcc atcatggctg atgcaatgcg gcggctgcat   3000

acgcttgatc cggctacctg cccattcgac caccaagcga aacatcgcat cgagcgagca   3060

cgtactcgga tggaagccgg tcttgtcgat caggatgatc tggacgaaga gcatcagggg   3120

ctcgcgccag ccgaactgtt cgccaggctc aaggcgagca tgcccgacgg cgaggatctc   3180

gtcgtgaccc atggcgatgc ctgcttgccg aatatcatgg tggaaaatgg ccgcttttct   3240

ggattcatcg actgtggccg gctgggtgtg gcggaccgct atcaggacat agcgttggct   3300

acccgtgata ttgctgaaga gcttggcggc gaatgggctg accgcttcct cgtgctttac   3360

ggtatcgccg ctcccgattc gcagcgcatc gccttctatc gccttcttga cgagttcttc   3420

tgagcgggac tctggggttc gaaatgaccg accaagcgac gcccaacctg ccatcacgag   3480

atttcgattc caccgccgcc ttctatgaaa ggttgggctt cggaatcgtt ttccgggacg   3540

ccggctggat gatcctccag cgcggggatc tcatgctgga gttcttcgcc caccctaggg   3600

ggaggctaac tgaaacacgg aaggagacaa taccggaagg aacccgcgct atgacggcaa   3660

taaaaagaca gaataaaacg cacggtgttg ggtcgtttgt tcataaacgc ggggttcggt   3720

cccagggctg gcactctgtc gataccccac cgagacccca ttggggccaa tacgcccgcg   3780

tttcttcctt ttccccaccc caccccccaa gttcgggtga aggcccaggg ctcgcagcca   3840

acgtcggggc ggcaggccct gccatagcct caggttactc atatatactt tagattgatt   3900

taaaacttca tttttaattt aaaaggatct aggtgaagat cctttttgat aatctcatga   3960

ccaaaatccc ttaacgtgag ttttcgttcc actgagcgtc agaccccgta gaaaagatca   4020

aaggatcttc ttgagatcct ttttttctgc gcgtaatctg ctgcttgcaa acaaaaaaac   4080

caccgctacc agcggtggtt tgtttgccgg atcaagagct accaactctt tttccgaagg   4140

taactggctt cagcagagcg cagataccaa atactgtcct tctagtgtag ccgtagttag   4200

gccaccactt caagaactct gtagcaccgc ctacatacct cgctctgcta atcctgttac   4260

cagtggctgc tgccagtggc gataagtcgt gtcttaccgg gttggactca agacgatagt   4320

taccggataa ggcgcagcgg tcgggctgaa cggggggttc gtgcacacag cccagcttgg   4380

agcgaacgac ctacaccgaa ctgagatacc tacagcgtga gctatgagaa agcgccacgc   4440

ttcccgaagg gagaaaggcg gacaggtatc cggtaagcgg cagggtcgga acaggagagc   4500

gcacgaggga gcttccaggg ggaaacgcct ggtatcttta tagtcctgtc gggtttcgcc   4560

acctctgact tgagcgtcga tttttgtgat gctcgtcagg ggggcggagc ctatggaaaa   4620

acgccagcaa cgcggccttt ttacggttcc tggccttttg ctggcctttt gctcacatgt   4680

tctttcctgc gttatcccct gattctgtgg ataaccgtat taccgccatg cat          4733
```

<210> SEQ ID NO 18
<211> LENGTH: 239
<212> TYPE: PRT
<213> ORGANISM: Artificial Sequence
<220> FEATURE:
<223> OTHER INFORMATION: synthetic peptide

<400> SEQUENCE: 18

```
Met Val Ser Lys Gly Glu Glu Leu Phe Thr Gly Val Val Pro Ile Leu
1               5                   10                  15
```

```
Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 19
<211> LENGTH: 5059
<212> TYPE: DNA
<213> ORGANISM: Artificial Sequence
<220> FEATURE:
<223> OTHER INFORMATION: synthetic polynucleotide

<400> SEQUENCE: 19

```
tcaatattgg ccattagcca tattattcat tggttatata gcataaatca atattggcta     60

ttggccattg catacgttgt atctatatca taatatgtac atttatattg gctcatgtcc    120

aatatgaccg ccatgttggc attgattatt gactagttat taatagtaat caattacggg    180

gtcattagtt catagcccat atatggagtt ccgcgttaca taacttacgg taaatggccc    240

gcctggctga ccgcccaacg acccccgccc attgacgtca ataatgacgt atgttcccat    300

agtaacgcca atagggactt tccattgacg tcaatgggtg gagtatttac ggtaaactgc    360

ccacttggca gtacatcaag tgtatcatat gccaagtccg ccccctattg acgtcaatga    420

cggtaaatgg cccgcctggc attatgccca gtacatgacc ttacgggact ttcctacttg    480

gcagtacatc tacgtattag tcatcgctat taccatggtg atgcggtttt ggcagtacac    540

caatgggcgt ggatagcggt ttgactcacg gggatttcca agtctccacc ccattgacgt    600

caatgggagt ttgttttggc accaaaatca acgggacttt ccaaaatgtc gtaataaccc    660

cgccccgttg acgcaaatgg gcggtaggcg tgtacggtgg gaggtctata taagcagagc    720

tggtttagtg aaccgtcaga tcactagaag ctttattgcg gtagtttatc acagttaaat    780

tgctaacgca gtcagtgctt ctgacacaac agtctcgaac ttaagctgca gaagttggtc    840
```

```
gtgaggcact gggcaggtaa gtatcaaggt tacaagacag gtttaaggag accaatagaa    900
actgggcttg tcgagacaga gaagactctt gcgtttctga taggcaccta ttggtcttac    960
tgacatccac tttgcctttc tctccacagg tgtccactcc cagttcaatt acagctctta   1020
aggctagagt attaatacga ctcactatag ggctagcaaa gccaccatgg cagaaatcgg   1080
tactggcttt ccattcgacc cccattatgt ggaagtcctg ggcgagcgca tgcactacgt   1140
cgatgttggt ccgcgcgatg gcacccctgt gctgttcctg cacggtaacc cgacctcctc   1200
ctacgtgtgg cgcaacatca tcccgcatgt tgcaccgacc catcgctgca ttgctccaga   1260
cctgatcggt atgggcaaat ccgacaaacc agacctgggt tatttcttcg acgaccacgt   1320
ccgcttcatg gatgccttca tcgaagccct gggtctggaa gaggtcgtcc tggtcattca   1380
cgactggggc tccgctctgg gtttccactg ggccaagcgc aatccagagc gcgtcaaagg   1440
tattgcattt atggagttca tccgccctat cccgacctgg gacgaatggc cagaatttgc   1500
ccgcgagacc ttccaggcct tccgcaccac cgacgtcggc cgcaagctga tcatcgatca   1560
gaacgttttt atcgagggta cgctgccgat gggtgtcgtc cgcccgctga ctgaagtcga   1620
gatggaccat taccgcgagc cgttcctgaa tcctgttgac cgcgagccac tgtggcgctt   1680
cccaaacgag ctgccaatcg ccggtgagcc agcgaacatc gtcgcgctgg tcgaagaata   1740
catggactgg ctgcaccagt cccctgtccc gaagctgctg ttctggggca ccccaggcgt   1800
tctgatccca ccggccgaag ccgctcgcct ggccaaaagc ctgcctaact gcaaggctgt   1860
ggacatcggc ccgggtctga atctgctgca agaagacaac ccggacctga tcggcagcga   1920
gatcgcgcgc tggctgtcga cgctcgagat ttccggcgag ccaaccactg aggatctgta   1980
ctttcagagc gataacgcga tcgccatgga ataagtaagg aatccacatg gcacaggtta   2040
tcaacacgtt tgacggggtt gcggattatc ttcagacata tcataagcta cctgataatt   2100
acattacaaa atcagaagca caagccctcg gctgggtggc atcaaaaggg aaccttgcag   2160
acgtcgctcc ggggaaaagc atcggcggag acatcttctc aaacagggaa ggcaaactcc   2220
cgggcaaaag cggacgaaca tggcgtgaag cggatattaa ctatacatca ggcttcagaa   2280
attcagaccg gattctttac tcaagcgact ggctgattta caaaacaacg gaccattatc   2340
agacctttac aaaaatcaga taatgtttaa acgaattcgg gctcggtacc cggggatcct   2400
ctagagtcga cctgcaggca tgcaagctga tccggctgct aacaaagccc gaaaggaagc   2460
tgagttggct gctgccaccg ctgagcaata actagcataa ccccttgggg cggccgcttc   2520
gagcagacat gataagatac attgatgagt ttggacaaac cacaactaga atgcagtgaa   2580
aaaaatgctt tatttgtgaa atttgtgatg ctattgcttt atttgtaacc attataagct   2640
gcaataaaca agttaacaac aacaattgca ttcattttat gtttcaggtt cagggggaga   2700
tgtgggaggt tttttaagc aagtaaaacc tctacaaatg tggtaaaatc gaattctaat    2760
ggatcctctt tgcgcttgcg ttttcccttg tccagatagc ccagtagctg acattcatcc   2820
ggggtcagca ccgtttctgc ggactggctt tctacgtgtt ccgcttcctt tagcagccct   2880
tgcgccctga gtgcttgcgg cagcgtgagc ttcaaaagaa ttgccagctg ggcgccctc    2940
tggtaaggtt gggaagccct gcaaagtaaa ctggatggct ttcttgccgc caaggatctg   3000
atggcgcagg ggatcaagat ctgatcaaga gacaggatga cggtcgtttc gcatgcttga   3060
acaagatgga ttgcacgcag gttctccggc cgcttgggtg gagaggctat tcggctatga   3120
ctgggcacaa cagacaatcg gctgctctga tgccgccgtg ttccggctgt cagcgcaggg   3180
```

```
gcgcccggtt ctttttgtca agaccgacct gtccggtgcc ctgaatgaac tgcaggacga   3240
ggcagcgcgg ctatcgtggc tggccacgac gggcgttcct tgcgcagctg tgctcgacgt   3300
tgtcactgaa gcgggaaggg actggctgct attgggcgaa gtgccggggc aggatctcct   3360
gtcatctcac cttgctcctg ccgagaaagt atccatcatg gctgatgcaa tgcggcggct   3420
gcatacgctt gatccggcta cctgcccatt cgaccaccaa gcgaaacatc gcatcgagcg   3480
agcacgcact cggatggaag ccggtcttgt cgatcaggat gatctggacg aagagcatca   3540
ggggctcgcg ccagccgaac tgttcgccag gctcaaggcg cgtatgccgg atggtgagga   3600
tctcgtcgtg actcatggcg atgcctgctt gccgaatatc atggtggaaa atggccgctt   3660
ttctggattc atcgactgtg gccggctggg tgtggcggac cgctatcagg acatagcgtt   3720
ggctacccgt gatattgctg aagagcttgg cggcgaatgg gctgaccgct tcctcgtgct   3780
ttacggtatc gccgctcccg attcgcagcg catcgccttc tatcgccttc ttgacgagtt   3840
cttctgagcg ggactctggg gttcgaaatg accgaccaag cgacgcccaa ccggtatcag   3900
ctcactcaaa ggcggtaata cggttatcca cagaatcagg ggataacgca ggaaagaaca   3960
tgtgagcaaa aggccagcaa aaggccagga accgtaaaaa ggccgcgttg ctggcgtttt   4020
tccataggct ccgcccccct gacgagcatc acaaaaatcg acgctcaagt cagaggtggc   4080
gaaacccgac aggactataa agataccagg cgtttccccc tggaagctcc ctcgtgcgct   4140
ctcctgttcc gaccctgccg cttaccggat acctgtccgc ctttctccct tcgggaagcg   4200
tggcgctttc tcatagctca cgctgtaggt atctcagttc ggtgtaggtc gttcgctcca   4260
agctgggctg tgtgcacgaa ccccccgttc agcccgaccg ctgcgcctta tccggtaact   4320
atcgtcttga gtccaacccg gtaagacacg acttatcgcc actggcagca gccactggta   4380
acaggattag cagagcgagg tatgtaggcg gtgctacaga gttcttgaag tggtggccta   4440
actacggcta cactagaagg acagtatttg gtatctgcgc tctgctgaag ccagttacct   4500
tcggaaaaag agttggtagc tcttgatccg gcaaacaaac caccgctggt agcggtggtt   4560
tttttgtttg caagcagcag attacgcgca gaaaaaaagg atttcaagaa gatcctttga   4620
tcttttctac ggggtctgac gctcagtgga acgaaaactc acgttaaggg attttggtca   4680
tgagattatc aaaaaggatc ttcacctaga tccttttata gtccggaaat acaggaacgc   4740
acgctggatg gcccttcgct gggatggtga aaccatgaaa aatggcagct tcagtggatt   4800
aagtgggggt aatgtggcct gtaccctctg gttgcatagg tattcatacg gttaaaattt   4860
atcaggcgcg attgcggcag tttttcgggt ggtttgttgc catttttacc tgtctgctgc   4920
cgtgatcgcg ctgaacgcgt tttagcggtg cgtacaatta agggattatg gtaaatccac   4980
ttactgtctg ccctcgtagc catcgagata aaccgcagta ctccggccac gatgcgtccg   5040
gcgtagagga tcgagatct                                                5059
```

<210> SEQ ID NO 20
<211> LENGTH: 297
<212> TYPE: PRT
<213> ORGANISM: Artificial Sequence
<220> FEATURE:
<223> OTHER INFORMATION: synthetic peptide

<400> SEQUENCE: 20

```
Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30
```

```
Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
    210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
    290                 295
```

<210> SEQ ID NO 21
<211> LENGTH: 72
<212> TYPE: DNA
<213> ORGANISM: Artificial Sequence
<220> FEATURE:
<223> OTHER INFORMATION: synthetic polynucleotide

<400> SEQUENCE: 21

```
gcgatcgctg gctccacctc cggctccggc aagcccggct ccggcgaggg ctccaccaag     60

cccggcgcta gt                                                         72
```

<210> SEQ ID NO 22
<211> LENGTH: 24
<212> TYPE: PRT
<213> ORGANISM: Artificial Sequence
<220> FEATURE:
<223> OTHER INFORMATION: synthetic peptide

```
<400> SEQUENCE: 22

Ala Ile Ala Gly Ser Thr Ser Gly Ser Gly Lys Pro Gly Ser Gly Glu
1               5                   10                  15

Gly Ser Thr Lys Pro Gly Ala Ser
            20
```